(12) United States Patent
McDevitt et al.

(10) Patent No.: US 11,591,395 B2
(45) Date of Patent: Feb. 28, 2023

(54) METHODS OF TREATING PROSTATE CANCER WITH AN ANTI-PSMA/CD3 ANTIBODY

(71) Applicant: Janssen Biotech, Inc., Horsham, PA (US)

(72) Inventors: Theresa McDevitt, Warminster, PA (US); Shoba Shetty, Yardley, PA (US); Hong Xie, Dresher, PA (US)

(73) Assignee: JANSSEN BIOTECH, INC., Horsham, PA (US)

( * ) Notice: Subject to any disclaimer, the term of this patent is extended or adjusted under 35 U.S.C. 154(b) by 334 days.

(21) Appl. No.: 16/852,353

(22) Filed: Apr. 17, 2020

(65) Prior Publication Data

US 2021/0040209 A1 Feb. 11, 2021

Related U.S. Application Data

(60) Provisional application No. 62/836,270, filed on Apr. 19, 2019.

(51) Int. Cl.
| | | |
|---|---|---|
| *C07K 16/28* | (2006.01) | |
| *A61P 35/04* | (2006.01) | |
| *A61K 9/00* | (2006.01) | |
| *C07K 16/30* | (2006.01) | |
| *A61K 45/06* | (2006.01) | |

(52) U.S. Cl.
CPC ........ *C07K 16/2809* (2013.01); *A61K 9/0019* (2013.01); *A61P 35/04* (2018.01); *C07K 16/3069* (2013.01); *A61K 45/06* (2013.01)

(58) Field of Classification Search
CPC .................................................. C07K 16/2809
See application file for complete search history.

(56) References Cited

U.S. PATENT DOCUMENTS

| | | |
|---|---|---|
| 541,606 A | 6/1895 | Fellows |
| 4,683,195 A | 7/1987 | Mullis |
| 5,208,020 A | 5/1993 | Chari |
| 5,223,409 A | 6/1993 | Ladner |
| 5,225,539 A | 7/1993 | Winter |
| 5,403,484 A | 4/1995 | Ladner |
| 5,427,908 A | 6/1995 | Dower |
| 5,571,698 A | 11/1996 | Ladner |
| 5,580,717 A | 12/1996 | Dower |
| 5,635,483 A | 6/1997 | Pettit |
| 5,712,374 A | 1/1998 | Kuntsmann |
| 5,714,586 A | 2/1998 | Kunstmann |
| 5,739,116 A | 4/1998 | Hamann |
| 5,767,285 A | 6/1998 | Hamann |
| 5,770,701 A | 6/1998 | McGahren |
| 5,773,001 A | 6/1998 | Hamann |
| 5,780,588 A | 7/1998 | Pettit |
| 5,877,296 A | 3/1999 | Hamann |
| 5,885,793 A | 3/1999 | Griffiths |
| 5,969,108 A | 10/1999 | McCafferty |
| 6,054,297 A | 4/2000 | Carter |
| 6,150,584 A | 11/2000 | Kucherlapati |
| 6,172,197 B1 | 1/2001 | McCafferty |
| 6,521,404 B1 | 2/2003 | Griffiths |
| 6,521,427 B1 | 2/2003 | Evans |
| 6,544,731 B1 | 4/2003 | Griffiths |
| 6,555,313 B1 | 4/2003 | Griffiths |
| 6,582,915 B1 | 6/2003 | Griffiths |
| 6,582,959 B2 | 6/2003 | Kim |
| 6,593,081 B1 | 7/2003 | Griffiths |
| 6,630,579 B2 | 10/2003 | Chari |
| 6,670,127 B2 | 12/2003 | Evans |
| 6,703,020 B1 | 3/2004 | Thorpe |
| 6,818,749 B1 | 11/2004 | Kashmiri |
| 6,884,879 B1 | 4/2005 | Baca |
| 7,060,269 B1 | 6/2006 | Baca |
| 7,498,298 B2 | 3/2009 | Doronina |
| 7,709,226 B2 | 5/2010 | Foote |
| 8,748,356 B2 | 6/2014 | Raghunathan |
| 10,844,122 B2 | 11/2020 | Anderson |
| 2003/0190317 A1 | 10/2003 | Baca |
| 2003/0203409 A1 | 10/2003 | Kim |
| 2003/0206899 A1 | 11/2003 | Ferrara |
| 2005/0112126 A1 | 5/2005 | Baca |
| 2005/0186208 A1 | 8/2005 | Fyfe |
| 2006/0009360 A1 | 1/2006 | Pifer |
| 2007/0287170 A1 | 12/2007 | Davis |
| 2009/0182127 A1 | 7/2009 | Kjaergaard |
| 2010/0015133 A1 | 1/2010 | Igawa |
| 2010/0028637 A1 | 2/2010 | Tavsanli |
| 2010/0261620 A1 | 10/2010 | Almagro |
| 2011/0123532 A1 | 5/2011 | Gurney |
| 2014/0141000 A1 | 5/2014 | Chiu |
| 2016/0068605 A1 | 3/2016 | Nemeth |

(Continued)

FOREIGN PATENT DOCUMENTS

| | | |
|---|---|---|
| CL | 201802063 | 11/2018 |
| CL | 202003033 | 4/2021 |

(Continued)

OTHER PUBLICATIONS

"FOLH1_HUMAN", Jun. 1, 1994, retrieved from internet, https://www.uniprot.org/uniprot/Q04609.
Abhinandan, et al., "Analysis and improvements to Kbat and structurally correct numbering of antibody variable domains", Molecular Immunology, (2008), vol. 45, pp. 3832-3839.
Adan, et al., "Flow cytometry: basic principles and applications", Crit Rev Biotechnol, (2017), vol. 37, No. 2, pp. 163-176.
Baccala, et al., "Expression of prostate-specific membrane antigen in tumor-associated neovasculature of renal neoplasms", Urology, vol. 70, No. 2 (2007), pp. 385-390.
Blincyto® [US FDA Product Label], Thousand Oaks, USA: Amgen Inc.; Dec. 2018.

(Continued)

*Primary Examiner* — Elly-Gerald Stoica
(74) *Attorney, Agent, or Firm* — Riverside Law LLP

(57) ABSTRACT

Bispecific monoclonal antibodies and methods for treating cancer are set forth herein.

8 Claims, 13 Drawing Sheets

Specification includes a Sequence Listing.

(56) References Cited

U.S. PATENT DOCUMENTS

| | | | |
|---|---|---|---|
| 2016/0347840 A1 | 12/2016 | Anderson | |
| 2019/0352421 A1* | 11/2019 | Adams | C07K 16/3061 |
| 2020/0024360 A1 | 1/2020 | Anderson | |
| 2021/0079115 A1 | 3/2021 | McDevitt | |

FOREIGN PATENT DOCUMENTS

| | | |
|---|---|---|
| EP | 0666868 B1 | 4/2002 |
| EP | 0666868 B2 | 6/2006 |
| WO | 8801649 A1 | 3/1988 |
| WO | 9004036 A1 | 4/1990 |
| WO | 9007861 A1 | 7/1990 |
| WO | 9201047 A1 | 1/1992 |
| WO | 9222653 A1 | 12/1992 |
| WO | 9410202 A1 | 5/1994 |
| WO | 9411026 A2 | 5/1994 |
| WO | 9413804 A1 | 6/1994 |
| WO | 9411026 A3 | 8/1994 |
| WO | 9630046 A1 | 10/1996 |
| WO | 9844001 A1 | 10/1998 |
| WO | 9845332 A3 | 12/1998 |
| WO | 9945962 A1 | 9/1999 |
| WO | 0243478 A2 | 6/2002 |
| WO | 02066470 A1 | 8/2002 |
| WO | 2002066630 A1 | 8/2002 |
| WO | 0243478 A3 | 8/2003 |
| WO | 03077914 A1 | 9/2003 |
| WO | 0243478 A8 | 5/2004 |
| WO | 2004106380 A2 | 12/2004 |
| WO | 2005012359 A2 | 2/2005 |
| WO | 2005044853 A2 | 5/2005 |
| WO | 2004106380 A3 | 6/2005 |
| WO | 2005048935 A2 | 6/2005 |
| WO | 2005012359 A3 | 12/2005 |
| WO | 2005113556 A1 | 12/2005 |
| WO | 2005121142 A1 | 12/2005 |
| WO | 2005044853 A3 | 1/2006 |
| WO | 2006028936 A2 | 3/2006 |
| WO | 2006028936 A3 | 9/2006 |
| WO | 2007004415 A1 | 1/2007 |
| WO | 2008024725 A1 | 2/2008 |
| WO | 2009018386 A1 | 2/2009 |
| WO | 2009080251 A1 | 7/2009 |
| WO | 2009080252 A1 | 7/2009 |
| WO | 2009080254 A1 | 7/2009 |
| WO | 2009085462 A1 | 7/2009 |
| WO | 2009085983 A1 | 7/2009 |
| WO | 2009114870 A2 | 9/2009 |
| WO | 2010006086 A2 | 1/2010 |
| WO | 2009114870 A3 | 2/2010 |
| WO | 2010006086 A3 | 4/2010 |
| WO | 2010036380 A1 | 4/2010 |
| WO | 2010037836 A2 | 4/2010 |
| WO | 2010136172 A1 | 12/2010 |
| WO | 2011131746 A2 | 10/2011 |
| WO | 2011131746 A3 | 12/2011 |
| WO | 2013019906 A1 | 2/2013 |
| WO | 2013174873 A1 | 11/2013 |
| WO | 2013019906 A9 | 3/2014 |
| WO | 2015095392 A1 | 6/2015 |
| WO | 2015158636 A1 | 10/2015 |
| WO | 2015184207 A1 | 12/2015 |
| WO | 2015158636 A8 | 11/2016 |
| WO | 2016179534 | 11/2016 |
| WO | 2017023761 | 2/2017 |
| WO | 2019125982 | 6/2019 |
| WO | 2019224718 | 11/2019 |

OTHER PUBLICATIONS

Bostwick, et al., "Prostate Specific Membrane Antigen Expression in Prostatic Intraepithelial Neoplasia and Adenocarcinoma", Cancer, (1998), vol. 82, pp. 2256-2261.

Bruggemann, et al., "Human antibody production in transgenic mice: expression from 100 kb of the human IgH locus", Eur. J Immunol., (1991), vol. 21, pp. 1323-1326.

Bruggemann, et al., "Production of human antibody repertoires in transgenic mice", Current Opinion in Biotechnology, (1997), vol. 8, pp. 455-458.

Buhler et al., "A bispecific diabody directed against prostate-specific membrane antigen and CD3 induces T-cell mediated lysis of prostate cancer cells", Cancer Immunology, Immunotherapy, vol. 57, No. 1 (2007), pp. 43-52.

Chames, et al., "Bispecific antibodies for cancer therapy", Current Opinion in Drug Discovery & Development, (2009), vol. 12, No. 2, pp. 276-283.

Chang, "Overview of Prostate-Specific Membrane Antigen", Reviews in Urology, vol. 6, Suppl. 10 (2004), pp. S13-S18.

Chang, et al., "Five Different Anti-Prostate-specific Membrane Antigen (PSMA) Antibodies Confirm PSMA Expression in Tumor-associated Neovasculature", Cancer Research, vol. 59, No. 13 (1999), pp. 3192-3198.

Chang, et al., "Metastatic renal cell carcinoma neovasculature expresses prostate-specific membrane antigen", Urology, vol. 57, No. 4 (2001), pp. 801-805.

Chari, et al.,"Immunoconjugates Containing Novel Maytansinoids Promising Anticancer Drugs", Cancer Research, (1992), vol. 52, pp. 127-131.

Chothia, et al., "Canonical Structures for the Hypervariable Regions of Immunoglobulins", J. Mol. Biol., (1987), vol. 196, pp. 901-917.

Cline, et al., "Perspectives for Gene Therapy: inserting new genetic information into mammalian cells by physical techniques and viral vectors", Pharmac. Ther., (1985), vol. 29, pp. 69-92.

Dranoff, et al., "Vaccination with irradiated tumor cells engineered to secrete murine granulocyte-macrophage colony-stimulating factor stimulates potent, specific, and long-lasting anti-tumor immunity", Proc. Natl. Acad. Sci., (1993), vol. 90, pp. 3539-3543.

Dubowchik, et al., "Doxorubicin Immunoconjugates Containing Bivalent, Lysosomally-Cleavable Dipeptide Linkages", Bioorganic & Medicinal Chemistry Letters, (2002), vol. 12, pp. 1529-1532.

Edwards, et al., The remarkable flexibility of the human antibody repertoire; isolation of over one thousand different antibodies to a single protein, BLyS, Journal of Molecular Biology, vol. 334, No. 1 (2003), pp. 103-118.

Fishwild et al., "High-avidity human IgGk monoclonal antibodies from a novel strain of minilocus transgenic mice", Nat Biotechnol 14(7):845-851 (1996).

Freshney, et al., "Culture of Animal Cells: A Manual of Basic Technique, 3rd edition", Journal of Immunological Methods, (1995), vol. 183, pp. 291-292.

Friedrich et al, "Regression of human prostate cancer xenografts in mice by Amg 212/BAY2010112, a novel PSMA/CD3-Bispecific BiTE antibody cross-reactive with non-human primate antigens", Molecular Cancer Therapeutics, vol. 11, No. 12 (2012), pp. 2664-2673.

Gadi, et al., "In vivo sensitization of ovarian tumors to chemotherapy by expression of E. coli purine nucleoside phosphorylase in a small fraction of cells", Gene Therapy, (2000), vol. 7, pp. 1738-1743.

Goding, "Monoclonal Antibodies: Principles and Practice", Academic Press, (1996), pp. 59-103.

Goel, et al., "Plasticity within the Antigen-Combining Site May Manifest as Molecular Mimicry in the Humoral Immune Response", The Journal of Immunology, vol. 173, No. 12 (2004), pp. 7358-7367.

Green et al, "Antigen-specific human monoclonal antibodies from mice engineered with human Ig heavy and light chain YACs", Nature Genetics 7:13-21 (1994).

Green, "Antibody engineering via genetic engineering of the mouse:XenoMouse strains are a vehicle for the facile generation of therapeutic human monoclonal antibodies", Journal of Immunological Methods, (1999), vol. 231, pp. 11-23.

Green, et al., "Regulation of B Cell Development by Variable Gene Complexity in Mice Reconstituted with Human Immunoglobulin Yeast Artificial Chromosomes", J. Exp. Med., (1998), vol. 188, No. 3, pp. 483-495.

(56) References Cited

OTHER PUBLICATIONS

Hernandez-Hoyos et al, "MOR209/ES414, a Novel Bispecific Antibody Targeting PSMA for the Treatment of Metastatic Castration-Resistant Prostate Cancer", Molecular Cancer Therapeutics US, vol. 15, No. 9 (2016), pp. 2155-2165.
Hinman, et al., "Preparation and Characterization of Monoclonal Antibody Conjugates of the Calicheamicins: A Novel and Potent Family of Antitumor Antibiotics", Cancer Research, (1993), vol. 53, pp. 3336-3342.
Hoogenboom, et al., "By-passing Immunisation Human Antibodies from Synthetic Repertoires of Germline VH Gene Segments Rearranged in Vitro", J. Mol. Biol., (1992), vol. 227, pp. 381-388.
Hudes, et al., "Temsirolimus, Interferon Alfa, or Both for Advanced Renal-Cell Carcinoma", N Engl J Med, (2007), vol. 356, No. 22, pp. 2271-2281.
Hummel et al, "Phase 1 study of pasotuxizumab (BAY 2010112), a PSMA-targeting Bispecific T cell Engager (BiTE) immunotherapy for metastatic castration-resistant prostate cancer (mCRPC).", Journal of Clinical Oncology, vol. 37, No. 15 (2019), Abstr 5034.
Jeffrey, S.C., et al., "Dipeptide-based highly potent doxorubicin antibody conjugates", Bioorg. Med. Chem. Lett., (2006), vol. 16, pp. 358-362.
Kawakami, M., et al., "Enhanced Expression of Prostate-specific Membrane Antigen Gene in Prostate Cancer as Revealed by in Situ Hybridization", Cancer Research, (1997), vol. 57, pp. 2321-2324.
Kenter, M.J.H., et al., "TGN1412 and The Lancet's solicitation of reports of phase I trials", Lancet, (2006), vol. 368, pp. 2206-2207.
Kim, N.W., et al., "Specific Association of Human Telomerase Activity with Immortal Cells and Cancer", Science, (1994), vol. 266, pp. 2011-2013.
King, H.D., et al., "Monoclonal Antibody Conjugates of Doxorubicin Prepared with Branched Peptide Linkers: Inhibition of Aggregation by Methoxytriethyleneglycol Chains", J. Med. Chem., (2002), vol. 45, pp. 4336-4343.
Kinoshita et al., "Expression of prostate-specific membrane antigen in normal and malignant human tissues", World Journal of Surgery, vol. 30, No. 4 (2006), pp. 628-636.
Klinger et al., Harnessing T cells to fight G. Harnessing Immunol Reviews, vol. 270, No. 1 (2016 ):193-208.
Klinger, et al., "Immunopharmacologic response of patients with B-lineage acute lymphoblastic leukemia to continuous infusion of T cell-engaging CD19/CD3-bispecific BiTE antibody blinatumomab", Blood, vol. 119, No. 26 (2012), pp. 6226-6233.
Knappik, et al., "Fully Synthetic Human Combinatorial Antibody Libraries (HuCAL) Based on Modular Consensus Frameworks and CDRs Randomized with Trinucleotides," Journal of Molecular Biology, 296(1): 57-86 (2000).
Kohler, et al., "Continuous cultures of fused cells secreting antibody of predefined specificity", Nature, (1975), vol. 256, pp. 495-497.
Kratz, F., et al., "Prodrugs of Anthracyclines in Cancer Chemotherapy", Current Medicinal Chemistry, (2006), vol. 13, pp. 477-523.
Krebs, B., et al., "High-throughput generation and engineering of recombinant human antibodies", Journal of Immunological Methods, (2001), vol. 254, pp. 67-84.
Kugler, A., et al., "Regression of human metastatic renal cell carcinoma after vaccination with tumor cell-dendritic cell hybrids", Nature Medicine, (2000), vol. 6, No. 3, pp. 332-336.
Lathey, J.L., et al., "Production and characterization of an anti-idiotypic antibody specific for a monoclonal antibody to glycoprotein D of herpes simplex virus", Immunology, (1986), vol. 57, pp. 29-35.
Lee, et al. , "Current concepts in the diagnosis and management of cytokine release syndrome", Blood. 2014, vol. 124, No. 2 (2014), pp. 188-195.
Lefranc, M.P., et al., "IMGT unique numbering for immunoglobulin and T cell receptor variable domains and Ig superfamily V-like domains", Developmental and Comparative Immunology, (2003), vol. 27, pp. 55-77.

Lemon, et al., "HPN424, a half-life extended, PSMA/CD3-specific TriTAC for the treatment of metastatic prostate cancer", Cancer Research, vol. 78, No. 13 Supplement (2018), Abstract 1773.
Li, P., et al., "Design and Synthesis of Paclitaxel Conjugated with an ErbB2-Recognizing Peptide, EC-1", Biopolymers, (2007), vol. 87, No. 4, pp. 225-230.
Liu, D.Z., et al., "Synthesis of 2'-paclitaxel methyl 2-glucopyranosyl succinate for specific targeted delivery to cancer cells", Bioorganic & Medicinal Chemistry Letters, (2007), vol. 17, pp. 617-620.
Lloyd, et al., "Modelling the human immune response: performance of a 1011 human antibody repertoire against a broad panel of therapeutically relevant antigents", Protein Engineering Design & Selection, vol. 22, No. 3 (2009), pp. 159-168.
Lode, H.N., et al., "Targeted Therapy with a Novel Enediyene Antibiotic Calicheamicin ell Effectively Suppresses Growth and dissemination of Liver Metastases in a Syngeneic Model of Murine Neuroblastoma", Cancer Research, (1998), vol. 58, pp. 2925-2928.
Lonberg et al. "Antigen-specific human antibodies from mice comprising four distinct genetic modifications", Nature 368:856-859 (1994).
Lonberg et al., "Human Antibodies from Transgenic Mice", Int Rev Immunol 13(1):65-93 (1995).
Maclennan, D.H., et al., "Structure-Function Relationships in the Ca2+-Binding and Translocation Domain of SERCA1 : physiological correlates in Brody disease", Acta Physiol Scand, (1998), vol. 163, suppl. 643, pp. 55-67.
Malia, et al., Epitope mapping and structural basis for the recognition of phosphorylated tau by the anti-tau antibody AT8, Proteins, vol. 84, No. 4 (2016), pp. 427-434.
Marks, J.D., et al., "By-passing Immunization Human Antibodies from V-gene Libraries Displayed on Phase", J. Mol. Biol., (1991), vol. 222, pp. 581-597.
Mcdermott et al., "PD-1 as a potential target in cancer therapy", Cancer Medicine, vol. 2, No. 5 (2013), pp. 662-673.
Mendez, et al., "Functional transplant of megabase human immunoglobulin loci recapitulates human antibody response in mice," Nature Genetics, 15(2): 146-156 (1997).
Mitsiades, C.S., et al., "Molecular staging by RT-PCR analysis for PSA and PSMA in peripheral blood and bone marrow samples is an independent predictor of time to biochemical failure following radical prostatectomy for clinically localized prostate cancer", Clinical & Experimental Metastasis, (2004), vol. 21, pp. 495-505.
Mokyr, M B., et al., "Realization of the Therapeutic Potential of CTLA-4 Blockade in Low-Dose Chemotherapy-treated Tumor-bearing Mice", Cancer Research, (1998), vol. 58, pp. 5301-5304.
Motzer, R.J., et al., "Efficacy of everolimus in advanced renal cell carcinoma: a double-blind, randomized, placebo-controlled phase III trial", Lancet, (2008), vol. 372, pp. 449-456.
Nagy, A., et al., "Stability of cytotoxic luteinizing hormone-releasing hormone conjugate (AN-152) containing doxorubicin 14-O-hemiglutarate in mouse and human serum in vitro: Implications for the design of preclinical studies", PNAS, (2000), vol. 97, No. 2, pp. 829-834.
Nestle, F.O., et al., "Vaccination of melanoma patients with peptide- or tumor lysate-pulsed dendritic cells", Nature Medicine, (1998), vol. 4, No. 3, pp. 328-332.
Nunez-Prado, N., et al., "The coming of age of engineered multivalent antibodies", Drug Discovery Today, (2015), vol. 20, No. 5, pp. 588-594.
Okayama, H., et al., "A cDNA Cloning Vector That Permits Expression of cDNA Inserts in Mammalian Cells", Molecular and Cellular Biology, (1983), vol. 3, No. 2, pp. 280-289.
Padlan, E.A., "A Possible Procedure for Reducing the Immunogenicity of Antibody Variable Domains While Preserving Their Ligand-Binding Properties", Molecular Immunology, (1991), vol. 28, Nos. 4/5, pp. 489-498.
Pal, S.K., et al., "Programmed Death-1 Inhibition in Renal Cell Carcinoma: Clinical Insights and Future Directions", Clinical Advances in Hematology & Oncology, (2014), vol. 12, No. 2, pp. 90-99.
Popkov, M., et al., "Human/mouse cross-reactive anti-VEGF receptor 2 recombinant antibodies selected from an immune b9 allotype rabbit antibody library", Journal of Immunological Methods, (2004), vol. 288, pp. 149-164.

(56) References Cited

OTHER PUBLICATIONS

Presta, L.G., et al., "Humanization of an Anti-Vascular Endothelial Growth Factor Monoclonal Antibody for the Therapy of Solid Tumors and Other Disorders", Cancer Research, (1997), vol. 57, pp. 4593-4599.
Ramadoss, et al., "An Anti-B Cell Maturation Antigen Bispecific Antibody for Multiple Myeloma", Journal of the American Chemical Society, vol. 137, No. 16 (2015), pp. 5288-5291.
Restifo, N.P., et al., "Cancer Vaccines", Chapter 61, Cancer: Principles & Practice of Oncology, Fifth Edition (1997), pp. 3023-3043.
Rini, B.I., et al., "Phase III Trial of Bevacizumab Plus Interferon Alfa Versus Interferon Alfa Monotherapy in Patients With Metastatic Renal Cell Carcinoma: Final Results of CALGB 90206", Journal of Clinical Oncology, (2010), vol. 28, No. 13, pp. 2137-2143.
Rosenberg, S.A., "Development of Cancer Vaccines", American Society of Clinical Oncology, (2000), pp. 60-62.
Sasaki ,et al., "Stucture-Mutation Analysis of the ATPase Site of Dictyostellium Discoideum Myosin II.", AdvBiophys, 1998, pp. 1-24, vol. 35.
Sawicki et al., "Diagnostic potential of PET/CT using a 68Ga-labelled prostate-specific membrane antigen ligand in whole-body staging of renal cell carcinoma: initial experience", European Journal of Nuclear Medicine and Molecular Imaging, vol. 44, No. 1 (2017), pp. 102-107.
Seymour, et al., iRECIST: guidelines for response criteria for use in trials testing immunotherapeutics, Lancet Oncology, vol. 18, No. 3 (2017), E143-E152.
Sheets, et al., "Efficient construction of a large nonimmune phage antibody library: The production of high-affinity human single-chain antibodies to protein antigens", Proc. Natl. Acad. Sci., (1998), vol. 95, pp. 6157-6162.
Shi, et al., "De Novo Selection of High-Affinity Antibodies from Synthetic Fab Libraries Displayed on Phage as pIX Fusion Proteins", J. Mol. Biol., (2010), vol. 397, pp. 385-396.
Spatz, et al., "Comprehensive Evaluation of Prostate Specific Membrane Antigen Expression in the Vasculature of Renal Tumors: Implications for Imaging Studies and Prognostic Role", Journal of Urology, vol. 199, No. 2 (2018), pp. 370-377.
Suto, et al., "A Mechanism for the Specific Immunogenicity of Heat Shock Protein-Chaperoned Peptides", Science, (1995), vol. 269, pp. 1585-1588.
Tamura, et al., "Immunotherapy of Tumors with Autologous Tumor-Derived Heat Shock Protein Preparations", Science, (1997), vol. 278, pp. 117-120.
Thalmann, et al., "Androgen-independent Cancer Progression and Bone Metastasis in the LNCaP Model of Human Prostate Cancer", Cancer Research, (1994), vol. 54, pp. 2577-2581.
Torgov, et al., "Generation of an Intensely Potent Anthracycline by a Monoclonal Antibody-B-Galactosidase Conjugate", Bioconjugate Chem., (2005), vol. 16, pp. 717-721.
Troy, D.B., "Remington: The Science and Practice of Pharmacy", 21st Edition, Lippincott, Williams & Wilkins, (2006), Table of Contents.
Vaughan, et al., "Human Antibodies with Sub-nanomolar Affinities Isolated from a Large Non-immunized Phage Display Library", Nature Biotechnology, (1996), vol. 14, pp. 309-314.
Vitetta, E.S., et al., "Redesigning Nature's Poisons to Create Anti-Tumor Reagents", Science, (1987), vol. 238, p. 1098.
Wildman, D.E., et al., "Implications of natural selection in shaping 99.4% nonsynonymous DNA identity between humans and chimpanzees: Enlarging genus *Homo*", PNAS, (2003), vol. 100, No. 12, p. 7181.
Wranik, B.J., et al., "LUZ-Y, a Novel Platform for the Mammalian Cell Production of Full-length IgG-bispecific Antibodies", Journal of Biological Chemistry, (2012), vol. 287, 52, pp. 43331-43339.
Wright, G.L., et al., "Upregulation of Prostate-Specific Membrance Antigen After Androgen-Deprivation Therapy", Urology, (1996), vol. 48, pp. 326-334.
Yang, X.D., et al., "Eradication of Established Tumors by a Fully Human Monoclonal Antibody to the Epidermal Growth Factor Receptor without Concomitant Chemotherapy", Cancer Research, (1999), vol. 59, pp. 1236-1243.
Zimmerman, et al., "Unleashing the clinical power of T cells: CD19/CD3 bi-specific T cell engager (BiTE(R)) antibody construct blinatumomab as a potential therapy", International Immunology, vol. 27, No. 1 (2015), pp. 31-37.

\* cited by examiner

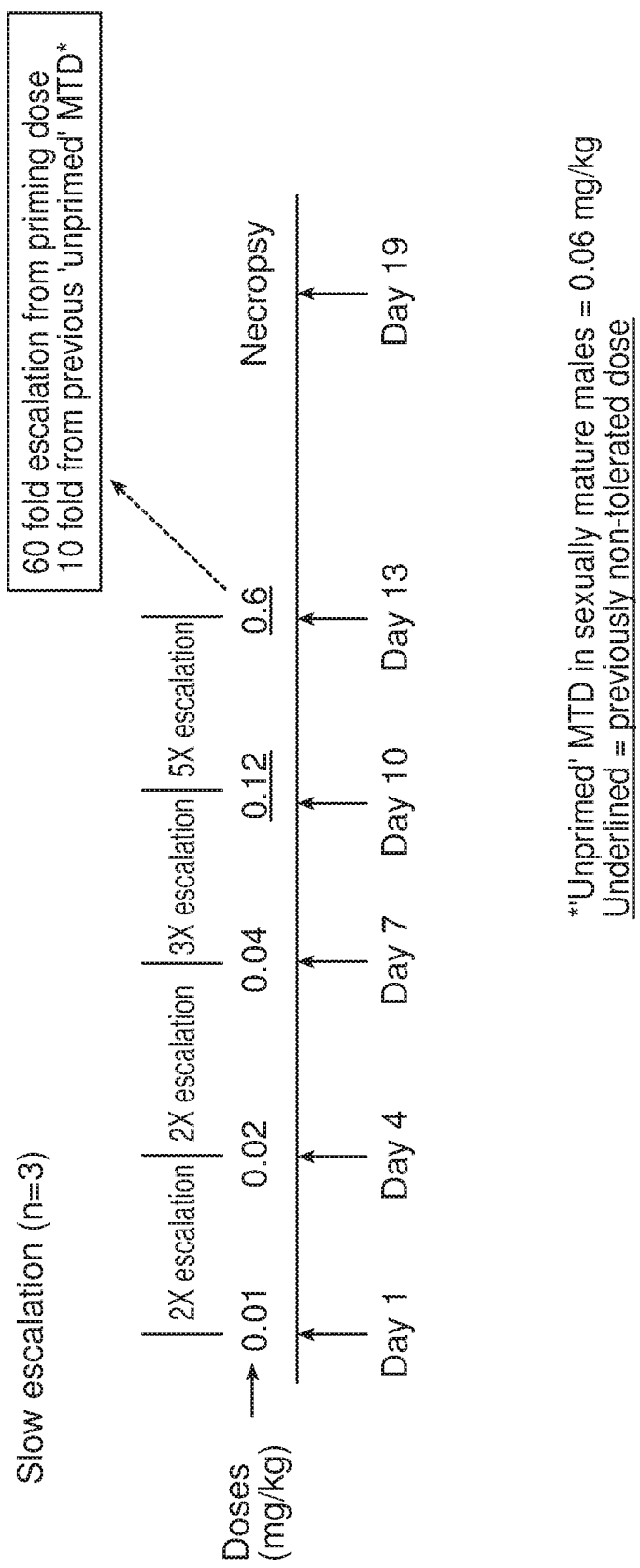

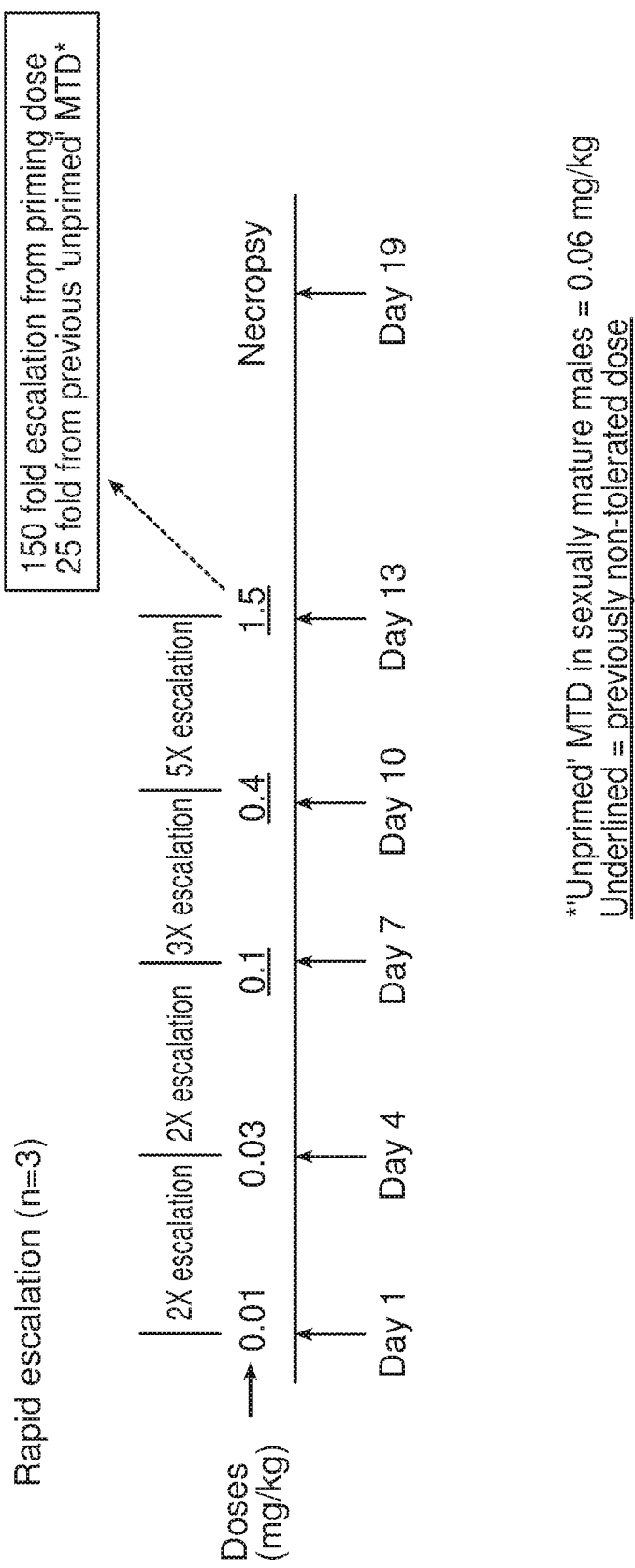

Abbreviations: CRS=cytokine release syndrome; PK/PD=pharmacokinetic/pharmacodynamic

SEQUENCE LISTING

```
<160> NUMBER OF SEQ ID NOS: 28

<210> SEQ ID NO 1
<211> LENGTH: 750
<212> TYPE: PRT
<213> ORGANISM: Homo sapiens
```

```
<400> SEQUENCE: 1

Met Trp Asn Leu Leu His Glu Thr Asp Ser Ala Val Ala Thr Ala Arg
1               5                   10                  15

Arg Pro Arg Trp Leu Cys Ala Gly Ala Leu Val Leu Ala Gly Gly Phe
            20                  25                  30

Phe Leu Leu Gly Phe Leu Phe Gly Trp Phe Ile Lys Ser Ser Asn Glu
                35                  40                  45

Ala Thr Asn Ile Thr Pro Lys His Asn Met Lys Ala Phe Leu Asp Glu
        50                  55                  60

Leu Lys Ala Glu Asn Ile Lys Lys Phe Leu Tyr Asn Phe Thr Gln Ile
65                  70                  75                  80

Pro His Leu Ala Gly Thr Glu Gln Asn Phe Gln Leu Ala Lys Gln Ile
                85                  90                  95

Gln Ser Gln Trp Lys Glu Phe Gly Leu Asp Ser Val Glu Leu Ala His
            100                 105                 110

Tyr Asp Val Leu Leu Ser Tyr Pro Asn Lys Thr His Pro Asn Tyr Ile
                115                 120                 125

Ser Ile Ile Asn Glu Asp Gly Asn Glu Ile Phe Asn Thr Ser Leu Phe
130                 135                 140

Glu Pro Pro Pro Pro Gly Tyr Glu Asn Val Ser Asp Ile Val Pro Pro
145                 150                 155                 160

Phe Ser Ala Phe Ser Pro Gln Gly Met Pro Glu Gly Asp Leu Val Tyr
                165                 170                 175

Val Asn Tyr Ala Arg Thr Glu Asp Phe Phe Lys Leu Glu Arg Asp Met
                180                 185                 190

Lys Ile Asn Cys Ser Gly Lys Ile Val Ile Ala Arg Tyr Gly Lys Val
            195                 200                 205

Phe Arg Gly Asn Lys Val Lys Asn Ala Gln Leu Ala Gly Ala Lys Gly
            210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Val Gln Arg Gly
                245                 250                 255

Asn Ile Leu Asn Leu Asn Gly Ala Gly Asp Pro Leu Thr Pro Gly Tyr
            260                 265                 270

Pro Ala Asn Glu Tyr Ala Tyr Arg Arg Gly Ile Ala Glu Ala Val Gly
            275                 280                 285

Leu Pro Ser Ile Pro Val His Pro Ile Gly Tyr Tyr Asp Ala Gln Lys
290                 295                 300

Leu Leu Glu Lys Met Gly Gly Ser Ala Pro Pro Asp Ser Ser Trp Arg
305                 310                 315                 320

Gly Ser Leu Lys Val Pro Tyr Asn Val Gly Pro Gly Phe Thr Gly Asn
                325                 330                 335

Phe Ser Thr Gln Lys Val Lys Met His Ile His Ser Thr Asn Glu Val
            340                 345                 350

Thr Arg Ile Tyr Asn Val Ile Gly Thr Leu Arg Gly Ala Val Glu Pro
            355                 360                 365

Asp Arg Tyr Val Ile Leu Gly Gly His Arg Asp Ser Trp Val Phe Gly
            370                 375                 380

Gly Ile Asp Pro Gln Ser Gly Ala Ala Val Val His Glu Ile Val Arg
385                 390                 395                 400

Ser Phe Gly Thr Leu Lys Lys Glu Gly Trp Arg Pro Arg Arg Thr Ile
                405                 410                 415
```

```
Leu Phe Ala Ser Trp Asp Ala Glu Glu Phe Gly Leu Gly Ser Thr
            420                 425                 430

Glu Trp Ala Glu Glu Asn Ser Arg Leu Leu Gln Glu Arg Gly Val Ala
        435                 440                 445

Tyr Ile Asn Ala Asp Ser Ser Ile Glu Gly Asn Tyr Thr Leu Arg Val
    450                 455                 460

Asp Cys Thr Pro Leu Met Tyr Ser Leu Val His Asn Leu Thr Lys Glu
465                 470                 475                 480

Leu Lys Ser Pro Asp Glu Gly Phe Gly Lys Ser Leu Tyr Glu Ser
                485                 490                 495

Trp Thr Lys Lys Ser Pro Ser Pro Glu Phe Ser Gly Met Pro Arg Ile
                500                 505                 510

Ser Lys Leu Gly Ser Gly Asn Asp Phe Glu Val Phe Phe Gln Arg Leu
            515                 520                 525

Gly Ile Ala Ser Gly Arg Ala Arg Tyr Thr Lys Asn Trp Glu Thr Asn
        530                 535                 540

Lys Phe Ser Gly Tyr Pro Leu Tyr His Ser Val Tyr Glu Thr Tyr Glu
545                 550                 555                 560

Leu Val Glu Lys Phe Tyr Asp Pro Met Phe Lys Tyr His Leu Thr Val
                565                 570                 575

Ala Gln Val Arg Gly Gly Met Val Phe Glu Leu Ala Asn Ser Ile Val
            580                 585                 590

Leu Pro Phe Asp Cys Arg Asp Tyr Ala Val Val Leu Arg Lys Tyr Ala
        595                 600                 605

Asp Lys Ile Tyr Ser Ile Ser Met Lys His Pro Gln Glu Met Lys Thr
610                 615                 620

Tyr Ser Val Ser Phe Asp Ser Leu Phe Ser Ala Val Lys Asn Phe Thr
625                 630                 635                 640

Glu Ile Ala Ser Lys Phe Ser Glu Arg Leu Gln Asp Phe Asp Lys Ser
                645                 650                 655

Asn Pro Ile Val Leu Arg Met Met Asn Asp Gln Leu Met Phe Leu Glu
            660                 665                 670

Arg Ala Phe Ile Asp Pro Leu Gly Leu Pro Asp Arg Pro Phe Tyr Arg
        675                 680                 685

His Val Ile Tyr Ala Pro Ser Ser His Asn Lys Tyr Ala Gly Glu Ser
    690                 695                 700

Phe Pro Gly Ile Tyr Asp Ala Leu Phe Asp Ile Glu Ser Lys Val Asp
705                 710                 715                 720

Pro Ser Lys Ala Trp Gly Glu Val Lys Arg Gln Ile Tyr Val Ala Ala
                725                 730                 735

Phe Thr Val Gln Ala Ala Glu Thr Leu Ser Glu Val Ala
            740                 745                 750

<210> SEQ ID NO 2
<211> LENGTH: 750
<212> TYPE: PRT
<213> ORGANISM: Pan troglodytes

<400> SEQUENCE: 2

Met Trp Asn Leu Leu His Glu Thr Asp Ser Ala Val Ala Thr Ala Arg
1               5                   10                  15

Arg Pro Arg Trp Leu Cys Ala Gly Ala Leu Val Leu Ala Gly Gly Phe
            20                  25                  30

Phe Leu Leu Gly Phe Leu Phe Gly Trp Phe Ile Lys Ser Ser Asn Glu
```

```
            35                  40                  45
Ala Thr Asn Ile Thr Pro Lys His Asn Met Lys Ala Phe Leu Asp Glu
 50                  55                  60

Leu Lys Ala Glu Asn Ile Lys Lys Phe Leu Tyr Asn Phe Thr Gln Ile
 65                  70                  75                  80

Pro His Leu Ala Gly Thr Glu Gln Asn Phe Gln Leu Ala Lys Gln Ile
                 85                  90                  95

Gln Ser Gln Trp Lys Glu Phe Gly Leu Asp Ser Val Glu Leu Ala His
            100                 105                 110

Tyr Asp Val Leu Leu Ser Tyr Pro Asn Lys Thr His Pro Asn Tyr Ile
            115                 120                 125

Ser Ile Ile Asn Glu Asp Gly Asn Glu Ile Phe Asn Thr Ser Leu Phe
            130                 135                 140

Glu Pro Pro Pro Gly Tyr Glu Asn Val Leu Asp Ile Val Pro Pro
145                 150                 155                 160

Phe Ser Ala Phe Ser Pro Gln Gly Met Pro Glu Gly Asp Leu Val Tyr
                165                 170                 175

Val Asn Tyr Ala Arg Thr Glu Asp Phe Phe Lys Leu Glu Arg Asp Met
                180                 185                 190

Lys Ile Asn Cys Ser Gly Lys Ile Val Ile Ala Arg Tyr Gly Lys Val
            195                 200                 205

Phe Arg Gly Asn Lys Val Lys Asn Ala Gln Leu Ala Gly Ala Lys Gly
            210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Val Gln Arg Gly
                245                 250                 255

Asn Ile Leu Asn Leu Asn Gly Ala Gly Asp Pro Leu Thr Pro Gly Tyr
            260                 265                 270

Pro Ala Asn Glu Tyr Ala Tyr Arg His Gly Ile Ala Glu Ala Val Gly
            275                 280                 285

Leu Pro Ser Ile Pro Val His Pro Ile Gly Tyr Tyr Asp Ala Gln Lys
            290                 295                 300

Leu Leu Glu Lys Met Gly Gly Ser Ala Pro Pro Asp Ser Ser Trp Arg
305                 310                 315                 320

Gly Ser Leu Lys Val Pro Tyr Asn Val Gly Pro Gly Phe Thr Gly Asn
                325                 330                 335

Phe Ser Thr Gln Lys Val Lys Met His Ile His Ser Thr Asn Glu Val
                340                 345                 350

Thr Arg Ile Tyr Asn Val Ile Gly Thr Leu Arg Gly Ala Val Glu Pro
            355                 360                 365

Asp Arg Tyr Val Ile Leu Gly Gly His Arg Asp Ser Trp Val Phe Gly
            370                 375                 380

Gly Ile Asp Pro Gln Ser Gly Ala Ala Val Val His Glu Ile Val Arg
385                 390                 395                 400

Ser Phe Gly Thr Leu Lys Lys Glu Gly Trp Arg Pro Arg Arg Thr Ile
                405                 410                 415

Leu Phe Ala Ser Trp Asp Ala Glu Glu Phe Gly Leu Leu Gly Ser Thr
            420                 425                 430

Glu Trp Ala Glu Glu Asn Ser Arg Leu Leu Gln Glu Arg Gly Val Ala
            435                 440                 445

Tyr Ile Asn Ala Asp Ser Ser Ile Glu Gly Asn Tyr Thr Leu Arg Val
            450                 455                 460
```

```
Asp Cys Thr Pro Leu Met Tyr Ser Leu Val Tyr Asn Leu Thr Lys Glu
465                 470                 475                 480

Leu Lys Ser Pro Asp Glu Gly Phe Glu Gly Lys Ser Leu Tyr Glu Ser
                485                 490                 495

Trp Thr Lys Lys Ser Pro Ser Pro Glu Phe Ser Gly Met Pro Arg Ile
            500                 505                 510

Ser Lys Leu Gly Ser Gly Asn Asp Phe Glu Val Phe Phe Gln Arg Leu
            515                 520                 525

Gly Ile Ala Ser Gly Arg Ala Arg Tyr Thr Lys Asn Trp Glu Thr Asn
530                 535                 540

Lys Phe Ser Gly Tyr Pro Leu Tyr His Ser Val Tyr Glu Thr Tyr Glu
545                 550                 555                 560

Leu Val Glu Lys Phe Tyr Asp Pro Met Phe Lys Tyr His Leu Thr Val
                565                 570                 575

Ala Gln Val Arg Gly Gly Met Val Phe Glu Leu Ala Asn Ser Ile Val
                580                 585                 590

Leu Pro Phe Asp Cys Arg Asp Tyr Ala Val Val Leu Arg Lys Tyr Ala
            595                 600                 605

Asp Lys Ile Tyr Asn Ile Ser Met Lys His Pro Gln Glu Met Lys Thr
610                 615                 620

Tyr Ser Val Ser Phe Asp Ser Leu Phe Ser Ala Val Lys Asn Phe Thr
625                 630                 635                 640

Glu Ile Ala Ser Lys Phe Thr Glu Arg Leu Gln Asp Phe Asp Lys Ser
                645                 650                 655

Asn Pro Ile Leu Leu Arg Met Met Asn Asp Gln Leu Met Phe Leu Glu
            660                 665                 670

Arg Ala Phe Ile Asp Pro Leu Gly Leu Pro Asp Arg Pro Phe Tyr Arg
            675                 680                 685

His Val Ile Tyr Ala Pro Ser Ser His Asn Lys Tyr Ala Gly Glu Ser
            690                 695                 700

Phe Pro Gly Ile Tyr Asp Ala Leu Phe Asp Ile Glu Ser Lys Val Asp
705                 710                 715                 720

Pro Ser Lys Ala Trp Gly Asp Val Lys Arg Gln Ile Ser Val Ala Ala
                725                 730                 735

Phe Thr Val Gln Ala Ala Glu Thr Leu Ser Glu Val Ala
                740                 745                 750

<210> SEQ ID NO 3
<211> LENGTH: 750
<212> TYPE: PRT
<213> ORGANISM: Macaca fascicularis

<400> SEQUENCE: 3

Met Trp Asn Leu Leu His Glu Thr Asp Ser Ala Val Ala Thr Ala Arg
1               5                   10                  15

Arg Pro Arg Trp Leu Cys Ala Gly Ala Leu Val Leu Ala Gly Gly Phe
                20                  25                  30

Phe Leu Leu Gly Phe Leu Phe Gly Trp Phe Ile Lys Ser Ser Ser Glu
            35                  40                  45

Ala Thr Asn Ile Thr Pro Lys His Asn Met Lys Ala Phe Leu Asp Glu
        50                  55                  60

Leu Lys Ala Glu Asn Ile Lys Lys Phe Leu His Asn Phe Thr Gln Ile
65                  70                  75                  80

Pro His Leu Ala Gly Thr Glu Gln Asn Phe Gln Leu Ala Lys Gln Ile
```

```
                  85                  90                  95

Gln Ser Gln Trp Lys Glu Phe Gly Leu Asp Ser Val Glu Leu Thr His
            100                 105                 110

Tyr Asp Val Leu Leu Ser Tyr Pro Asn Lys Thr His Pro Asn Tyr Ile
            115                 120                 125

Ser Ile Ile Asn Glu Asp Gly Asn Glu Ile Phe Asn Thr Ser Leu Phe
130                 135                 140

Glu Pro Pro Pro Ala Gly Tyr Glu Asn Val Ser Asp Ile Val Pro Pro
145                 150                 155                 160

Phe Ser Ala Phe Ser Pro Gln Gly Met Pro Glu Gly Asp Leu Val Tyr
                165                 170                 175

Val Asn Tyr Ala Arg Thr Glu Asp Phe Phe Lys Leu Glu Arg Asp Met
                180                 185                 190

Lys Ile Asn Cys Ser Gly Lys Ile Val Ile Ala Arg Tyr Gly Lys Val
                195                 200                 205

Phe Arg Gly Asn Lys Val Lys Asn Ala Gln Leu Ala Gly Ala Thr Gly
            210                 215                 220

Val Ile Leu Tyr Ser Asp Pro Asp Tyr Phe Ala Pro Gly Val Lys
225                 230                 235                 240

Ser Tyr Pro Asp Gly Trp Asn Leu Pro Gly Gly Val Gln Arg Gly
                245                 250                 255

Asn Ile Leu Asn Leu Asn Gly Ala Gly Asp Pro Leu Thr Pro Gly Tyr
                260                 265                 270

Pro Ala Asn Glu Tyr Ala Tyr Arg Arg Gly Met Ala Glu Ala Val Gly
            275                 280                 285

Leu Pro Ser Ile Pro Val His Pro Ile Gly Tyr Tyr Asp Ala Gln Lys
290                 295                 300

Leu Leu Glu Lys Met Gly Gly Ser Ala Ser Pro Asp Ser Ser Trp Arg
305                 310                 315                 320

Gly Ser Leu Lys Val Pro Tyr Asn Val Gly Pro Gly Phe Thr Gly Asn
                325                 330                 335

Phe Ser Thr Gln Lys Val Lys Met His Ile His Ser Thr Ser Glu Val
                340                 345                 350

Thr Arg Ile Tyr Asn Val Ile Gly Thr Leu Arg Gly Ala Val Glu Pro
            355                 360                 365

Asp Arg Tyr Val Ile Leu Gly Gly His Arg Asp Ser Trp Val Phe Gly
370                 375                 380

Gly Ile Asp Pro Gln Ser Gly Ala Ala Val His Glu Ile Val Arg
385                 390                 395                 400

Ser Phe Gly Met Leu Lys Lys Glu Gly Trp Arg Pro Arg Arg Thr Ile
                405                 410                 415

Leu Phe Ala Ser Trp Asp Ala Glu Glu Phe Gly Leu Leu Gly Ser Thr
                420                 425                 430

Glu Trp Ala Glu Glu Asn Ser Arg Leu Leu Gln Glu Arg Gly Val Ala
            435                 440                 445

Tyr Ile Asn Ala Asp Ser Ser Ile Glu Gly Asn Tyr Thr Leu Arg Val
450                 455                 460

Asp Cys Thr Pro Leu Met Tyr Ser Leu Val Tyr Asn Leu Thr Lys Glu
465                 470                 475                 480

Leu Glu Ser Pro Asp Glu Gly Phe Glu Gly Lys Ser Leu Tyr Glu Ser
                485                 490                 495

Trp Thr Lys Lys Ser Pro Ser Pro Glu Phe Ser Gly Met Pro Arg Ile
            500                 505                 510
```

```
Ser Lys Leu Gly Ser Gly Asn Asp Phe Glu Val Phe Gln Arg Leu
        515                 520                 525

Gly Ile Ala Ser Gly Arg Ala Arg Tyr Thr Lys Asn Trp Glu Thr Asn
530                 535                 540

Lys Phe Ser Ser Tyr Pro Leu Tyr His Ser Val Tyr Glu Thr Tyr Glu
545                 550                 555                 560

Leu Val Glu Lys Phe Tyr Asp Pro Met Phe Lys Tyr His Leu Thr Val
                565                 570                 575

Ala Gln Val Arg Gly Gly Met Val Phe Glu Leu Ala Asn Ser Val Val
                580                 585                 590

Leu Pro Phe Asp Cys Arg Asp Tyr Ala Val Val Leu Arg Lys Tyr Ala
            595                 600                 605

Asp Lys Ile Tyr Asn Ile Ser Met Lys His Pro Gln Glu Met Lys Thr
            610                 615                 620

Tyr Ser Val Ser Phe Asp Ser Leu Phe Ser Ala Val Lys Asn Phe Thr
625                 630                 635                 640

Glu Ile Ala Ser Lys Phe Ser Glu Arg Leu Arg Asp Phe Asp Lys Ser
                645                 650                 655

Asn Pro Ile Leu Leu Arg Met Met Asn Asp Gln Leu Met Phe Leu Glu
            660                 665                 670

Arg Ala Phe Ile Asp Pro Leu Gly Leu Pro Asp Arg Pro Phe Tyr Arg
            675                 680                 685

His Val Ile Tyr Ala Pro Ser Ser His Asn Lys Tyr Ala Gly Glu Ser
            690                 695                 700

Phe Pro Gly Ile Tyr Asp Ala Leu Phe Asp Ile Glu Ser Lys Val Asp
705                 710                 715                 720

Pro Ser Gln Ala Trp Gly Glu Val Lys Arg Gln Ile Ser Ile Ala Thr
                725                 730                 735

Phe Thr Val Gln Ala Ala Ala Glu Thr Leu Ser Glu Val Ala
                740                 745                 750

<210> SEQ ID NO 4
<211> LENGTH: 207
<212> TYPE: PRT
<213> ORGANISM: Homo sapiens

<400> SEQUENCE: 4

Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
                20                  25                  30

Gln Thr Pro Tyr Lys Val Ser Ile Ser Gly Thr Thr Val Ile Leu Thr
                35                  40                  45

Cys Pro Gln Tyr Pro Gly Ser Glu Ile Leu Trp Gln His Asn Asp Lys
            50                  55                  60

Asn Ile Gly Gly Asp Glu Asp Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
                100                 105                 110

Tyr Leu Arg Ala Arg Val Cys Glu Asn Cys Met Glu Met Asp Val Met
            115                 120                 125

Ser Val Ala Thr Ile Val Ile Val Asp Ile Cys Ile Thr Gly Gly Leu
```

```
                130                 135                 140
Leu Leu Leu Val Tyr Tyr Trp Ser Lys Asn Arg Lys Ala Lys Ala Lys
145                 150                 155                 160

Pro Val Thr Arg Gly Ala Gly Gly Arg Gln Arg Gly Gln Asn
                165                 170                 175

Lys Glu Arg Pro Pro Val Pro Asn Pro Asp Tyr Glu Pro Ile Arg
                180                 185                 190

Lys Gly Gln Arg Asp Leu Tyr Ser Gly Leu Asn Gln Arg Ile
                195                 200                 205

<210> SEQ ID NO 5
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Lys Ser Asp
                20                  25                  30

Ala Met His Trp Val Arg Gln Ala Pro Gly Lys Gly Leu Glu Trp Val
            35                  40                  45

Ser Glu Ile Ser Gly Ser Gly Gly Tyr Thr Asn Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Tyr Asp Ser Ser Leu Tyr Val Gly Asp Tyr Phe Asp
                100                 105                 110

Tyr Trp Gly Gln Gly Thr Leu Val Thr Val Ser Ser
            115                 120

<210> SEQ ID NO 6
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gln Gly Thr Lys Val Glu Ile Lys
            100                 105
```

<210> SEQ ID NO 7
<211> LENGTH: 451
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 7

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Lys Ser Asp
            20                  25                  30

Ala Met His Trp Val Arg Gln Ala Pro Gly Lys Gly Leu Glu Trp Val
        35                  40                  45

Ser Glu Ile Ser Gly Ser Gly Gly Tyr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Tyr Asp Ser Ser Leu Tyr Val Gly Asp Tyr Phe Asp
            100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
        195                 200                 205

Val Asp His Lys Pro Ser Asn Thr Lys Val Asp Lys Arg Val Glu Ser
    210                 215                 220

Lys Tyr Gly Pro Pro Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

```
Tyr Thr Leu Pro Pro Ser Gln Glu Glu Met Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
                420                 425                 430

His Glu Ala Leu His Asn His Tyr Thr Gln Lys Ser Leu Ser Leu Ser
            435                 440                 445

Leu Gly Lys
    450

<210> SEQ ID NO 8
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 9
<211> LENGTH: 5
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 9

Ser Asp Ala Met His
1               5

<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Glu Ile Ser Gly Ser Gly Gly Tyr Thr Asn Tyr Ala Asp Ser Val Lys
1               5                  10                  15

Gly

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Asp Ser Tyr Asp Ser Ser Leu Tyr Val Gly Asp Tyr Phe Asp Tyr
1               5                  10                  15

<210> SEQ ID NO 12
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Arg Ala Ser Gln Ser Val Ser Ser Tyr Leu Ala
1               5                  10

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Asp Ala Ser Asn Arg Ala Thr
1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gln Gln Arg Ser Asn Trp Pro Leu Thr
```

-continued

<210> SEQ ID NO 15
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Ala
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 16
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Thr Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105

<210> SEQ ID NO 17
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Ala
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Leu Leu Tyr Ser Lys Leu Thr
                405                 410                 415
```

```
Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly Lys
    450

<210> SEQ ID NO 18
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gln Thr Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Thr Tyr Ala Met Asn
1               5

<210> SEQ ID NO 20
<211> LENGTH: 17
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Arg Ile Arg Ser Lys Tyr Asn Asn Tyr Ala Thr Tyr Tyr Ala Ala Ser
1               5                   10                  15
Val

<210> SEQ ID NO 21
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

His Gly Asn Phe Gly Asn Ser Tyr Val Ser Trp Phe Ala Tyr
1               5                   10

<210> SEQ ID NO 22
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Arg Ser Ser Thr Gly Ala Val Thr Thr Ser Asn Tyr Ala Asn
1               5                   10

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Thr Asn Lys Arg Ala Pro
1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ala Leu Trp Tyr Ser Asn Leu Trp Val
1               5

<210> SEQ ID NO 25
<211> LENGTH: 1410
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
```

| | |
|---|---|
| atggcttggg tgtggacctt gctattcctg atggcagctg cccaaagtat acaggccgag | 60 |
| gttcagctgc tggaatctgg cggaggattg gttcagcctg gcggctctct gagactgtct | 120 |
| tgtgccgctt ctggcttcac cttcaagtcc gacgctatgc actgggtccg acaggcccct | 180 |
| ggaaaaggac tggaatgggt gtccgagatc tctggctctg cggctacac caactacgcc | 240 |
| gactccatga agtcccggtt caccatctct cgggacaact ccaagaacac cctgtacctg | 300 |
| cagatgaact ccctgagagc cgaggacacc gccgtgtact actgcgccag agactcctac | 360 |
| gactccagcc tgtacgtggg cgactacttc gattattggg gccagggcac cctggtcacc | 420 |
| gtttcttctg cttccaccaa gggcccatcc gtcttccccc tggcgccctg ctccaggagc | 480 |
| acctccgaga gcacagccgc cctgggctgc ctggtcaagg actacttccc cgaaccggtg | 540 |
| acggtgtcgt ggaactcagg cgccctgacc agcggcgtgc acaccttccc ggctgtccta | 600 |
| cagtcctcag gactctactc cctcagcagc gtggtgaccg tgcctccag cagcttgggc | 660 |
| acgaaaacct acacctgcaa cgtagatcac aagcccagca acaccaaggt ggacaagaga | 720 |
| gttgagtcca aatatggtcc cccatgccca ccatgcccag cacctgaggc cgccggggga | 780 |
| ccatcagtct tcctgttccc cccaaaaccc aaggacactc tcatgatctc ccggaccct | 840 |
| gaggtcacgt gcgtggtggt ggacgtgagc caggaagacc ccgaggtcca gttcaactgg | 900 |
| tacgtggatg gcgtggaggt gcataatgcc aagacaaagc cgcggagga gcagttcaac | 960 |
| agcacgtacc gtgtggtcag cgtcctcacc gtcctgcacc aggactggct gaacggcaag | 1020 |
| gagtacaagt gcaaggtctc caacaaaggc ctcccgtcct ccatcgagaa aaccatctcc | 1080 |
| aaagccaaag gcagccccg agagccacag gtgtacaccc tgcccccatc ccaggaggag | 1140 |
| atgaccaaga accaggtcag cctgacctgc ctggtcaaag gcttctaccc cagcgacatc | 1200 |
| gccgtggagt gggagagcaa tgggcagccg gagaacaact acaagaccac gcctcccgtg | 1260 |
| ctggactccg acggctcctt cttcctctac agcaggctaa ccgtggacaa gagcaggtgg | 1320 |
| caggagggga atgtcttctc atgctccgtg atgcatgagg ctctgcacaa ccactacaca | 1380 |
| cagaagagcc tctccctgtc tctgggtaaa | 1410 |

<210> SEQ ID NO 26
<211> LENGTH: 699
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 26

| | |
|---|---|
| atggcctggg tgtggaccct gctgttcctg atggccgccg cccagagcat ccaggccgag | 60 |
| atcgtgctga cccagagccc cgccaccctg agcctgagcc ccggcgagcg ggccaccctg | 120 |
| agctgccggg ccagccagag cgtgagcagc tacctggcct ggtaccagca gaagcccggc | 180 |
| caggccccc ggctgctgat ctacgacgcc agcaaccggg ccaccggcat ccccgcccgg | 240 |
| ttcagcggca gcggcagcgg caccgacttc accctgacca tcagcagcct ggagcccgag | 300 |
| gacttcgccg tgtactactg ccagcagcgg agcaactggc ccctgacctt cggccagggc | 360 |
| accaaggtgg agatcaagcg tacggtggct gcaccatctg tcttcatctt cccgccatct | 420 |
| gatgagcagt tgaaatctgg aactgcctct gttgtgtgcc tgctgaataa cttctatccc | 480 |
| agagaggcca aagtacagtg gaaggtggat aacgccctcc aatcgggtaa ctcccaggag | 540 |
| agtgtcacag agcaggacag caaggacagc acctacagcc tcagcagcac cctgacgctg | 600 |

```
agcaaagcag actacgagaa acacaaagtc tacgcctgcg aagtcaccca tcagggcctg    660
agctcgcccg tcacaaagag cttcaacagg ggagagtgt                            699
```

<210> SEQ ID NO 27
<211> LENGTH: 1356
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27

```
gaagtgcagc tggtggaatc tggcggcgga ctggtgcagc ctggcggatc tctgagactg     60
agctgtgccg ccagcggctt caccttcaac acctacgcca tgaactgggt gcgccaggcc    120
cctggcaaag gcctggaatg ggtggcccgg atcagaagca agtacaacaa ttacgccacc    180
tactacgccg cctccgtgaa gggcagattc accatcagcc gggacgacag caagaacagc    240
ctgtacctgc agatgaactc cctgaaaacc gaggacaccg ccgtgtacta ctgcgccaga    300
cacggcaact tcggcaacag ctatgtgtct tggtttgcct actggggcca gggcaccctc    360
gtgaccgtgt catctgcttc caccaagggc ccatccgtct tccccctggc gccctgctcc    420
aggagcacct ccgagagcac agccgccctg ggctgcctgg tcaaggacta cttccccgaa    480
ccggtgacgg tgtcgtggaa ctcaggcgcc ctgaccagcg gcgtgcacac cttcccggct    540
gtcctacagt cctcaggact ctactccctc agcagcgtgg tgaccgtgcc ctccagcagc    600
ttgggcacga aacctacac ctgcaacgta gatcacaagc ccagcaacac caaggtggac    660
aagagagttg agtccaaata tggtccccca tgcccaccat gcccagcacc tgaggccgcc    720
gggggaccat cagtcttcct gttccccccca aacccaagg acactctcat gatctcccgg    780
acccctgagg tcacgtgcgt ggtggtggac gtgagccagg aagacccga ggtccagttc    840 aactggtacg tggatggcgt ggaggtgcat aatgccaaga caaagccgcg ggaggagcag    900
ttcaacagca cgtaccgtgt ggtcagcgtc ctcaccgtcc tgcaccagga ctggctgaac    960
ggcaaggagt acaagtgcaa ggtctccaac aaaggcctcc cgtcctccat cgagaaaacc   1020
atctccaaag ccaaagggca gccccgagag ccacaggtgt acaccctgcc cccatcccag   1080
gaggagatga ccaagaacca ggtcagcctg acctgcctgg tcaaaggctt ctaccccagc   1140
gacatcgccg tggagtggga gagcaatggg cagccggaga caactacaa gaccacgcct   1200 cccgtgctgg actccgacgg ctccttcctc tctacagca agctaaccgt ggacaagagc   1260
aggtggcagg aggggaatgt cttctcatgc tccgtgatgc atgaggctct gcacaaccac   1320
tacacacaga gagcctctc cctgtctctg ggtaaa                              1356
```

<210> SEQ ID NO 28
<211> LENGTH: 645
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28

```
cagaccgtcg tgacccagga acctagcctg accgtgtctc ctggcggcac cgtgaccctg     60
acctgcagat cttctacagg cgccgtgacc accagcaact acgccaactg ggtgcagcag    120
aagccaggcc aggctcccag aggactgatc ggcggcacca caagagagc ccctggcacc    180
```

```
                                                       -continued cctgccagat tcagcggatc tctgctggga ggaaaggccg ccctgacact gtctggcgtg      240
cagcctgaag atgaggccga gtactactgc gccctgtggt acagcaacct gtgggtgttc      300
ggcggaggca ccaagctgac agtgctgggt cagcccaagg ctgcacccag tgtcactctg      360
ttcccgccct cctctgagga gcttcaagcc aacaaggcca cactggtgtg tctcataagt      420
gacttctacc cgggagccgt gacagtggcc tggaaggccg atagcagccc cgtcaaggcg      480
ggagtggaga ccaccacacc ctccaaacaa agcaacaaca agtacgcggc cagcagctat      540
ctgagcctga cgcctgagca gtggaagtcc cacagaagct acagctgcca ggtcacgcat      600
gaagggagca ccgtggagaa gacagtggcc cctacagaat gttca                     645
```

METHODS OF TREATING PROSTATE CANCER WITH AN ANTI-PSMA/CD3 ANTIBODY

SEQUENCE LISTING

The instant application contains a Sequence Listing which has been submitted electronically in ASCII format and is hereby incorporated by reference in its entirety. Said ASCII copy, created on Feb. 26, 2020, is named JBI6080USPSP1_SL.txt and is 47,009 bytes in size.

FIELD OF THE INVENTION

The invention relates to methods of providing a treatment for prostate cancer, including castrate resistant prostate cancer, metastatic castration resistant prostate cancer, castration sensitive prostate cancer, and non-metastatic castration resistant prostate cancer by administration of an anti-PSMA/CD3 antibody.

BACKGROUND OF THE INVENTION

Prostate cancer is the second most frequently diagnosed cancer and the sixth leading cause of cancer death in males, accounting for 14% (903,500) of the total new cancer cases and 6% (258,400) of the total cancer deaths in males worldwide. Metastatic prostate cancer is the second leading cause of cancer death in men in the United States. The course of prostate cancer from diagnosis to death is best categorized as a series of clinical stages based on the extent of disease, hormonal status, and absence or presence of detectable metastases: localized disease, rising levels of prostate-specific antigen (PSA) after radiation therapy or surgery with no detectable metastases, and clinical metastases in the non-castrate or castrate stage. Although surgery, radiation, or a combination of both can be curative for patients with localized disease, a significant proportion of these patients have recurrent disease as evidenced by a rising level of PSA, which can lead to the development of metastases, especially in the high-risk group—a transition to the lethal stage of the disease.

Prostate specific membrane antigen (PSMA), is a type II membrane protein that is highly expressed in prostatic intraepithelial neoplasia (PIN), a condition in which some prostate cells have begun to look and behave abnormally, and in primary and metastatic prostate cancers (Bostwick D G, Pacelli A, Blute M, Roche P, Murphy G P. Prostate specific membrane antigen expression in prostatic intraepithelial neoplasia and adenocarcinoma: A study of 184 cases. Cancer 1998; 82 (11):2256-2261]. Expression of PSMA in cancer tissues correlates with the stage of disease and Gleason score (Kawakami M, Nakayama J. Enhanced expression of prostate-specific membrane antigen gene in prostate cancer as revealed by in situ hybridization. Cancer Res 1997; 57(12):2321-2324). PSMA expression is also higher in prostate cancer cells from hormone-refractory patients (Wright G L Jr, Grob B M, Haley C, Grossman K, Newhall K, Petrylak D, Troyer J, Konchuba A, Schellhammer P F, Moriarty R. Upregulation of prostate-specific membrane antigen after androgen-deprivation therapy. Urology 1996; 48(2):326-334) and increased PSMA expression has been shown to be an independent marker of disease recurrence (Mitsiades C S, Lembessis P, Sourla A, Milathianakis C, Tsintavis A, Koutsilieris M. Molecular staging by RT-pCR analysis for PSA and PSMA in peripheral blood and bone marrow samples is an independent predictor of time to biochemical failure following radical prostatectomy for clinically localized prostate cancer. Clin Exp Metastasis 2004; 21(6):495-505). High-level PSMA expression is correlated with early prostate-specific antigen (PSA) recurrence in surgically treated prostate cancer. PSMA expression levels correlate with the aggressiveness of the disease, and thereby strongly support PSMA as an excellent target for prostate cancer characterization and subsequent therapy.

Current treatments for prostate cancer include surgery, radiation and hormone therapies. When prostate cancers grow despite the lowering of testosterone levels by hormone therapy, treatment options are limited. Typically, the cancer vaccine sipuleucel-T, a radiopharmaceutical agent (such as radium-223 chloride), secondary hormone therapies (such as abiraterone acetate plus prednisone/prednisolone, enzalutamide, or apalutamide), and/or chemotherapies (docetaxel and cabazitaxel) are added to the hormonal therapy in sequence. While each of these treatments can delay growth of the cancer for several months and palliate symptoms produced by the disease, the disease ultimately becomes resistant to them. This underscores the need for more improved treatment and effective therapies for PSMA-expressing advanced prostate cancer.

SUMMARY OF THE INVENTION

The general and preferred embodiments are defined, respectively, by the independent and dependent claims appended hereto, which for the sake of brevity are incorporated by reference herein. Other preferred embodiments, features, and advantages of the various aspects of the invention will become apparent from the detailed description below taken in conjunction with the appended drawing figures.

The present invention is directed to methods of treating prostate cancer including metastatic castration resistant prostate cancer (mCRPC), by administering a safe amount of anti-PSMAxCD3 antibody to a male human having prostate cancer.

In certain embodiments, the present invention provides a method of treating prostate cancer in a patient having prostate cancer, the method comprising, consisting of and/or consisting essentially of administering an anti-PSMAxCD3 antibody fragment to the patient in a safe amount, wherein the anti-PSMAxCD3 antibody comprises, consists of and/or consists essentially of a first binding domain that specifically binds PSMA and a second binding domain that specifically binds CD3, wherein the first binding domain comprises a heavy chain (HC) of SEQ ID NO:7 and a light chain (LC) of SEQ ID NO:8 and the second binding domain comprises a heavy chain (HC) of SEQ ID NO:17 and a light chain (LC) of SEQ ID NO:18.

In another embodiment, the present invention provides a method of treating prostate cancer in a patient having prostate cancer, the method comprising, consisting of and/or consisting essentially of administering an anti-PSMAxCD3 antibody fragment to the patient in a safe amount, wherein the anti-PSMAxCD3 antibody comprises a first binding domain that specifically binds PSMA and a second binding domain that specifically binds CD3, wherein the first binding domain comprises a heavy chain (HC) of SEQ ID NO:7 and a light chain (LC) of SEQ ID NO:8 and the second binding domain comprises a heavy chain (HC) of SEQ ID NO:17 and a light chain (LC) of SEQ ID NO:18, wherein the patient has metastatic prostate cancer.

In another embodiment, the present invention provides a method of treating prostate cancer in a patient having prostate cancer, the method comprising, consisting of and/or consisting essentially of administering an anti-PSMAxCD3 antibody fragment to the patient in a safe amount, wherein the anti-PSMAxCD3 antibody comprises a first binding domain that specifically binds PSMA and a second binding domain that specifically binds CD3, wherein the first binding domain comprises a heavy chain (HC) of SEQ ID NO:7 and a light chain (LC) of SEQ ID NO:8 and the second binding domain comprises a heavy chain (HC) of SEQ ID NO:17 and a light chain (LC) of SEQ ID NO:18, wherein the prostate cancer is metastatic castration-resistant prostate cancer (mCRPC).

In another embodiment, the present invention provides a method of treating prostate cancer in a patient having prostate cancer, the method comprising, consisting of and/or consisting essentially of administering an anti-PSMAxCD3 antibody fragment to the patient in a safe amount, wherein the anti-PSMAxCD3 antibody comprises a first binding domain that specifically binds PSMA and a second binding domain that specifically binds CD3, wherein the first binding domain comprises a heavy chain (HC) of SEQ ID NO:7 and a light chain (LC) of SEQ ID NO:8 and the second binding domain comprises a heavy chain (HC) of SEQ ID NO:17 and a light chain (LC) of SEQ ID NO:18, wherein said patient has relapsed disease despite receiving androgen receptor (AR)-targeted therapy.

In another embodiment, the present invention provides a method of treating prostate cancer in a patient having prostate cancer, the method comprising, consisting of and/or consisting essentially of administering an anti-PSMAxCD3 antibody fragment to the patient, wherein the anti-PSMAxCD3 antibody comprises a first binding domain that specifically binds PSMA and a second binding domain that specifically binds CD3, wherein the first binding domain comprises a heavy chain (HC) of SEQ ID NO:7 and a light chain (LC) of SEQ ID NO:8 and the second binding domain comprises a heavy chain (HC) of SEQ ID NO:17 and a light chain (LC) of SEQ ID NO:18, wherein the patient has metastatic castration-resistant prostate cancer and the patient has relapsed disease despite receiving androgen receptor (AR)-targeted therapy, and wherein the anti-PSMAxCD3 antibody is administered to the patient intravenously (IV) at a dose of about 0.1 ug/kg.

In another embodiments, the present invention provides a method of treating prostate cancer in a patient having prostate cancer, the method comprising, consisting of and/or consisting essentially of administering an anti-PSMAxCD3 antibody fragment to the patient, wherein the anti-PSMAxCD3 antibody comprises a first binding domain that specifically binds PSMA and a second binding domain that specifically binds CD3, wherein the first binding domain comprises a heavy chain (HC) of SEQ ID NO:7 and a light chain (LC) of SEQ ID NO:8 and the second binding domain comprises a heavy chain (HC) of SEQ ID NO:17 and a light chain (LC) of SEQ ID NO:18, wherein the prostate cancer is metastatic castration-resistant prostate cancer, the patient has relapsed disease despite receiving androgen receptor (AR)-targeted therapy, and wherein the anti-PSMAxCD3 antibody is administered to the patient intravenously (IV) at an initial dose of about 0.1 ug/kg at week 1 followed by a dose escalation regiment comprising about 0.3 μg/kg at week 2, about 1 μg/kg at week 3, about 3 μg/kg at week 4, about 10 μg/kg at week 5, about 20 μg/kg at week 6, about 40 μg/kg at week 7, 80 μg/kg at week 8, and about 120 μg/kg at week 9.

In another embodiment, the present invention provides a method of treating prostate cancer in a patient, the method comprising, consisting of and/or consisting essentially of administering an anti-PSMAxCD3 antibody fragment to the patient, wherein the anti-PSMAxCD3 antibody comprises a first binding domain that specifically binds PSMA and a second binding domain that specifically binds CD3, wherein the first binding domain comprises a heavy chain (HC) of SEQ ID NO:7 and a light chain (LC) of SEQ ID NO:8 and the second binding domain comprises a heavy chain (HC) of SEQ ID NO:17 and a light chain (LC) of SEQ ID NO:18, wherein said patient has metastatic castration-resistant prostate cancer and said patient has relapsed disease despite receiving androgen receptor (AR)-targeted therapy, and wherein the anti-PSMAxCD3 antibody is administered to the patient intravenously (IV) at a dose escalation comprising an initial dose of about 0.1 μg/kg at week 1 followed by a dose escalation regiment consisting of about 0.3 μg/kg at week 2, about 1 μg/kg at week 3, about 3 μg/kg at week 4, about 10 μg/kg at week 5, about 20 μg/kg at week 6, about 40 μg/kg at week 7, about 80 μg/kg at week 8, and about 120 μg/kg at week 9.

In another embodiment, the present invention provides a method of treating prostate cancer in a patient, the method comprising, consisting of and/or consisting essentially of administering an anti-PSMAxCD3 antibody fragment to the patient, wherein the anti-PSMAxCD3 antibody comprises a first binding domain that specifically binds PSMA and a second binding domain that specifically binds CD3, wherein the first binding domain comprises a heavy chain (HC) of SEQ ID NO:7 and a light chain (LC) of SEQ ID NO:8 and the second binding domain comprises a heavy chain (HC) of SEQ ID NO:17 and a light chain (LC) of SEQ ID NO:18, wherein the patient has metastatic castration-resistant prostate cancer and the patient has relapsed disease despite receiving androgen receptor (AR)-targeted therapy, and wherein the anti-PSMAxCD3 antibody is administered to the patient intravenously (IV) at an initial dose of about 0.1 μg/kg at week 1 followed by a dose escalation regiment consisting of about 0.3 μg/kg at week 2, about 1 μg/kg at week 3, about 3 μg/kg at week 4, about 10 μg/kg at week 5, about 20 μg/kg at week 6, about 40 μg/kg at week 7, about 80 μg/kg at week 8, and about 120 μg/kg at week 9.

In some embodiments, the present invention provides a pharmaceutical composition comprising, consisting of and/or consisting essentially of an antigen binding protein of SEQ ID NOs: 7, 8, 17 and 18 for use in the treatment of prostate cancer in patient, wherein the composition is administered to the patient at an initial dose of about 0.1 μg/kg at week 1, followed by a dose escalation regiment consisting of about 0.3 μg/kg at week 2, about 1 μg/kg at week 3, about 3 μg/kg at week 4, about 10 μg/kg at week 5, about 20 μg/kg at week 6, about 40 μg/kg at week 7, about 80 μg/kg at week 8, and about 120 μg/kg at week 9.

In another embodiment, the present invention provides a pharmaceutical composition comprising, consisting of and/or consisting essentially of an antigen binding protein of SEQ ID NOs: 7, 8, 17 and 18 for use in the treatment of prostate cancer in a patient, wherein the composition is administered to the patient at an initial dose of 0.1 μg/kg at week 1, followed by a dose escalation regiment consisting of about 0.3 μg/kg at week 2, about 1 μg/kg at week 3, about 3 μg/kg at week 4, about 10 μg/kg at week 5, about 20 μg/kg at week 6, about 40 μg/kg at week 7, about 80 μg/kg at week 8, and about 120 μg/kg at week 9, and wherein the prostate cancer is castration resistant prostate cancer.

In another embodiment, the present invention provides a pharmaceutical composition comprising, consisting of and/ or consisting essentially of an antigen binding protein of SEQ ID NOs: 7, 8, 17 and 18 for use in the treatment of prostate cancer in a patient, wherein the composition is administered to the patient at an initial dose of about 0.1 µg/kg at week 1, followed by a dose escalation regiment consisting of about 0.3 µg/kg at week 2, about 1 µg/kg at week 3, about 3 µg/kg at week 4, about 10 µg/kg at week 5, about 20 µg/kg at week 6, about 40 µg/kg at week 7, about 80 µg/kg at week 8, and about 120 µg/kg at week 9, and wherein the prostate cancer is metastatic castration-resistant prostate cancer (mCRPC).

BRIEF DESCRIPTION OF THE FIGURES

FIG. 10A shows slow escalation scheme used in toxicology studies.

FIG. 10B shows rapid escalation scheme used in toxicology studies.

DETAILED DESCRIPTION OF THE INVENTION

Figure 1:
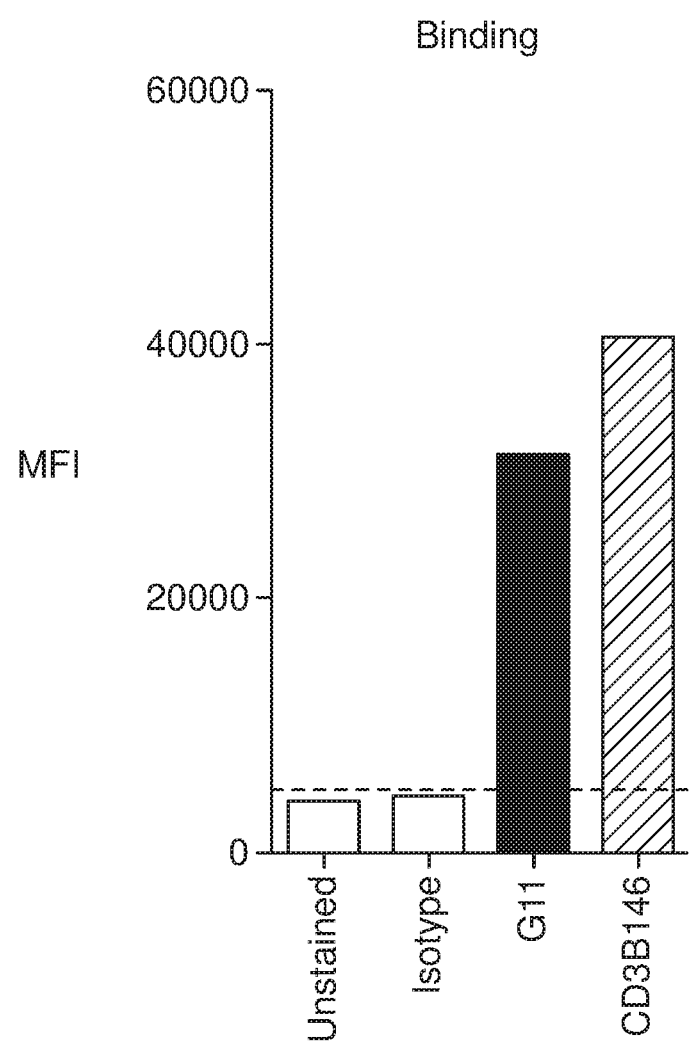
FIG. 1 shows binding of CD3B146 to primary Human T cells.

All publications, including patents and patent applications, cited in this specification are herein incorporated by reference as though fully set forth.

Definitions

It is to be understood that the terminology used herein is for the purpose of describing particular embodiments only and is not intended to be limiting. Unless defined otherwise, all technical and scientific terms used herein have the same meaning as commonly understood by one of ordinary skill in the art to which the invention pertains.

Although any methods and materials similar or equivalent to those described herein may be used in the practice for testing of the present invention, exemplary materials and methods are described herein. In describing and claiming the present invention, the following terminology will be used.

As used in this specification and the appended claims, the singular forms "a," "an," and "the" include plural referents unless the content clearly dictates otherwise. Thus, for example, reference to "a cell" includes a combination of two or more cells, and the like.

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

"Specific binding" or "specifically binds" or "specifically binding" or "binds" refer to an antibody binding to an antigen or an epitope within the antigen with greater affinity than for other antigens. Typically, the antibody binds to the antigen or the epitope within the antigen with an equilibrium dissociation constant ($K_D$) of about $5 \times 10^{-8}$ M or less, for example about $1 \times 10^{-9}$ M or less, about $1 \times 10^{-10}$ M or less, about $1 \times 10^{-11}$ M or less, or about $1 \times 10^{-12}$ M or less, typically with the K that is at least one hundred-fold less than its $K_D$ for binding to a non-specific antigen (e.g., BSA, casein). The dissociation constant may be measured using protocols described herein. Antibodies that bind to the antigen or the epitope within the antigen may, however, have cross-reactivity to other related antigens, for example to the same antigen from other species (homologs), such as human or monkey, for example *Macaca fascicularis* (*cynomolgus*, cyno) or *Pan troglodyles* (chimpanzee, chimp). While a monospecific antibody binds one antigen or one epitope, a bispecific antibody binds two distinct antigens or two distinct epitopes.

"Antibodies" is meant in a broad sense and includes immunoglobulin molecules including monoclonal antibodies including murine, human, humanized and chimeric monoclonal antibodies, antigen binding fragments, multispecific antibodies, such as bispecific, trispecific, tetraspecific etc., dimeric, tetrameric or multimeric antibodies, single chain antibodies, domain antibodies and any other modified configuration of the immunoglobulin molecule that comprises an antigen binding site of the required specificity. "Full length antibodies" are comprised of two heavy chains (HC) and two light chains (LC) inter-connected by disulfide bonds as well as multimers thereof (e.g. IgM). Each heavy chain is comprised of a heavy chain variable region (VH) and a heavy chain constant region (comprised of domains CH1, hinge, CH2 and CH3). Each light chain is comprised of a light chain variable region (VL) and a light chain constant region (CL). The VH and the VL regions may be further subdivided into regions of hypervariability, termed complementarity determining regions (CDR), interspersed with framework regions (FR). Each VH and VL is composed of three CDRs and four FR segments, arranged from amino-to-carboxy-terminus in the following order: FR1, CDR1, FR2, CDR2, FR3, CDR3 and FR4.

"Complementarity determining regions (CDR)" are antibody regions that bind an antigen. CDRs may be defined using various delineations such as Kabat (Wu et al. (1970) *J Exp Med* 132: 211-50)(Kabat et al., Sequences of Proteins of Immunological Interest, 5th Ed. Public Health Service, National Institutes of Health, Bethesda, Md., 1991), Chothia (Chothia et al. (1987) *J Mol Biol* 196: 901-17), IMGT (Lefranc et al. (2003) *Dev Comp Immunol* 27: 55-77) and AbM (Martin and Thornton (1996) *J Bmol Biol* 263: 800-

15). The correspondence between the various delineations and variable region numbering are described (see e.g. Lefranc et al. (2003) *Dev Comp Immunol* 27: 55-77; Honegger and Pluckthun, (2001) *J Mol Biol* 309:657-70; International ImMunoGeneTics (IMGT) database; Web resources, http://www_imgt_org). Available programs such as abYsis by UCL Business PLC may be used to delineate CDRs. The term "CDR", "HCDR1", "HCDR2", "HCDR3", "LCDR1", "LCDR2" and "LCDR3" as used herein includes CDRs defined by any of the methods described supra, Kabat, Chothia, IMGT or AbM, unless otherwise explicitly stated in the specification Immunoglobulins may be assigned to five major classes, IgA, IgD, IgE, IgG and IgM, depending on the heavy chain constant domain amino acid sequence. IgA and IgG are further sub-classified as the isotypes IgA1, IgA2, IgG1, IgG2, IgG3 and IgG4. Antibody light chains of any vertebrate species may be assigned to one of two clearly distinct types, namely kappa (κ) and lambda (λ), based on the amino acid sequences of their constant domains.

"Antigen binding fragment" refers to a portion of an immunoglobulin molecule that binds an antigen. Antigen binding fragments may be synthetic, enzymatically obtainable or genetically engineered polypeptides and include the VH, the VL, the VH and the VL, Fab, F(ab')2, Fd and Fv fragments, domain antibodies (dAb) consisting of one VH domain or one VL domain, shark variable IgNAR domains, camelized VH domains, minimal recognition units consisting of the amino acid residues that mimic the CDRs of an antibody, such as FR3-CDR3-FR4 portions, the HCDR1, the HCDR2 and/or the HCDR3 and the LCDR1, the LCDR2 and/or the LCDR3. VH and VL domains may be linked together via a synthetic linker to form various types of single chain antibody designs where the VH/VL domains may pair intramolecularly, or intermolecularly in those cases when the VH and VL domains are expressed by separate single chain antibody constructs, to form a monovalent antigen binding site, such as single chain Fv (scFv) or diabody; described for example in Int. Patent Publ. Nos. WO1998/44001, WO1988/01649, WO1994/13804 and WO1992/01047.

"Monoclonal antibody" refers to an antibody obtained from a substantially homogenous population of antibody molecules, i.e., the individual antibodies comprising the population are identical except for possible well-known alterations such as removal of C-terminal lysine from the antibody heavy chain or post-translational modifications such as amino acid isomerization or deamidation, methionine oxidation or asparagine or glutamine deamidation. Monoclonal antibodies typically bind one antigenic epitope. A bispecific monoclonal antibody binds two distinct antigenic epitopes. Monoclonal antibodies may have heterogeneous glycosylation within the antibody population. Monoclonal antibody may be monospecific or multispecific such as bispecific, monovalent, bivalent or multivalent.

"Isolated" refers to a homogenous population of molecules (such as synthetic polynucleotides or a protein such as an antibody) which have been substantially separated and/or purified away from other components of the system the molecules are produced in, such as a recombinant cell, as well as a protein that has been subjected to at least one purification or isolation step. "Isolated antibody" refers to an antibody that is substantially free of other cellular material and/or chemicals and encompasses antibodies that are isolated to a higher purity, such as to 80%, 81%, 82%, 83%, 84%, 85%, 86%, 87%, 88%, 89%, 90%, 91%, 92%, 93%, 94%, 95%, 96%, 97%, 98%, 99% or 100% purity.

"Humanized antibody" refers to an antibody in which at least one CDR is derived from non-human species and at least one framework is derived from human immunoglobulin sequences. Humanized antibody may include substitutions in the frameworks so that the frameworks may not be exact copies of expressed human immunoglobulin or human immunoglobulin germline gene sequences.

"Human antibody" refers to an antibody that is optimized to have minimal immune response when administered to a patient. Variable regions of human antibody are derived from human immunoglobulin sequences. If human antibody contains a constant region or a portion of the constant region, the constant region is also derived from human immunoglobulin sequences. Human antibody comprises heavy and light chain variable regions that are "derived from" sequences of human origin if the variable regions of the human antibody are obtained from a system that uses human germline immunoglobulin or rearranged immunoglobulin genes. Such exemplary systems are human immunoglobulin gene libraries displayed on phage, and transgenic non-human animals such as mice or rats carrying human immunoglobulin loci. "Human antibody" typically contains amino acid differences when compared to the immunoglobulins expressed in humans due to differences between the systems used to obtain the human antibody and human immunoglobulin loci, introduction of somatic mutations or intentional introduction of substitutions into the frameworks or CDRs, or both. Typically, "human antibody" is at least about 80%, 81%, 82%, 83%, 84%, 85%, 86%, 87%, 88%, 89%, 90%, 91%, 92%, 93%, 94%, 95%, 96%, 97%, 98% or 99% identical in amino acid sequence to an amino acid sequence encoded by human germline immunoglobulin or rearranged immunoglobulin genes. In some cases, "human antibody" may contain consensus framework sequences derived from human framework sequence analyses (Knappik et al., (2000) *J Mol Biol* 296:57-86), or synthetic HCDR3 incorporated into human immunoglobulin gene libraries displayed on phage (Shi et al., (2010) *J Mol Biol* 397:385-96); Int. Patent Publ. No. WO2009/085462).

Antibodies in which at least one CDR is derived from a non-human species are not included in the definition of "human antibody".

"Recombinant" refers to DNA, antibodies and other proteins that are prepared, expressed, created or isolated by recombinant means when segments from different sources are joined to produce recombinant DNA, antibodies or proteins.

"Epitope" refers to a portion of an antigen to which an antibody specifically binds. Epitopes typically consist of chemically active (such as polar, non-polar or hydrophobic) surface groupings of moieties such as amino acids or polysaccharide side chains and may have specific three-dimensional structural characteristics, as well as specific charge characteristics. An epitope may be composed of contiguous and/or discontiguous amino acids that form a conformational spatial unit. For a discontiguous epitope, amino acids from differing portions of the linear sequence of the antigen come in close proximity in 3-dimensional space through the folding of the protein molecule.

"Bispecific" refers to an antibody that specifically binds two distinct antigens or two distinct epitopes within the same antigen. The bispecific antibody may have cross-reactivity to other related antigens, for example to the same antigen from other species (homologs), such as human or monkey, for example *Macaca cynomolgus* (cynomolgus, cyno) or *Pan troglodytes*, or may bind an epitope that is shared between two or more distinct antigens.

"Multispecific" refers to an antibody that specifically binds two or more distinct antigens or two or more distinct epitopes within the same antigen. The multispecific antibody may have cross-reactivity to other related antigens, for example to the same antigen from other species (homologs), such as human or monkey, for example *Macaca cynomolgus* (*cynomolgus*, cyno) or *Pan troglodyles*, or may bind an epitope that is shared between two or more distinct antigens.

"Variant" refers to a polypeptide or a polynucleotide that differs from a reference polypeptide or a reference polynucleotide by one or more modifications, for example one or more substitutions, insertions or deletions.

"Vector" refers to a polynucleotide capable of being duplicated within a biological system or that can be moved between such systems. Vector polynucleotides typically contain elements, such as origins of replication, polyadenylation signal or selection markers, that function to facilitate the duplication or maintenance of these polynucleotides in a biological system, such as a cell, virus, animal, plant, and reconstituted biological systems utilizing biological components capable of duplicating a vector. The vector polynucleotide may be DNA or RNA molecules or a hybrid of these, single stranded or double stranded.

"Expression vector" refers to a vector that can be utilized in a biological system or in a reconstituted biological system to direct the translation of a polypeptide encoded by a polynucleotide sequence present in the expression vector.

"Polynucleotide" refers to a synthetic molecule comprising a chain of nucleotides covalently linked by a sugar-phosphate backbone or other equivalent covalent chemistry. cDNA is an exemplary synthetic polynucleotide.

"Polypeptide" or "protein" refers to a molecule that comprises at least two amino acid residues linked by a peptide bond to form a polypeptide. Small polypeptides of less than 50 amino acids may be referred to as "peptides".

"PSMA" refers to prostate specific membrane antigen. The amino acid sequence of the full length human PSMA is shown in SEQ ID NO: 1. The extracellular domain spans residues 44-750 of the full length PSMA. All references to proteins, polypeptides and protein fragments herein are intended to refer to the human version of the respective protein, polypeptide or protein fragment unless explicitly specified as being from a non-human species. Thus, "PSMA" means human PSMA unless specified as being from a non-human species, e.g., "mouse PSMA" or "monkey PSMA" etc.

(full length human PSMA)
SEQ ID NO: 1
MWNLLHETDSAVATARRPRWLCAGALVLAGGFFLLGFLFGWFIKSSNEAT

NITPKHNMKAFLDELKAENIKKFLYNFTQIPHLAGTEQNFQLAKQIQSQW

KEFGLDSVELAHYDVLLSYPNKTHPNYISIINEDGNEIFNTSLFEPPPPG

YENVSDIVPPFSAFSPQGMPEGDLVYVNYARTEDFFKLERDMKINCSGKI

VIARYGKVFRGNKVKNAQLAGAKGVILYSDPADYFAPGVKSYPDGWNLPG

GGVQRGNILNLNGAGDPLTPGYPANEYAYRRGIAEAVGLPSIPVIIPIGY

YDAQKLLEKMGGSAPPDSSWRGSLKWYNVGPGFTGNFSTQKVICMHIHST

NEVTRIYNVIGTLRGAVEPDRYVILGGHRDSWVFGGIDPQSGAAVVHEIV

RSFGTLKKEGWRPRRTILFASWDAEEFGLLGSTEWAEENSRLLQERGVAY

INADSSIEGNYTLRVDCTPLMYSLVHNLTKELKSPDEGFEGKSLYESWTK

KSPSPEFSGMPRISKLGSGNDFEVFFQRLGIASGRARYTKNWETNKFSGY

PLYHSVYETYELVEKFYDPMFKYHLTVAQVRGGMVFELANSIVLPFDCRD

YAVVLRKYADKIYSISMKHPQEMKTYSVSFDSLFSAVKNFTEIASKFSER

LQDFDKSNPIVLRMMNDQLMFLERAFIDPLGLPDRPFYRHVIYAPSSHNK

YAGESFPGIYDALFDIESKVDPSKAWGEVKRQIYVAAFTVQAAAETLSEV

A

"CD3" refers to an antigen which is expressed on T cells as part of the multimolecular T cell receptor (TCR) complex and which consists of a homodimer or heterodimer formed from the association of two or four receptor chains: CD3 epsilon, CD3 delta, CD3 zeta and CD3 gamma. Human CD3 epsilon comprises the amino acid sequence of SEQ ID NO: 4. The extracellular domain spans residues 23-126 of the full length CD3. All references to proteins, polypeptides and protein fragments herein are intended to refer to the human version of the respective protein, polypeptide or protein fragment unless explicitly specified as being from a non-human species. Thus, "CD3" means human CD3 unless specified as being from a non-human species, e.g., "mouse CD3" "monkey CD3," etc.

(Human CD3 epsilon)
SEQ ID NO: 4
MQSGTHWRVLGLCLLSVGVWGQDGNEEMGGITQTPYKVSISGTTVILTCP

QYPGSEILWQHNDKNIGGDEDDKNIGSDEDHLSLKEFSELEQSGYYVCYP

RGSKPEDANFYLYLRARVCENCMEMDVMSVATIVIVDICITGGLLLLVYY

WSKNRKAKAKPVTRGAGAGGRQRGQNKERPPPVPNPDYEPIRKGQRDLYS

GLNQRRI

"Bispecific anti-PSMA/anti-CD3 antibody", PSMA/CD3 antibody, PSMAxCD3 antibody and the like refer to an antibody that binds to PSMA and CD3.

"In combination with" means that two or more therapeutic agents are administered to a patient together in a mixture, concurrently as single agents or sequentially as single agents in any order.

"PSMA positive cancer" refers to a cancer tissue or a cancer cell that displays measurable level of PSMA protein. Level of PSMA protein may be measured using well known assays using, for example ELSA, immunofluorescence, flow cytometry or radioimmunoassay on live or lysed cells.

"Sample" refers to a collection of similar fluids, cells, or tissues isolated from a subject, as well as fluids, cells, or tissues present within a subject. Exemplary samples are of biological fluids such as blood, serum and serosal fluids, plasma, lymph, urine, saliva, cystic fluid, tear drops, feces, sputum, mucosal secretions of the secretory tissues and organs, vaginal secretions, ascites fluids such as those associated with non-solid tumors, fluids of the pleural, pericardial, peritoneal, abdominal and other body cavities, fluids collected by bronchial lavage, liquid solutions contacted with a subject or biological source, for example, cell and organ culture medium including cell or organ conditioned medium, lavage fluids and the like, tissue biopsies, fine needle aspirations or surgically resected tumor tissue.

A "cancer cell" or a "tumor cell" refers to a cancerous, or transformed cell, either in vivo, ex vivo, or in tissue culture, that has spontaneous or induced phenotypic changes. These changes do not necessarily involve the uptake of new genetic material. Although transformation may arise from infection with a transforming virus and incorporation of new genomic nucleic acid or uptake of exogenous nucleic acid, it can also arise spontaneously or following exposure to a carcinogen, thereby mutating an endogenous gene. Transformation/cancer is exemplified by morphological changes, immortalization of cells, aberrant growth control, foci formation, proliferation, malignancy, modulation of tumor specific marker levels, invasiveness, tumor growth in suitable animal hosts such as nude mice, and the like, in vitro, in vivo, and ex vivo (Freshney, Culture of Animal Cells: A Manual of Basic Technique (3rd ed. 1994)).

"About" means within an acceptable error range for the particular value as determined by one of ordinary skill in the art, which will depend in part on how the value is measured or determined, i.e., the limitations of the measurement system. Unless explicitly stated otherwise within the Examples or elsewhere in the Specification in the context of a particular assay, result or embodiment, "about" means within one standard deviation per the practice in the art, or a range of up to 5%, whichever is greater.

"Treat" or "treatment" refer to the treatment of a patient afflicted with a pathological condition and refers to an effect that alleviates the condition by killing the cancerous cells, but also to an effect that results in the inhibition of the progress of the condition, and includes a reduction in the rate of progress, a halt in the rate of progress, amelioration of the condition, and cure of the condition. Treatment as a prophylactic measure (i.e., prophylaxis) is also included.

"Therapeutically effective amount" refers to an amount effective, at doses and for periods of time necessary, to treat the cancer. A therapeutically effective amount may vary depending on factors such as the disease state, age, sex, and weight of the individual, and the ability of a therapeutic or a combination of therapeutics to elicit a desired response in the individual. Exemplary indicators of an effective therapeutic agent or combination of therapeutic agents that include, for example, improved well-being of the patient as a result of the treatment.

According to the invention as defined herein, the term "safe amount", as it relates to a dose or treatment with the anti-PSMAxCD3 antigen binding fragment having a first binding domain that specifically binds PSMA and a second binding domain that specifically binds CD3, wherein the first binding domain comprises a heavy chain (HC) of SEQ ID NO:7 and a light chain (LC) of SEQ ID NO:8 and the second binding domain comprises a heavy chain (HC) of SEQ ID NO:17 and a light chain (LC) of SEQ ID NO:18, refers to a favorable risk:benefit ratio with a relatively low or reduced frequency and/or low or reduced severity of adverse events, including adverse vital signs (heart rate, systolic and diastolic blood pressure, body temperature), adverse standard clinical laboratory tests (hematology, clinical chemistry, urinalysis, lipids, coagulation), allergic reactions/hypersensitivity, adverse local injection site reactions, or adverse EKG.

As used herein, unless otherwise noted, the term "clinically proven" (used independently or to modify the terms "safe" and/or "effective") mean that it has been proven by a clinical trial wherein the clinical trial has met the standards of U.S. Food and Drug Administration, EMEA or a corresponding national regulatory agency. For example, the clinical study may be an adequately sized, randomized, double blinded study used to clinically prove the effects of the drug. In some embodiments, "clinically proven" indicates that it has been proven by a clinical trial that has met the standards of the U.S. Food and Drug Administration, EMEA or a corresponding national regulatory agency for a Phase I clinical trial.

Anti-PSMAxCD3 Antibodies

The present invention provides for compositions include a PSMAxCD3 antigen binding fragment having a first binding domain that specifically binds PSMA and a second binding domain that specifically binds CD3, wherein the first binding domain includes a heavy chain (HC) of SEQ ID NO:7 and a light chain (LC) of SEQ ID NO:8 and the second binding domain includes a heavy chain (HC) of SEQ ID NO:17 and a light chain (LC) of SEQ ID NO:18. The invention is also directed to methods of treating metastatic castration-resistant prostate cancer comprising, consisting or consisting essentially of administer a safe amount of the anti-PSMAxCD3 antibody described above to a male human with a metastatic castration-resistant prostate cancer.

The numbering of amino acid residues in the antibody constant region throughout the specification is according to the EU index, unless otherwise explicitly stated.

Conventional one and three-letter amino acid codes are used herein as shown in Table 1.

TABLE 1

| Amino acid | Three-letter code | One-letter code |
|---|---|---|
| Alanine | Ala | A |
| Arginine | Arg | R |
| Asparagine | Asn | N |
| Aspartate | Asp | D |
| Cysteine | Cys | C |
| Glutamate | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Therapeutic Application

The present invention also provides a method for modulating or treating at least one PSMA related disease, in a cell, tissue, organ, animal, or patient, as known in the art or as described herein, using at least one dual integrin antibody of the present invention.

The present invention also provides a method for modulating or treating at least one prostate cancer related disease, in a cell, tissue, organ, animal, or patient including, but not limited to, at least one of advance solid tumors, metastatic castration-resistant prostate cancer (mCRPC), prostate cancer patient with relapsed disease following androgen receptor (AR)-targeted therapy.

The term "cancer" as used herein refers to an abnormal growth of cells which tend to proliferate in an uncontrolled way and, in some cases, to metastasize (spread).

The term "prostate cancer" as used herein refers to histologically or cytologically confirmed adenocarcinoma of the prostate.

The term "androgen-deprivation therapy (ADT)" refers to the reduction of androgen levels in a prostate cancer patient to castrated levels of testosterone (<50 ng/dL). Such treatments can include orchiectomy or the use of gonadotropin-releasing hormone agonists or antagonists. ADT includes surgical castration (orchiectomy) and/or the administration of luteinizing hormone-releasing hormone ("LHRH") agonists to a human. Examples of LHRH agonists include goserelin acetate, histrelin acetate, leuprolide acetate, and triptorelin palmoate. Physicians can prescribe LHRH agonists in accordance with instructions, recommendations and practices. This may include about 0.01 mg to about 20 mg of goserelin over a period of about 28 days to about 3 months, preferably about 3.6 mg to about 10.8 mg of goserelin over a period of about 28 days to about 3 months; about 0.01 mg to about 200 mg of leuprolide over a period of about 3 days to about 12 months, preferably about 3.6 mg of leuprolide over a period of about 3 days to about 12 months; or about 0.01 mg to about 20 mg of triptorelin over a period of about 1 month, preferably about 3.75 mg of triptorelin over a period of 1 month. About 50 mg of histrelin acetate over a period of 12 months of histrelin acetate or about 50 µg per day of histrelin acetate.

The term "locally advanced prostate cancer" refers to prostate cancer where all actively cancerous cells appear to be confined to the prostate and the associated organs or neighbor organs (e.g., seminal vesicle, bladder neck, and rectal wall).

The term "high-risk localized prostate cancer" refers to locally advanced prostate cancer that has a probability of developing metastases or recurrent disease after primary therapy with curative intent. In some embodiments, high risk for development of metastases is defined as prostate specific antigen doubling time (PSADT)<20 months, <19 months, <18 months, <17 months, <16 months, <15 months, <14 months, <13 months, <12 months, or <11 months, <10 months, <9 months, <8 months, <7 months, <6 months, <5 months, <4 months, <3 months, <2 months, or <1 month. In some embodiments, high risk for development of metastases is defined as prostate specific antigen doubling time (PSADT)<10 months. In some embodiments, high risk for development of metastases is defined as having a high Gleason score or bulky tumor.

The term "castration-sensitive prostate cancer" refers to cancer that is responsive to androgen-deprivationtherapy (ADT) either as localized disease, biochemical relapse or in the metastatic setting.

The term "metastatic castration-sensitive prostate cancer" refers to cancer that has spread (metastasized) to other areas of the body, e.g., the bone, lymph nodes or other parts of the body in a male, and that is responsive to androgen-deprivation therapy (ADT).

The term "non-metastatic castration-sensitive prostate cancer" refers to cancer that has not spread (metastasized) in a male, and that is responsive to androgen-deprivation therapy (ADT). In some embodiments, non-metastatic castration-sensitive prostate cancer is assessed with bone scan and computed tomography (CT) or magnetic resonance imaging (MRI) scans. [0089] The term "CRPC" as used herein refers to castration-resistant prostate cancer. CRPC is prostate cancer that continues to grow despite the suppression of male hormones that fuel the growth of prostate cancer cells.

The term "metastatic castration-resistant prostate cancer" refers to castration-resistant prostate cancer that has metastasized to other parts of the human body.

The term "NM-CRPC" as used herein refers to non-metastatic castration-resistant prostate cancer. In some embodiments, NM-CRPC is assessed with bone scan and computed tomography (CT) or magnetic resonance imaging (MRI) scans.

The term "chemotherapy naive metastatic castration-resistant prostate cancer" refers to metastatic castration-resistant prostate cancer that has not been previously treated with a chemotherapeutic agent.

In some embodiments, the non-metastatic castration-resistant prostate cancer is a high risk non-metastatic castration-resistant prostate cancer. The term "high risk NM-CRPC" refers to probability of a man with NM-CRPC developing metastases. In some embodiments, high risk for development of metastases is defined as prostate specific antigen doubling time (PSADT)<20 months, <19 months, <18 months, <17 months, <16 months, <15 months, <14 months, <13 months, <12 months, or <11 months, <10 months, <9 months, <8 months, <7 months, <6 months, <5 months, <4 months, <3 months, <2 months, or <1 month. In some embodiments, high risk for development of metastases is defined as prostate specific antigen doubling time (PSADT)<10 months. In some embodiments, high risk for development of metastases is defined as having local-regional recurrence (e.g. primary tumor bed, bladder neck, anastomotic area, pelvic lymph nodes).

The terms "co-administration" or the like, as used herein, encompass administration of the selected therapeutic agents to a patient, and are intended to include treatment regimens in which the agents are administered by the same or different route of administration or at the same or different time.

The term "metastasis-free survival" or "MFS" refers to the percentage of patients in a study who have survived without cancer spread for a defined period of time or death. MFS is usually reported as time from the beginning of enrollment, randomization or treatment in the study. MFS is reported for an individual or a study population. In the context of treatment of CRPC with an anti-androgen, an increase in the metastasis-free survival is the additional time that is observed without cancer having spread or death, whichever occurs first, as compared to treatment with placebo. In some embodiments, the increase in the metastasis-free survival is about 1 month, about 2 months, about 3 months, about 4 months, about 5 months, about 6 months, about 7 months, about 8 months, about 10 months, about 11 months, about 12 months, about 13 months, about 14 months, about 15 months, about 16 months, about 17 months, about 18 months, about 19 months, about 20 months, or greater than 20 months. In some embodiments, administration of a safe and effective amount of an anti-androgen provides an increase in the metastasis-free survival of a male human, optionally wherein the increase in the metastasis-free survival is relative to the mean survival rate of a population of male humans with the non-metastatic castration-resistant prostate cancer, said population having been treated with a placebo. In some embodiments, metastasis-free survival refers to the time from randomization to the time of first evidence of BICR-confirmed bone or soft tissue distant metastasis or death due to any cause, whichever occurs first.

The term "time to metastasis" is the time from randomization to the time of the scan that shows first evidence of BICR-confirmed radiographically detectable bone or soft tissue distant metastasis. In some embodiments, administration of an anti-androgen provides to a patient improved anti-tumor activity as measured by time to metastasis (TTM).

The term "time to symptomatic progression" is defined as the time from randomization to documentation in the CRF of any of the following (whichever occurs earlier): (1) development of a skeletal-related event (SRE): pathologic fracture, spinal cord compression, or need for surgical intervention or radiation therapy to the bone; (2) pain progression or worsening of disease-related symptoms requiring initiation of a new systemic anti-cancer therapy; or (3) development of clinically significant symptoms due to loco-regional tumor progression requiring surgical intervention or radiation therapy. In some embodiments, administration of an anti-androgen to a patient provides improved anti-tumor activity as measured by time to symptomatic progression.

The term "overall survival" is defined as the time from randomization to the date of death due to any cause. Survival data for patients who are alive at the time of the analysis was to be censored on the last known date that they were alive. In addition, for patients with no post-baseline information survival, data was to be censored on the date of randomization; for patients who are lost to follow-up or who withdraw consent, data is censored on the last known date that they were alive. In some embodiments, administration of an anti-androgen to a patient provides improved anti-tumor activity as measured by overall survival.

The term "delay in symptoms related to disease progression" as used herein means an increase in time in the development of symptoms such as pain, urinary obstruction and quality of life considerations from the time of randomization on the trial of administered drug.

The term 'randomization' as it refers to a clinical trial refers to the time when the patient is confirmed eligible for the clinical trial and gets assigned to a treatment arm.

The terms "kit" and "article of manufacture" are used as synonyms.

Examples

Example 1. Material

Generation of PSMA cell lines. Expression vectors presenting full-length chimpanzee PSMA (SEQ ID NO: 2) or full length Cynomolgous monkey PSMA (SEQ ID NO: 3) were generated for use as screening tools to assess the anti-PSMA leads. Vectors were transiently transfected into HEK293F cells. Transfected 293F suspension cells were plated in growth medium plus serum to become adherent and selected for stable plasmid integration. Single cell populations were selected by serial dilution and the PSMA surface receptor expression was quantified by FACS using the (PSMAL antibody (Center) affinity Purified Rabbit Polyclonal Antibody (Catalog #OAAB02483, Aviva Systems Biology) as the primary antibody with a R-PE anti-rabbit secondary antibody (Catalog #111-116-144, Jackson ImmunoResearch Laboratories, Inc.) and a rabbit polyclonal IgG (Catalog #SC-532, Santa Cruz Biotechnology) as the isotype control).

(full length chimpanzee PSMA)
SEQ ID NO: 2
MWNLLHETDSAVATARRPRWLCAGALVLAGGFFLLGFLFGWFIKSSNEAT

NITPKHNMKAFLDELKAENIKKFLYNFTQIPHLAGTEQNFQLAKQIQSQW

KEFGLDSVELAHYDVLLSYPNKTHPNYISIINEDGNEIFNTSLFEPPPPG

YENVSDIVPPFSAFSPQGMPEGDLNYVNYARTEDFFKLERDMKINCSGKI

VIARYGKVFRGNKVKNAQLAGAKGVILYSDPADYFAPGVKSYPDGWNLPG

GGVQRGNILNLNGAGDPLTPGYPANEYAYRRGIAEAVGLPSIPVHPIGYY

DAQKLLEKMGGSAPPDSSWRGSLKVPYNVGPGFTGNFSTQKVKMHIHSTN

EVTRIYNVIGTLRGAVEPDRYVILGGHRDSWVFGGIDPQSGAAVVHEIVR

SFGTLKKEGWRPRRTILFASWDAEEFGLLGSTEWAEENSRLLQERGVAYI

NADSSIEGNYTLRVDCTPLMYSLVHNLTKELKSPDEGFEGKSLYESWTKK

SPSPEFSGMPRISKLGSGNDFEVFFQRLGIASGRARYTKNWETNKFSGYP

LYHSVYETYELVEKFYDPMFKYHLTVAQVRGGMVFELANSIVLPFDCRDY

AVVLRKYADKIYSISMICHPQEMKTYSVSFDSLFSAVKNFTEIASKFSER

LQDFDICSNPIVLRMMNDQLMFLERAFIDPLGLPDRPFYRHVIYAPSSHN

KYAGESFPGIYDALFDIESKVDPSKAWGEVKRQIYVAAFTVQAAAETLSE

VA (full length Cynomolgous monkey PSMA)
SEQ ID NO: 3
MWNLLHETDSAVATARRPRWLCAGALVLAGGFFLLGFLFGWFIKSSNEAT

NITPKHNMKAFLDELKAENIKKFLYNFTQIPHLAGTEQNFQLAKQIQSQW

KEFGLDSVELAHYDVLLSYPNKTHPNYISIINEDGNEIFNTSLFEPPPPG

YENVLDIVPPFSAFSPQGMPEGDLVYVNYARTEDFFICLERDMKINCSGK

IVIARYGKVFRGNKVKNAQLAGAKGVILYSDPADYFAPGVKSYPDGWNLP

GGGVQRGNILNLNGAGDPLTPGYPANEYAYRHGIAEAVGLPSIPVHPIGY

YDAQKLLEKMGGSAPPDSSWRGSLKVPYNVGPGFTGNFSTQKVKMHIHST

NEVTRIYNVIGTLRGAVEPDRYVILGGHRDSWVFGGIDPQSGAAVVHEIV

RSFGTLKKEGWRPRRTILFASWDAEEFGLLGSTEWAEENSRLLQERGVAY

INADSSIEGNYTLRVDCTPLMYSLVYNLTKELKSPDEGFEGKSLYESWTK

KSPSPEFSGMPRISICLGSGNDFEVFFQRLGIASGRARYTICNWETNKFS

GYPLYHSVYETYELVEKFYDPMFKYHLTVAQVRGGMVFELANSIVLPFDC

RDYAVVLRKYADKIYNISMKHPQEMKTYSVSFDSLFSAVKNFTEIASKFT

ERLQDFDKSNPILLRMMNDQLMFLERAFIDPLGLPDRPFYRHVIYAPSSH

NKYAGESFPGIYDALFDIESKVDPSKAWGDVKRQISVAAFTVQAAAETLS

EVA

Human PSMA expressing cell lines were generated using lentivirus (Genecopoeia, cat #EX-G0050-Lv105-10) containing full length human PSMA (FOLH1_HUMAN, SEQ ID NO:1) and puromycin for selection of PSMA positive cells. HEK293F cells (ATCC), negative for PSMA, were transduced with Lentiviral particles to overexpress human PSMA. Following transduction, cells positively expressing PSMA and the resistance marker were selected by treating pooled cells, grown in DMEM+10% HI FBS (Life Technologies) and supplemented with varying concentrations of Puromycin (Life Technologies).

In addition to the HEK generated cell lines, several commercial cell lines were used for phage panning and binding and cellular toxicity assays. LNCaP clone FGC cells (ATCC cat #CRL-1740) are a commercially available human prostate cancer cell lines. C4-2B cells were originally developed at MD Anderson and are derived from LNCaP FGC grown in vivo and metastasize to bone marrow (Thalmann, et al 1994, Cancer Research 54, 2577-81).

Generation of Soluble PSMA ECD Proteins. Recombinant chimpanzee PSMA Extra Cellular Domain (ECD) protein (amino acid 44-750 of ECD, SEQ ID NO:2), recombinant cynomolgous monkey PSMA extracellular domain (ECD) protein (amino acid 44-750 of SEQ ID NO:3) and recombinant human PSMA extracellular domain (ECD) protein (amino acid 44-750 of SEQ ID NO:1), were generated for panning and to assess the anti-PSMA leads

Example 2. Generation of Anti-Chimp and Anti-Human PSMA Antibodies

Panning with recombinant protein. A first solution panning of the de novo Human Fab-pIX libraries (Shi, L., et al J Mol Biol, 2010. 397(2): p. 385-396. WO 2009/085462), consisting of VH 1-69, 3-23 and 5-51 heavy chain libraries paired with four human VL germline genes (A27, B3, L6, O12) libraries, was performed using an alternating panning approach with one round of phage capture on Strepavidin beads (Invitrogen Cat #112.05D, Lot #62992920) coated with biotinylated Chimp PSMA ECD according to the manufacturer's protocol, followed by phage capture on ProtG beads (Invitrogen, Cat #10003D) coated with Cyno-PSMA-Fc according to the manufacturer's protocol followed by phage capture on Sera-mag Double Speed magnetic Neutravidin beads (Thermo, Cat #7815-2104-011150) coated with biotinylated Chimp PSMA ECD according to the manufacturer's protocol.

Whole cell panning for anti-PSMA Fabs. Additional panning experiments were performed on whole cells using the Round #1 output from the chimpanzee ECD panning experiments described above or fresh de novo phage libraries, as input. Briefly, phage was produced by helper phage infection and concentrated by PEG/NaCl precipitation according to standard protocols known in the art. The phage libraries were pre-cleared on untransfected parental HEK293F cells overnight at 4° C. with gentle rocking. Following PEG/NaCl precipitation, the pre-cleared libraries were incubated with chimp PSMA expressing HEK293 cells or LNCAP cells with gentle rocking for 2 hr at 4° C. The removal of unbound phage and the recovery of phage-bound cells was performed by Ficoll gradient, and following several wash steps with, cells carrying bound phage were incubated with 1 mL of TG-1 *E. coli* culture at 37° C. for 30 minutes without agitation. The resulting mixture was plated on LB-Carbenicillin-1% Glucose plates and grown over night at 37° C. The process was then repeated for subsequent panning rounds.

Conversion of phage Fab-pIX to Fab-His for generating *E. coli* supernatants. The resulting phage Fab-pIX hits were converted to Fab-His using a standard procedure. Plasmid DNA was isolated from phage panned *E. coli* (Plasmid Plus Maxi Kit, Qiagen cat #12963) and subjected to NheI/SpeI restriction digest. The resulting 5400 and 100 bp fragments were separated on a 0.8% agarose gel and the 5400 bp fragment was gel purified (MinElute PCR purification kit, Qiagen cat #28006). The purified 5400 bp band was self-ligated using T4 ligase and the resulting product (encoding the Fab-his fusion) was transformed back into the TG-1 *E. coli* strain and clonally isolated. Fab-His supernatants were generated from clones by overnight induction of cultures with 1 mM IPTG. Following centrifugation of the overnight culture, clarified supernatants were ready for use in downstream assays. To determine the relative expression levels of different Fab-his supernatants, an anti-kappa (Southern Biotech cat #2061-05) ELISA on serially diluted supernatants was performed. All of the clones tested exhibited similar Fab-his expression (data not shown).

Cell binding of Fab-His fusions from *E. coli*. A cell-based binding assay was designed to assess the binding capabilities of individual Fab-his fusions from *E. coli* supernatants to PSMA-expressing cells. Individual Fab clones were isolated from the round 3 output of all panning experiments following pIX excision. Fab clones were tested for binding to chimp and cyno PSMA expressing HEK cells, as well as to human PSMA on LNCaP cells. Briefly, PSMA expressing cells were aliquoted into a V-bottom plate (CoStar 3357) at a density of 200,000 per well and incubated with (100 µl) supernatants expressing Fab fragments for 1 hour on ice. Cells were washed twice with PBS containing 2% FBS, and stained with a mouse anti-human kappa-RPE antibody (Life Technologies cat #MH10514) for 1 hour on ice. Cells were washed twice with PBS containing 2% FBS and resuspended in 100 µL of the same wash buffer. Plates were read on a BD FACS Array flow cytometer. FACS data was analyzed in FlowJo software by live gating the healthy population of cells using forward scatter and side scatter, and then analyzing the cells within this gate for PE staining. Mean fluorescence intensity (MFI) was calculated and exported into Microsoft Excel. Fab clones that exhibited binding ≥3 times background for all three species of PSMA (cyno, chimp and human), and exhibited no binding to the HEK293 cell line, were labeled as "preliminary positive". Fabs were sequenced and moved forward for cloning into mammalian expression vector for rescreening. True positives were selected from the binding of mammalian cell expressed Fab supernatants to PSMA-expressing cell lines.

Preparation of Mammalian Fabs. For conversion of *E. coli* Fab to mammalian-expressed Fab, In-Fusion HD cloning (ClonTech cat #638918) was utilized according to the manufacturer's protocol. Briefly, nucleotide sequences of clones that have passed the primary screen and are to be moved into mammalian Fab format, are loaded into the "InFu Primer Finder v.1.2.3" program (software developed in-house), which generates a list of isotype-specific PCR primers used to generate PCR fragments for In-Fusion cloning into the huKappa_muIgGSP and huGI Fab expression vectors. These vectors are in-house vectors with CMV promotors based off of pcDNA3.1. Following the In-fusion process, *E. coli* clones were isolated, sequence verified and transfected into HEK293 cells using standard protocols. Mammalian PSMA Fabs for confirming binding to PSMA expressing cell lines were prepared by harvesting 20 ml of supernatants from transfection after 5 days.

Rescreening hits from whole cell panning in mammalian sup format. Confirmation of mammalian expressed Fab supernatants was performed using a whole cell binding assay. Binding of Fabs to Chimpanzee, Cynomolgous monkey and human PSMA (LNCaP cells) was tested, as well as counter screening for no binding to the parental HEK cell line.

Dose response curves of mammalian expressed Fabs. Once mammalian expressed Fab clones were confirmed for positive binding as neat Fab supernatants to PSMA expressing cell lines, the supernatants were normalized for protein concentration by Octet or protein gel, and dose-response curves were completed to confirm PSMA binding using the protocol described previously.

Preparation of anti-PSMA mAbs. Clones that demonstrated binding to all three PSMA-expressing cells were ultimately converted to mAb IgG4 having Fc substitutions S228P, F234A, and L235A (PAA) isotype by restriction cloning. Briefly, constructs corresponding to Fab clones that have passed initial screens were digested with HindIII and ApaI. Gel purified fragments were ligated into an in-house expression vector with CMV promoter for generation of human IgG4-PAA expression. The in-house expression vector previously described was used to express the Heavy and Light Chains for each PSMA mab, where both vectors were co-transfected transiently into 293Expi or CHO cell lines for expression of the mAb.

A monospecific anti-PSMA antibody PSMB127 was generated comprising the VH and VL regions having the VH of SEQ ID NO: 5 and the VL of SEQ ID NO: 6 and an IgG4 constant region with S228P, F234A, and L235A substitutions as described below in Table 2 and 3.

TABLE 2

VH and VL of PSMB127

| FAB ID | VH Amino acid sequence | SEQ ID NO | VL Amino Acid Sequence | SEQ ID NO |
|---|---|---|---|---|
| PSMB127 | EVQLLESGGGLVQPGGSLRLSCAASGF TFKSDAMHWVRQAPGKGLEWVSEISG SGGYTNYADSVKGRFTISRDNSKNTLY LQMNSLRAEDTAVYYCARDSYDSSLY VGDYFDYWGQGTLVTVSS | 5 | EIVLTQSPATLSLSPGER ATLSCRASQSVSSYLAW YQQKPGQAPRLLIYDAS NRATGIPARFSGSGSGTD FTLTISSLEPEDFAVYYC QQRSNWPLTFGQGTKVE IK | 6 |

TABLE 3

HC and LC of PSMB127

| mAb ID | Heavy Chain Amino acid sequence | SEQ ID NO | Light Chain Amino Acid Sequence | SEQ ID NO |
|---|---|---|---|---|
| PSMB127 Protein | EVQLLESGGGLVQPGGSLRLSC AASGFTFKSDAMHWVRQAPGK GLEWVSEISGSGGYTNYADSVK GRFTISRDNSKNTLYLQMNSLR AEDTAVYYCARDSYDSSLYVG DYFDYWGQGTLVTVSSASTKG PSVFPLAPCSRSTSESTAALGCL VKDYFPEPVTVSWNSGALTSGV HTFPAVLQSSGLYSLSSVVTVPS SSLGTKTYTCNVDHKPSNTKVD KRVESKYGPPCPPCPAPEAAGG PSVFLFPPKPKDTLMISRTPEVT CVVVDVSQEDPEVQFNWYVDG VEVHNAKTKPREEQFNSTYRVV SVLTVLHQDWLNGKEYKCKVS NKGLPSSIEKTISKAKGQPREPQ VYTLPPSQEEMTKNQVSLTCLV KGFYPSDIAVEWESNGQPENNY KTTPPVLDSDGSFFLYSRLTVDK SRWQEGNVFSCSVMHEALHNH YTQKSLSLSLGK | 7 | EIVLTQSPATLSLSPGERATL SCRASQSVSSYLAWYQQKP GQAPRLLIYDASNRATGIPA RFSGSGSGTDFTLTISSLEPE DFAVYYCQQRSNWPLTFGQ GTKVEIKRTVAAPSVFIFPPS DEQLKSGTASVVCLLNNFYP REAKVQWKVDNALQSGNS QESVTEQDSKDSTYSLSSTLT LSKADYEKHKVYACEVTHQ GLSSPVTKSFNRGEC | 8 |
| | Heavy Chain DNA sequence | SEQ ID NO | Light Chain DNA Sequence | SEQ ID NO |
| PSMB127 DNA | ATGGCTTGGGTGTGGACCT TGCTATTCCTGATGGCAGCT GCCCAAAGTATACAGGCCG AGGTTCAGCTGCTGGAATC TGGCGGAGGATTGGTTCAG CCTGGCGGCTCTCTGAGAC TGTCTTGTGCCGCTTCTGGC TTCACCTTCAAGTCCGACG CTATGCACTGGGTCCGACA GGCCCCTGGAAAAGGACTG GAATGGGTGTCCGAGATCT CTGGCTCTGGCGGCTACAC CAACTACGCCGACTCCATG AAGTCCCGGTTCACCATCT CTCGGGACAACTCCAAGAA CACCCTGTACCTGCAGATG AACTCCCTGAGAGCCGAGG ACACCGCCGTGTACTACTG CGCCAGAGACTCCTACGAC TCCAGCCTGTACGTGGGCG ACTACTTCGATTATTGGGG CCAGGGCACCCTGGTCACC GTTTCTTCTGCTTCCACCAA GGGCCCATCCGTCTTCCCCC TGGCGCCCTGCTCCAGGAG CACCTCCGAGAGCACAGCC GCCCTGGGCTGCCTGGTCA AGGACTACTTCCCCGAACC GGTGACGGTGTCGTGGAAC TCAGGCGCCCTGACCAGCG GCGTGCACACCTTCCCGGC TGTCCTACAGTCCTCAGGA | 25 | ATGGCCTGGGTGTGGAC CCTGCTGTTCCTGATGGC CGCCGCCCAGAGCATCC AGGCCGAGATCGTGCTG ACCCAGAGCCCCGCCAC CCTGAGCCTGAGCCCCG GCGAGCGGGCCACCCTG AGCTGCCGGGCCAGCCA GAGCGTGAGCAGCTACC TGGCCTGGTACCAGCAG AAGCCCGGCCAGGCCCC CCGGCTGCTGATCTACG ACGCCAGCAACCGGGCC ACCGGCATCCCCGCCCG GTTCAGCGGCAGCGGCA GCGGCACCGACTTCACC CTGACCATCAGCAGCCT GGAGCCCGAGGACTTCG CCGTGTACTACTGCCAG CAGCGGAGCAACTGGCC CCTGACCTTCGGCCAGG GCACCAAGGTGGAGATC AAGCGTACGGTGGCTGC ACCATCTGTCTTCATCTT CCCGCCATCTGATGAGC AGTTGAAATCTGGAACT GCCTCTGTTGTGCCTG CTGAATAACTTCTATCCC AGAGAGGCCAAAGTACA GTGGAAGGTGGATAACG CCCTCCAATCGGGTAAC TCCCAGGAGAGTGTCAC | 26 |

TABLE 3-continued

HC and LC of PSMB127

| | |
|---|---|
| CTCTACTCCCTCAGCAGCGT | AGAGCAGGACAGCAAG |
| GGTGACCGTGCCCTCCAGC | GACAGCACCTACAGCCT |
| AGCTTGGGCACGAAAACCT | CAGCAGCACCCTGACGC |
| ACACCTGCAACGTAGATCA | TGAGCAAAGCAGACTAC |
| CAAGCCCAGCAACACCAAG | GAGAAACACAAAGTCTA |
| GTGGACAAGAGAGTTGAGT | CGCCTGCGAAGTCACCC |
| CCAAATATGGTCCCCCATG | ATCAGGGCCTGAGCTCG |
| CCCACCATGCCCAGCACCT | CCCGTCACAAAGAGCTT |
| GAGGCCGCCGGGGACCAT | CAACAGGGGAGAGTGT |
| CAGTCTTCCTGTTCCCCCCA | |
| AAACCCAAGGACACTCTCA | |
| TGATCTCCCGGACCCCTGA | |
| GGTCACGTGCGTGGTGGTG | |
| GACGTGAGCCAGGAAGACC | |
| CCGAGGTCCAGTTCAACTG | |
| GTACGTGGATGGCGTGGAG | |
| GTGCATAATGCCAAGACAA | |
| AGCCGCGGGAGGAGCAGTT | |
| CAACAGCACGTACCGTGTG | |
| GTCAGCGTCCTCACCGTCCT | |
| GCACCAGGACTGGCTGAAC | |
| GGCAAGGAGTACAAGTGCA | |
| AGGTCTCCAACAAAGGCCT | |
| CCCGTCCTCCATCGAGAAA | |
| ACCATCTCCAAAGCCAAAG | |
| GGCAGCCCCGAGAGCCACA | |
| GGTGTACACCCTGCCCCCA | |
| TCCCAGGAGGAGATGACCA | |
| AGAACCAGGTCAGCCTGAC | |
| CTGCCTGGTCAAAGGCTTC | |
| TACCCCAGCGACATCGCCG | |
| TGGAGTGGGAGAGCAATGG | |
| GCAGCCGGAGAACAACTAC | |
| AAGACCACGCCTCCCGTGC | |
| TGGACTCCGACGGCTCCTT | |
| CTTCCTCTACAGCAGGCTA | |
| ACCGTGGACAAGAGCAGGT | |
| GGCAGGAGGGGAATGTCTT | |
| CTCATGCTCCGTGATGCAT | |
| GAGGCTCTGCACAACCACT | |
| ACACACAGAAGAGCCTCTC | |
| CCTGTCTCTGGGTAAA | |

The interactions of parent PSMA mAbs PSMB127 with human, chimp, and cyno PSMA ECDs was measured by Surface Plasmon Resonance (SPR) using a ProteOn XPR36 system (BioRad). The summary of binding affinities to human, chimp, and cyno PSMA ECD are shown below.

TABLE 4

Kd data for PSMB127 against human, Chimp and Cyno PSMA

| | Human KD (nM) | Chimp KD (nM) | Cyno KD (nM) |
|---|---|---|---|
| PSMB127 | 12.0 ± 2.05 | 12.8 ± 1.83 | 6.68 ± 0.45 |

Example 3. Generation and Characterization of Anti-CD3 Antibody

Generation of anti-CD3 antibody. The commercial anti-CD3 antibody SP34, a mouse IgG1 isotype anti-human CD3 IgG1 antibody was humanized by the Human Framework Adaptation method (Fransson, et al, JMB, 2010 398(2):214-31). To preserve the conformation of CDR-H3, mouse residues at positions Val38, Gly48, Gly51 and V59 of VL and Ala at position 48 in VH were retained. These 'back mutations' were added into the humanization plan. The resulting anti-CD3 variant was called CD3B146.

Endogeneous cell binding of humanized anti-CD3 antibody to primary T cells. CD3B146 was tested for binding to cell-surface CD3ε on primary human T cells and primary cynomolgus CD4+ T cells to assess the retention of cross-reactivity. Purified CD4+ T cells from the peripheral blood of cynomolgus monkeys were used (Zen Bio, Triangle Research Park, USA). Briefly, binding of anti-CD3 antibodies to cell-surface CD3ε was assessed by flow cytometry using primary Human T lymphocytes purified by negative selection (Biological Specialty, Colmar, USA). Expression supernatants or purified antibodies were normalized to 10 μg/ml in media or FACS buffer (BD BioSciences), respectively. 2×105 cells were aliquoted into wells of a 96 well round-bottomed plate (CoStar) for labeling. Antibodies in expression supernatant were added to cells and incubated for 45 min at 4° C. Following centrifigation at 1300 rpm for 3 min and removal of supernatant, 50 μL of anti-human IgG (H+L) Alexa Fluor 647 secondary antibody (Life technologies Inc.) was incubated with the cells at a final concentration of 10 μg/mL for 30 min at 4° C. away from direct light, followed by washing and resuspension in 30 μL FACs buffer (BD BioSciences). Sample collection was performed on an Intellicyt HTFC system using ForeCyt software.

Figure 2:
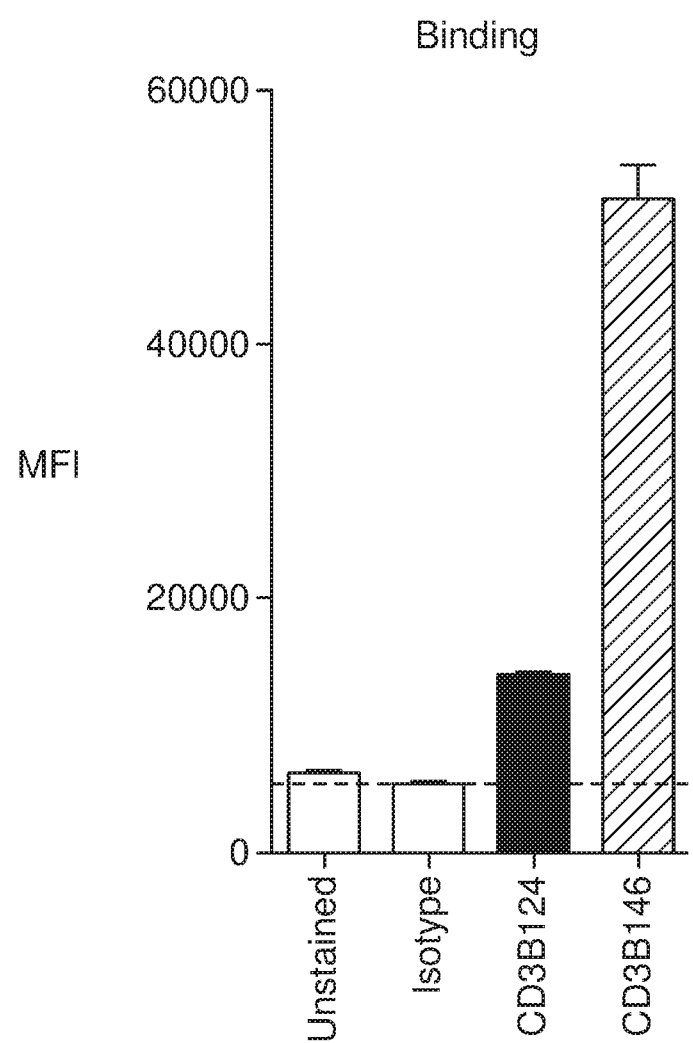
FIG. 2 shows binding of CD3B146 to *Cynomolgus* primary T cells.

Two in-house phage-derived antibodies with the same Fc region as the therapeutic antibodies were used as controls: G11, a non-cyno cross-reactive, agonistic antibody was used as a positive control and CD3B124 a non-binder/non-agonistic antibody was used to assess non-specific binding. The commercial SP34 antibody was not used as a comparator in this assay since it is a mouse antibody and the use of a different secondary detection reagent would have prohibited direct comparison with the variants tested. Although a titration series was run, an intermediate concentration is presented in FIG. 1 for clarity purpose, using mean fluorescence intensity values (FIM). CD3B146 shows strong binding to both human and cyno T cells indicating that CD3B146 retained species cross-reactivity between human and *cynomolgus* CD3ε (FIG. 1 and FIG. 2).

Figure 3:
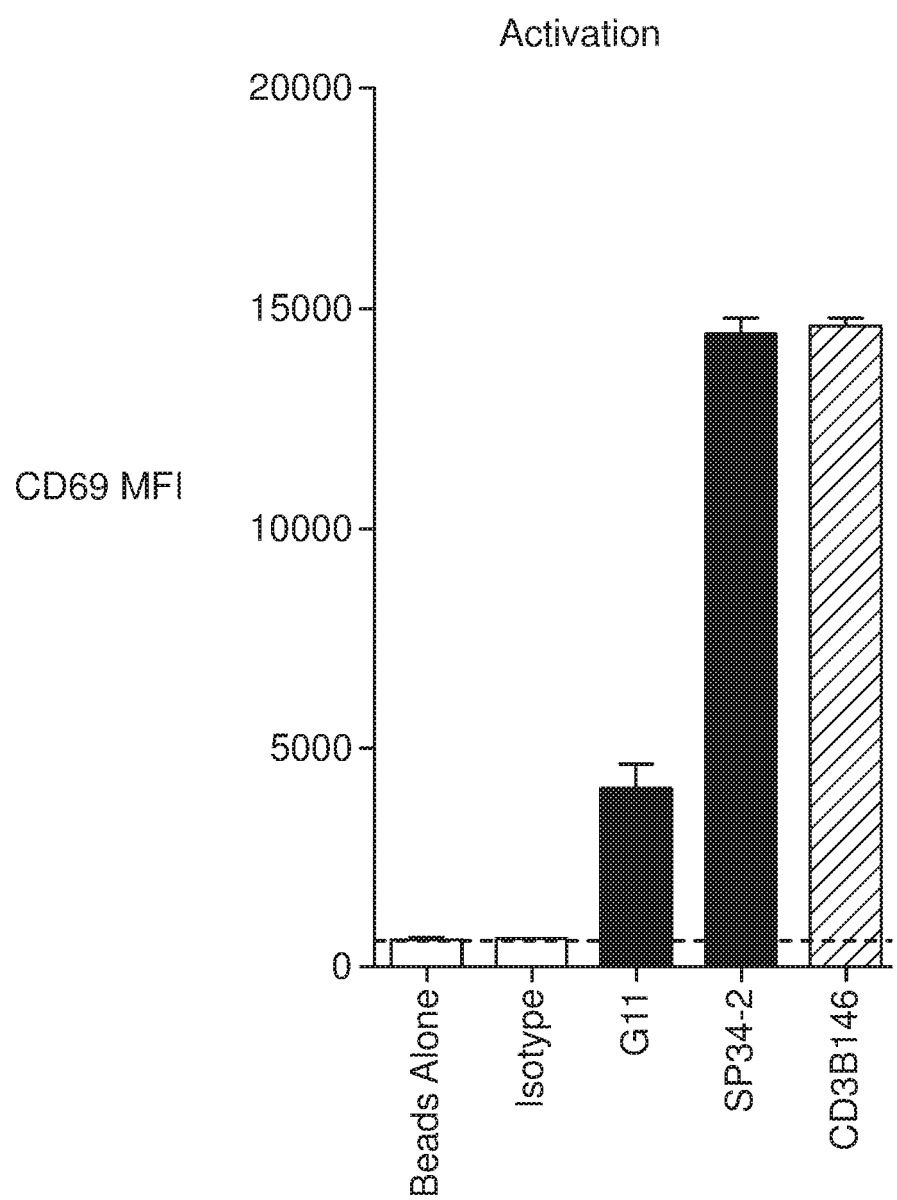
FIG. 3 shows that CD3B146 activates primary human T cells in vitro. Negative controls are shown in white and positive controls are shown in black.

Functional analysis of humanized anti-CD3 hits in primary T cells. To investigate the capacity of CD3B146 variant to induce activation of human T cells via CD3ε crosslinking, primary human T-cells were cultured overnight in the presence of bead-conjugated antibody. The following day, cells were harvested and labeled with an anti-CD69 antibody to measure activation. Humanized anti-CD3 antibodies were bound to protein A coated magnetic beads (SpheroTech, Lake forest, USA) The following day, 2×10$^5$ primary human T cells were plated in round-bottomed cell culture plates in triplicate and 2×10$^5$ coated beads were added. Following overnight culture at 37° C., cells were harvested and labeled with anti-CD69 Alexa Fluor® 488 antibody (clone FN50; Biolegend) to assess the up-regulation of this activation marker. Sample collection and analysis were performed as described above for binding. Several negative controls were run, including T-cells alone, T-cells with non-coated beads, and T-cells with isotype control (CD3B94)-coated beads. Positive controls were run for comparison, including commercially available SP34-2 antibody (FIG. 3).

Figure 4:
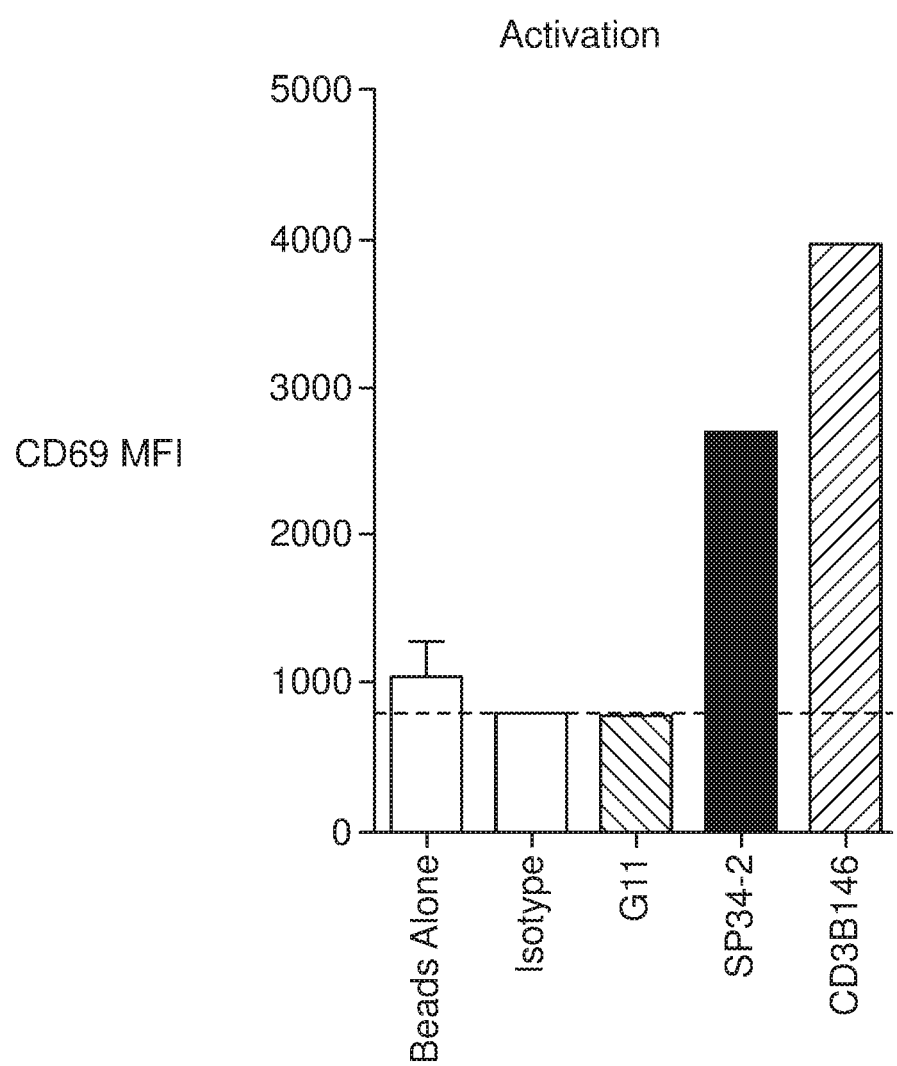
FIG. 4 shows that CD3B146 activates primary *cynomolgus* T cells in vitro. Negative controls are shown in white and positive controls are shown in black. Non-CD3ε-cross-reactive antibody G11 served as an additional negative control.

The humanized anti-CD3 antibody was then tested for their capacity to activate primary *cynomolgus* CD4+ T cells (Zen Bio, Triangle Research Park, USA) in the same assay (FIG. 4). The FN50 anti-CD69 antibody has been described as being cross-reactive with non-human protein and was therefore used to test activation of *cynomolgus* CD4+ T cells. CD3B146 showed the capacity to activate both human and *cynomolgus* (FIGS. 3 and 4).

Preparation of anti-CD3 mAbs. CD3B146 IgG1 was converted to the mAb IgG4 PAA GenMab Format (Labrijn et, 2013) having Fc substitutions S228P, F234A, and L235A (PAA), and F405L and R409K substitutions (numbering according to EU index). S233P, F234A and L235A are Fc silencing mutations, while F405L and R409K mutations will allow for heterodimerization with the PSMA antibody, which contains the native IgG4 F405 and R409 residues. In brief, heavy chain (HC) variable regions were subcloned onto human IgG4-PAA Fc containing S228P, F234A, L235A, F405L, and R409K mutations using an in-house expression vector with the CMV promoter using standard molecular biology techniques. Light chain (LC) variable regions were subcloned onto a human Lambda (λ) constant regions using an in-house expression vector with the CMV promoter using standard molecular biology techniques. Resulting plasmids were transfected into Expi293F cells (Invitrogen) and mAbs were expressed. The anti-CD3 antibodies were purified using standard purification methods: a protein A column with an elution buffer of 100 mM NaAc pH3.5 and a neutralization puffer of 2M Tris pH 7.5 and 150 mM NaCl. The mabs were desalted using PD10 (Sephadex G25M) column and the pools The monospecific anti-CD3 antibody generated was renamed CD3B219 and comprises the VH and VL regions having the VH of SEQ ID NO:15 and the VL of SEQ ID NO:16 and an IgG4 constant region with S228P, F234A, L235A, F405L, and R409K substitutions. CD3B219 comprises a heavy chain of SEQ ID NO: 17 and a light chain of SEQ ID NO:18. As a control, a monospecific anti-RSV antibody, derived from B21M, to partner as the null arm with either the CD3 or PSMA arm of a bispecific antibody. The VH and VL sequence of CD3B219 is shown in Table 5.

TABLE 5

VH, VL, HC and LC of CD3B219

| mAb | VH Amino Acid sequence | SEQ ID NO: | VL Amino Acid sequence | SEQ ID NO: |
|---|---|---|---|---|
| CD3B219 | EVQLVESGGGLVQPGGSLRL SCAASGFTFNTYAMNWVRQ APGKGLEWVARIRSKYNNY ATYYAASVKGRFTISRDDSK NSLYLQMNSLKTEDTAVYY CARHGNFGNSYVSWFAYW GQGTLVTVSS | 15 | QTVVTQEPSLTVSPGGTVTLT CRSSTGAVTTSNYANWVQQK PGQAPRGLIGGINKRAPGTPA RFSGSLLGGKAALTLSGVQPE DEAEYYCALWYSNLWVFGG GTKLTVL | 16 |
| | HC Amino Acid Sequence | SEQ ID NO: | LC Amino Acid sequence | SEQ ID NO: |
| CD3B219 | EVQLVESGGGLVQPGGSLRL SCAASGFTFNTYAMNWVRQ APGKGLEWVARIRSKYNNY ATYYAASVKGRFTISRDDSK NSLYLQIVINSLKTEDTAVYY CARHGNFGNSYVSWFAYW GQGTLVTVSSASTKGPSVFP LAPCSRSTSESTAALGCLVK DYFPEPVTVSWNSGALTSGV HTFPAVLQSSGLYSLSSVVT VPSSSLGTKTYTCNVDHKPS NTKVDKRVESKYGPPCPPCP APEAAGGPSVFLFPPKPKDT LMISRTPEVTCVVVDVSQED PEVQFNWYVDGVEVHNAKT KPREEQFNSTYRVVSVLTVL HQDWLNGKEYKCKVSNKG | 17 | QTVVTQEPSLTVSPGGTVTLT CRSSTGAVTTSNYANWVQQK PGQAPRGLIGGTNKRAPGTPA RFSGSLLGGKAALTLSGVQPE DEAEYYCALWYSNLWVFGG GTKLTVLGQPKAAPSVTLFPP SSEELQANKATLVCLISDFYP GAVTVAWKADSSPVKAGVE TTTPSKQSNNKYAASSYLSLT PEQWKSHRSYSCQVTHEGST VEKTVAPTECS | 18 |

TABLE 5 -continued

VH, VL, HC and LC of CD3B219

LPSSIEKTISKAKGQPREPQV
YTLPPSQEEMTKNQVSLICL
VKGFYPSDIAVEWESNGQPE
NNYKTTPPVLDSDGSFLLYS
KLTVDKSRWQEGNVFSCSV
MHEALHNHYTQKSLSLSLG
K

| Heavy Chain DNA sequence | SEQ ID NO | Light Chain DNA Sequence | SEQ ID NO |
|---|---|---|---|
| GAAGTGCAGCTGGTGGA ATCTGGCGGCGGACTGG TGCAGCCTGGCGGATCT CTGAGACTGAGCTGTGC CGCCAGCGGCTTCACCT TCAACACCTACGCCATG AACTGGGTGCGCCAGGC CCCTGGCAAAGGCCTGG AATGGGTGGCCCGGATC AGAAGCAAGTACAACAA TTACGCCACCTACTACG CCGCCTCCGTGAAGGGC AGATTCACCATCAGCCG GGACGACAGCAAGAACA GCCTGTACCTGCAGATG AACTCCCTGAAAACCGA GGACACCGCCGTGTACT ACTGCGCCAGACACGGC AACTTCGGCAACAGCTA TGTGTCTTGGTTTGCCTA CTGGGGCCAGGGCACCC TCGTGACCGTGTCATCTG CTTCCACCAAGGGCCCA TCCGTCTTCCCCCTGGCG CCCTGCTCCAGGAGCAC CTCCGAGAGCACAGCCG CCCTGGGCTGCCTGGTC AAGGACTACTTCCCCGA ACCGGTGACGGTGTCGT GGAACTCAGGCGCCCTG ACCAGCGGCGTGCACAC CTTCCCGGCTGTCCTACA GTCCTCAGGACTCTACTC CCTCAGCAGCGTGGTGA CCGTGCCCTCCAGCAGC TTGGGCACGAAAACCTA CACCTGCAACGTAGATC ACAAGCCCAGCAACACC AAGGTGGACAAGAGAGT TGAGTCCAAATATGGTC CCCCATGCCCACCATGC CCAGCACCTGAGGCCGC CGGGGGACCATCAGTCT TCCTGTTCCCCCCAAAAC CCAAGGACACTCTCATG ATCTCCCGGACCCCTGA GGTCACGTGCGTGGTGG TGGACGTGAGCCAGGAA GACCCCGAGGTCCAGTT CAACTGGTACGTGGATG GCGTGGAGGTGCATAAT GCCAAGACAAAGCCGCG GGAGGAGCAGTTCAACA GCACGTACCGTGTGGTC AGCGTCCTCACCGTCCT GCACCAGGACTGGCTGA ACGGCAAGGAGTACAAG TGCAAGGTCTCCAACAA AGGCCTCCCGTCCTCCAT CGAGAAAACCATCTCCA AAGCCAAAGGGCAGCCC CGAGAGCCACAGGTGTA CACCCTGCCCCCATCCC AGGAGGAGATGACCAAG AACCAGGTCAGCCTGAC CTGCCTGGTCAAAGGCT TCTACCCCAGCGACATC | 27 | CAGACCGTCGTGACCCAG GAACCTAGCCTGACCGTG TCTCCTGGCGGCACCGTG ACCCTGACCTGCAGATCT TCTACAGGCGCCGTGACC ACCAGCAACTACGCCAAC TGGGTGCAGCAGAAGCC AGGCCAGGCTCCCAGAG GACTGATCGGCGGCACCA ACAAGAGAGCCCCTGGC ACCCCTGCCAGATTCAGC GGATCTCTGCTGGGAGGA AAGGCCGCCCTGACACTG TCTGGCGTGCAGCCTGAA GATGAGGCCGAGTACTAC TGCGCCCTGTGGTACAGC AACCTGTGGGTGTTCGGC GGAGGCACCAAGCTGAC AGTGCTGGGTCAGCCCAA GGCTGCACCCAGTGTCAC TCTGTTCCCGCCCTCCTCT GAGGAGCTTCAAGCCAAC AAGGCCACACTGGTGTGT CTCATAAGTGACTTCTAC CCGGGAGCCGTGACAGTG GCCTGGAAGGCCGATAGC AGCCCCGTCAAGGCGGG AGTGGAGACCACCACACC CTCCAAACAAAGCAACA ACAAGTACGCGGCCAGC AGCTATCTGAGCCTGACG CCTGAGCAGTGGAAGTCC CACAGAAGCTACAGCTGC CAGGTCACGCATGAAGG GAGCACCGTGGAGAAGA CAGTGGCCCCTACAGAAT GTTCA | 28 |

TABLE 5 -continued

VH, VL, HC and LC of CD3B219

```
GCCGTGGAGTGGGAGAG
CAATGGGCAGCCGGAGA
ACAACTACAAGACCACG
CCTCCCGTGCTGGACTCC
GACGGCTCCTTCCTCCTC
TACAGCAAGCTAACCGT
GGACAAGAGCAGGTGGC
AGGAGGGGAATGTCTTC
TCATGCTCCGTGATGCAT
GAGGCTCTGCACAACCA
CTACACACAGAAGAGCC
TCTCCCTGTCTCTGGGTA
AA
```

Example 4. Preparation of PSMAxCD3 Bispecific Antibody

The formation of the PSMAxCD3 bispecific antibody was performed by combining PSMA mAb PSMB127 (VH SEQ ID NO: 5, VL SEQ ID NO: 6) with the high affinity CD3B219 (VH SEQ ID NO: 15, VL SEQ ID NO: 16) CD3 arms. The targeting parent (PSMA) contains the native IgG4 amino acid F405 and R409, while the killing parent (CD3) contains the F405L GenMab mutation and R409K mutation.

The parental PSMA and CD3 antibodies were purified using a protein A column with an elution buffer of 100 mM NaAc pH3.5 and a neutralization puffer of 2M Tris pH 7.5 and 150 mM NaCl. The mAbs were desalted using PD10 (Sephadex G25M) column and dialyzed into D-PBS, pH 7.2 buffer.

Post purification the parental PSMA antibody was mixed with the desired parental CD3 antibody under reducing conditions in 75 mM cysteamine-HCl and incubated at 31° C. for 4 h. The recombination reaction was based on molar ratios, where a set amount of PSMA (e.g., 10 mg, or ~67.8 nanomoles) was combined with CD3 antibody (e.g., ~71.8 nanomoles), where the CD3 antibody was added in a 6% excess of the PSMA antibody. The concentrations of the PSMA antibody stocks varied from 0.8 to 6 mg/mL, and the volumes the recombination reactions varied for each pairing. The recombination was subsequently dialyzed against PBS to remove the reductant. The bispecific antibody reaction was performed with an excess of the CD3 antibody (ratio) to minimize the amount of unreacted PSMA parental antibody remaining after recombination. Following the partial reduction of the parental mAbs, the reductant was removed via overnight dialysis into PBS. The final PSMAxCD3 antibody was named PS3B27.

Selected PSMA hits were also paired with a non-killing arm (Null) to create negative controls for testing purposes. For control bispecific antibodies, B2M1, an RSV antibody in the IgG4 PAA format was generated, purified and, combined with either the CD3 arm CD3B219-F405L, R409K to generate CD3B288 (CD3xnull) or PSMA arms, PSMB162, PSMB126, PSMB130 to generate PS3B37, PS3B39 and PS3B40 respectively (PSMAxnull).

TABLE 6

HC and LC cDNA SEQ ID NOs.

| Antibody | HC cDNA SEQ ID NO: | LC cDNA SEQ ID NO: |
|---|---|---|
| PSMB127 | 25 | 26 |
| CD3B219 | 27 | 28 |

TABLE 7

VH, VL, HC and LC protein SEQ ID NOs.

| Antibody | VH SEQ ID NO: | VL SEQ ID NO: | HC SEQ ID NO: | LC SEQ ID NO: |
|---|---|---|---|---|
| PSMB127 | 5 | 6 | 7 | 8 |
| CD3B219 | 15 | 16 | 17 | 18 |

TABLE 8

HC/LC Sequences of PSMA X CD3 bispecific antibody (PS3B27) with corresponding SEQ ID NOs

| PS3B27 | Heavy Chain | SEQ ID NO | Light Chain | SEQ ID NO |
|---|---|---|---|---|
| PSMA Arm (PSMB127) | EVQLLESGGGLVQPGGSLRLSCA ASGFTFKSDAMHWVRQAPGKGL EWVSEISGSGGYTNYADSVKGRF TISRDNSKNTLYLQMNSLRAEDT AVYYCARDSYDSSLYVGDYFDY WGQGTLVTVSSASTKGPSVFPLA PCSRSTSESTAALGCLVKDYFPEP VTVSWNSGALTSGVHTFPAVLQS SGLYSLSSVVTVPSSSLGTKTYTC NVDHKPSNTKVDKRVESKYGPPC | 7 | EIVLTQSPATLSLSPGERATL SCRASQSVSSYLAWYQQKP GQAPRLLIYDASNRATGIPA RFSGSGSGTDFTLTISSLEPE DFAVYYCQQRSNWPLTFGQ GTKVEIKRTVAAPSVFIFPPS DEQLKSGTASVVCLLNNFYP REAKVQWKVDNALQSGNS QESVTEQDSKDSTYSLSSTLT LSKADYEKHKVYACEVTHQ | 8 |

TABLE 8-continued

HC/LC Sequences of PSMA X CD3 bispecific antibody (PS3B27) with corresponding SEQ ID NOs

| PS3B27 | Heavy Chain | SEQ ID NO | Light Chain | SEQ ID NO |
|---|---|---|---|---|
| | PPCPAPEAAGGPSVFLFPPKPKDT LMISRTPEVTCVVVDVSQEDPEV QFNWYVDGVEVHNAKTKPREEQ FNSTYRVVSVLTVLHQDWLNGK EYKCKVSNKGLPSSIEKTISKAKG QPREPQVYTLPPSQEEMTKNQVS LTCLVKGFYPSDIAVEWESNGQP ENNYKTTPPVLDSDGSFFLYSRLT VDKSRWQEGNVFSCSVMHEALH NHYTQKSLSLSLGK | | GLSSPVIKSENRGEC | |
| CD3 Arm (CD3B219) | EVQLVESGGGLVQPGGSLRLSCA ASGFTENTYAMNWVRQAPGKGL EWVARIRSKYNNYATYYAASVK GRFTISRDDSKNSLYLQMNSLKTE DTAVYYCARHGNFGNSYVSWFA YWGQGTLVTVSSASTKGPSVFPL APCSRSTSESTAALGCLVKDYFPE PVTVSWNSGALTSGVHTFPAVLQ SSGLYSLSSVVTVPSSSLGTKTYT CNVDHKPSNTKVDKRVESKYGPP CPPCPAPEAAGGPSVFLEPPKPKD TLMISRTPEVTCVVVDVSQEDPEV QFNWYVDGVEVENAKTKPREEQ FNSTYRVVSVLTVLHQDWLNGK EYKCKVSNKGLPSSIEKTISKAKG QPREPQVYTLPPSQEEMTKNQVS LTCLVKGFYPSDIAVEWESNGQP ENNYKTTPPVLDSDGSFLLYSKLT VDKSRWQEGNVFSCSVMHEALH NHYTQKSLSLSLGK | 17 | QTVVTQEPSLTVSPGGTVTL TCRSSTGAVTTSNYANWVQ QKPGQAPRGLIGGTNKRAPG TPARFSGSLLGGKAALTLSG VQPEDEAEYYCALWYSNLW VEGGGTKLTVLGQPKAAPS VTLFPPSSEELQANKATLVC LISDFYPGAVTVAWKADSSP VKAGVETTITSKQSNNKYA ASSYLSLTPEQWKSHRSYSC QVTHEGSTVEKTVAPTECS | 18 |

TABLE 9

VH and VL chain sequences of PSMA x CD3 bispecitic antibody (PS3B27) with corresponding SEQ ID NOs.

| mAb ID | Heavy Chain Amino acid sequence | SEQ ID NO | Light Chain Amino Acid Sequence | SEQ ID NO |
|---|---|---|---|---|
| PSMA Arm (PSMB127) | EVQLLESGGGLVQPGGSLRLSC AASGFTFKSDAMHWVRQAPGK GLEWVSEISGSGGYTNYADSVK GRFTISRDNSKNTLYLQMNSLR AEDTAVYYCARDSYDSSLYVG DYFDYWGQGTLVTVSS | 5 | EIVLTQSPATLSLSPGERATL SCRASQSVSSYLAWYQQKP GQAPRLLIYDASNRATGIPA RFSGSGSGTDFTLTISSLEPE DFAVYYCQQRSNWPLTFGQ GTKVEIK | 6 |
| CD3 Arm (CD3B219) | EVQLVESGGGLVQPGGSLRLSC AASGFTFNTYAMNWVRQAPGK GLEWVARIRSKYNNYATYYAA SVKGRFTISRDDSKNSLYLQMN SLKTEDTAVYYCARHGNFGNS YVSWFAYWGQGTLVTVSS | 15 | QTVVTQEPSLTVSPGGTVTL TCRSSTGAVTTSNYANWVQ QKPGQAPRGLIGGTNKRAPG TPARFSGSLLGGKAALTLSG VQPEDEAEYYCALVVYSNLW VFGGGTKLTVL | 16 |

TABLE 10

CDR sequences of PSMA x CD3 bispecific antibody (PS3827) with corresponding SEQ ID NOs.

| CDR | PSMA arm (PSMB127) | SEQ ID NO: | CD3 Arm (CD3B219) | SEQ ID NO: |
|---|---|---|---|---|
| HCDR1 | SDAMH | 9 | TYAMN | 19 |
| HCDR2 | EISGSGGYTNYADSVKG | 10 | RIRSKYNNYATYYAASV | 20 |
| HCDR3 | DSYDSSLYVGDYFDY | 11 | HGNFGNSYVSWFAY | 21 |
| LCDR1 | RASQSVSSYLA | 12 | RSSTGAVTTSNYAN | 22 |

TABLE 10-continued

CDR sequences of PSMA x CD3 bispecific antibody (PS3827) with corresponding SEQ ID NOs.

| CDR | PSMA arm (PSMB127) | SEQ ID NO: | CD3 Arm (CD3B219) | SEQ ID NO: |
|---|---|---|---|---|
| LCDR2 | DASNRAT | 13 | GTNKRAP | 23 |
| LCDR3 | QQRSNWPLT | 14 | ALWYSNLWV | 24 |

Example 5. Binding of PSMAxCD3 Bispecific to PSMA Positive Cell Lines

PSMAxCD3 bispecific antibodies were tested for binding to PSMA positive cell lines LNCAP, human PSMA-HEK, Chimpanzee-PSMA-HEK and Cynomolgous monkey PSMA-HEK. Bound antibody was detected by an anti-human kappa light chain PE conjugated detection reagent (Invitrogen). The Mean Fluorescents Intensity (MFI) was the measure of bound bispecific antibody. The MFI was converted to a relative $EC_{50}$. $EC_{50}$ is a commonly used dose-response curve, where the half maximal effective concentration or the $EC_{50}$ point is defined as the inflection point of the curve. $EC_{50}$ values were determined by measuring cell bound bispecific and known concentrations. High concentrations resulted in maximum target antigen binding i.e. full binding saturation. The dose response curves were then diluted down to that of background or no bispecific binding. The inflection point of this curve reflects the $EC_{50}$ point. The calculated $EC_{50}$ is determined by taking the ug/ml amount of bispecific antibody at the $EC_{50}$ point and converting it to a molarity value based on the MW of the bispecific antibody. Bispecific antibodies were normalized for protein concentration and then incubated with the same number of cells expressing either human or cyno PSMA. The MFI at each concentration was collected by flow cytometry and plotted as a function of concentration. Data was transformed via log 10 and then plotted. Nonlinear regression of binding curves was done to determine $EC_{50}$ values. Cell based binding $EC_{50}$ values and calculated $EC_{50}$ values of PS3127 for whole cell using LNCaP, cyno and chimp PSMA-expressing cell lines are shown in Table 11.

TABLE 11

| | Cell Based Binding $EC_{50}$ values. | | | | | |
|---|---|---|---|---|---|---|
| | LNCaP | | Cyno-PSMA-HEK | | Chimp-PSMA-HEK | |
| Ab | $EC_{50}$ (ug/mL) | Calculated $EC_{50}$ (nM) | $EC_{50}$ (ug/mL) | Calculated $EC_{50}$ (nM) | $EC_{50}$ (ug/mL) | Calculated $EC_{50}$ (nM) |
| PS3B27 | 2.07 | 14.6 | 1.403 | 9.9 | 3.24 | 22.83 |

Example 6. Affinity of PSMAxCD3 Bispecific Antibody to Recombinant PSMA Protein To further evaluate the antibodies, the rates of chimp PSMA ECD association and dissociation were measured for the hits that were carried forward from Cell-binding assays. The interactions of PSMAxCD3 bispecific mAbs with target (recombinant Chimp, PSMA) were studied by Surface Plasmon Resonance (SPR) using a ProteOn XPR36 system (BioRad). A biosensor surface was prepared by coupling anti-Human IgG Fc (Jackson ImmunoResearch Laboratory, cat #109-005-098) to the modified alginate polymer layer surface of a GLC chip (BioRad, cat #176-5011) using the manufacturer instructions for amine-coupling chemistry. Approximately 4400 RU (response units) of anti-Human IgG Fc antibodies were immobilized. The kinetic experiments were performed at 25° C. in running buffer (DPBS+ 0.03% P20+100 µg/ml BSA). To perform kinetic experiments, 100 RU of bispecific antibodies were captured followed by injections of analytes (recombinant Chimp PSMA ECD) at concentrations ranging from 3.7 nM to 300 nM (in a 3-fold serial dilution). The association phase was monitored for 3 minutes at 50 µL/min, then followed by 15 minutes of buffer flow (dissociation phase). The chip surface was regenerated with two 18 second pulses of 100 mM Phosphoric acid ($H_3PO_4$, Sigma, cat #7961) at 100 µL/min.

The result for each bispecific antibody was reported in the format of $k_a$ (On-rate), $k_d$ (Off-rate) and $K_D$ (equilibrium dissociation constant). Results are shown in Tables 14.

TABLE 12

Summary of kinetics and affinity of PS3B27 (PSMB127 x CD3B219) to recombinant human PSMA, recombinant chimp PSMA and recombinant cyno PSMA (3.7-300 nM). The parameters reported in this table were obtained from a 1:1 Langmuir binding model. Affinity, $K_D = k_d/k_a$.

| Recombinant PSMA | Bispecific Ab Protein ID | $k_a$ (1/Ms) $10^5$ | $k_d$ (1/s) $10^{-03}$ | $K_D$ (nM) |
|---|---|---|---|---|
| Human PSMA | PS3B27 | 2.87 ± 0.36 | 2.89 ± 0.70 | 10.3 ± 3.2 |
| Chimp PSMA | PS3B27 | 2.08 ± 0.38 | 1.56 ± 0.37 | 7.48 ± 0.97 |
| Cyno PSMA | PS3B27 | 1.59 ± 0.12 | 1.10 ± 0.04 | 7.00 ± 0.68 | n = 3 independent experiments with 2 replicates. Results listed as average ± standard deviation.

Example 7. T-Cell Activation by PS3B27 in PSMA Positive Cell Lines

Figure 5:
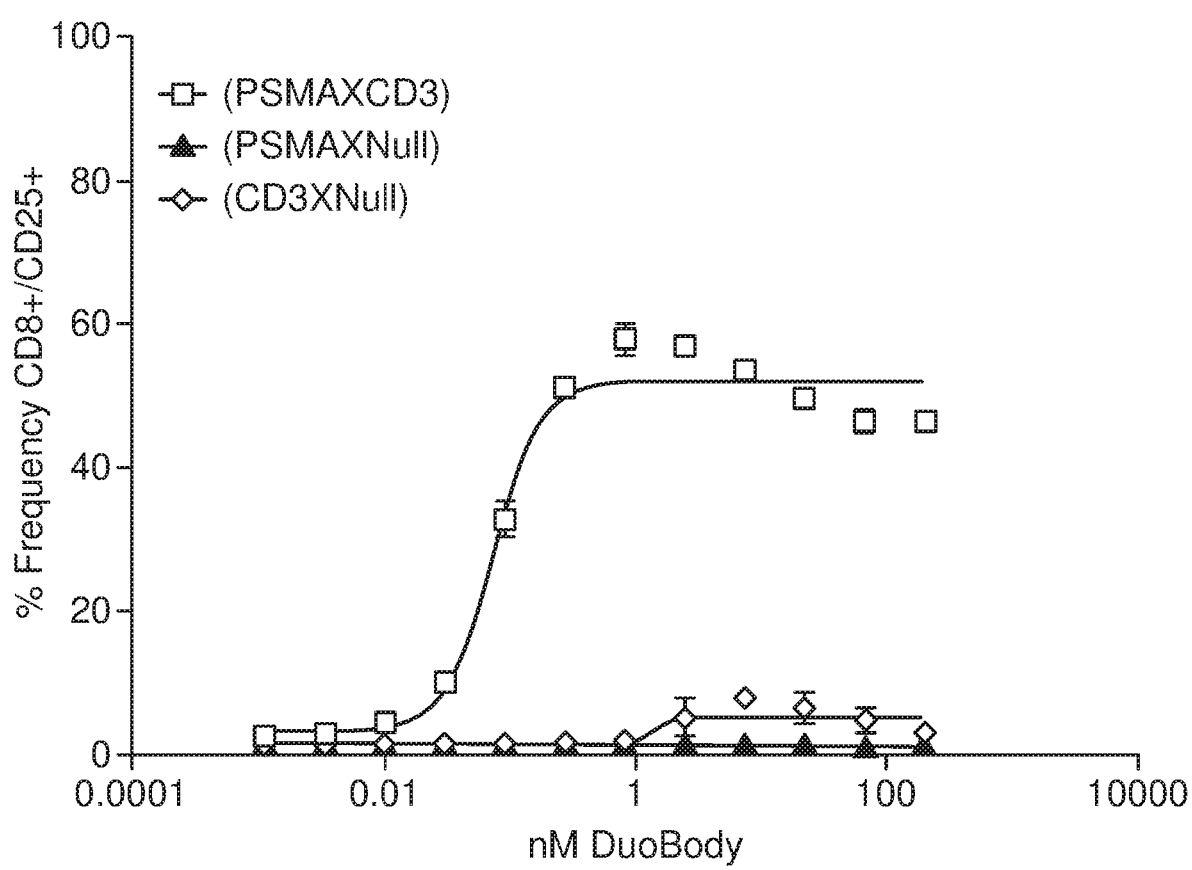
FIG. 5 shows T-cell activation by PS3B27.

Purified Pan3+ T-cells were obtained from normal, healthy donors by Biological Specialty Corporation by negative selection of leukapheresed white blood cells and stored frozen at −80° C. or in Liquid Nitrogen until ready for use. Naïve, unactivated T-cells were combined with target cells and CD3xPSMA bispecific antibodies or null controls (CD3xNull or PSMAxNull) at a 3:1 Effector:Target ratio. Following a 48-hour incubation, supernatants were analyzed for cytokine secretion by sandwich enzyme-linked immunosorbent assay (ELSA) (Meso Scale Discovery). Expression of the T-cell activation marker CD25 was measured by flow cytometry by staining T-cells for CD45, CD8, CD25, and a live/dead near-IR stain. Populations of CD8+/CD25+ were determined by first gating on a gross cell population (FSC-A vs. SSC-A) to exclude debris and cell aggregates. The cell gate subset was further narrowed for cells determined to be live, by exclusion of the live/dead stain. Live cells were then gated for CD45+/CD8+ cells. Finally, the CD8+/CD25+ positive subset was identified. The EC50 of PS3B27 or control was derived by plotting the percentage of CD8+/CD25+ against Log 10 nM bispecific antibody or control, followed by a Non-linear regression (4 Parameter fit, least squares method)(FIG. 5). All data analysis was performed in GraphPad Prism.

Example 8. Anti-Tumor Efficacy of in Tumorigenesis Prevention of HEK293-PSMA Xenografts in PBMC-Humanized NSG Mice Efficacy of PS3B27 (PSMA×CD3 Bispecific antibody) was evaluated by prevention of tumorigenesis (prophylactic model) of HEK293-PSMA human xenografts using inoculated human donor peripheral blood mononuclear cells (PBMC) in male NSG mice (NOD.Cg-Prkdc$^{scid}$IL2rg$^{tm1Wjl}$/SzJ or NOD SCID Gamma, Jackson Laboratories, Bar Harbor, Me.). Mice were injected intravenously (iv) in the lateral tail vein with $1\times10^7$ human PBMCs 7 days prior to tumor cell implantation. Mice were subsequently implanted subcutaneously (sc) with $1\times10^7$ HEK293-PSMA cells in the right hind flank. Beginning on the day of tumor implantation PBS (phosphate buffered saline) control, PS3B27, CD3B288 (CD3×Null) or PS3B46 (PSMA×Null) were administered iv at 0.4 mg/kg q2d-q3d for a total of 5 doses on days 0, 3, 5, 7 and 10.

Tumor volume was calculated using the formula: Tumor Volume (mm$^3$)=(a×b$^2$/2); where 'a' represents the length, and 'b' the width of the tumor as determined by caliper measurements and monitored twice weekly throughout the study. Percent tumor growth inhibition (TGI) was defined as the difference between mean tumor volumes of the treated and control (PBS) groups, calculated as TGI=[((TVc−TVt)/TVc)*100] where TVc is the mean tumor volume of a given control group and TVt is the mean tumor volume of the treated group. As defined by NCI criteria, ≥60% TGI is considered biologically significant (Johnson, et al (2001) Br J Cancer 84(10) 1424-31). Animals were removed from studies when a maximum tumor volume of 1500 mm$^3$ was reached.

Engraftment of human PBMC eventually leads to graft-versus-host disease (GvHD) in the mice, where the engrafted donor T cells become activated and infiltrate the host tissues, leading to body weight loss, organ failure, and inevitably, death. To monitor the onset and severity of GvHD, body weight was recorded twice weekly and expressed in grams (g). Percent body weight change was calculated using the formula: Body weight change=[((B$_t$−B$_0$)/B$_0$)*100] where B is the body weight on a given day of study and B$_0$ is the body weight at the initiation of treatment. Animals with sustained body weight loss greater than 20% of the initial body weight were considered moribund and removed from the study.

Figure 6:
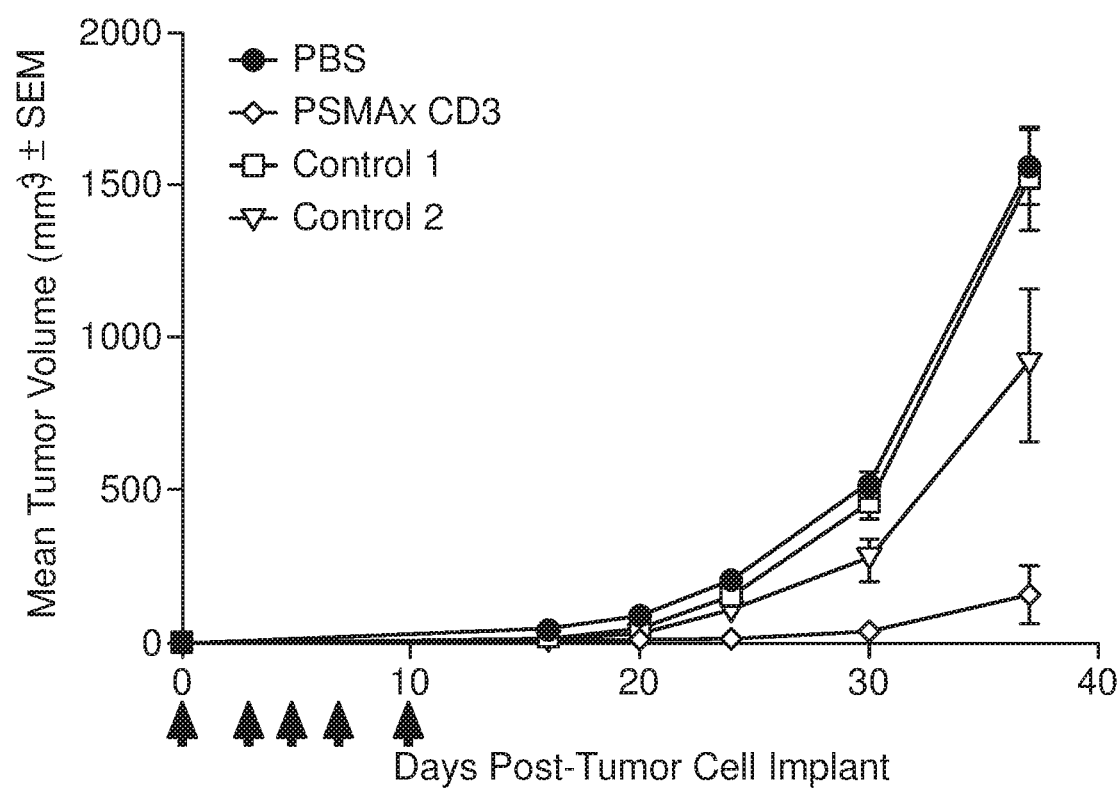
FIG. 6 shows prevention of tumorigenesis of HEK293-PSMA xenografts treated with PS3B27 or control bispecific antibodies in PBMC humanized NSG mice.

Statistical significance was evaluated using a 1-way ANOVA with multiple comparisons using Dunnett's multiple comparisons test using Graph Pad Prism software. PS3B27 treatment effectively delayed HEK293-PSMA tumorigenesis and tumor growth (FIG. 6). Small but palpable HEK293-PSMA tumors were detectable in seven of eight mice in the PBS treated group on study day 16 (6 days post last therapeutic treatment), whereas only one mouse out of eight in the PS3B27 treated group had a tumor. Five out of eight mice had palpable tumors in the CD3B288 treatment group and two out of eight mice had small tumors in the PS3B46 group. Tumor growth inhibition was assessed 27 days following cessation of treatment (day 37 post-tumor implantation), when each group had a minimum of 7 animals. Tumor growth in the PSMA×CD3 bispecific antibody (PS3B27) treated group was inhibited by 90% as compared to PBS-treated controls (n=8/group, p<0.001). The PSMA×Null bispecific antibody (PS3B46) also inhibited tumorigenesis and growth in a statistically significant fashion (TGI=42%, n=7) vs. PBS control, (p<0.05), although it was not considered to be a biologically significant effect based on NCI criteria.

Figure 7:
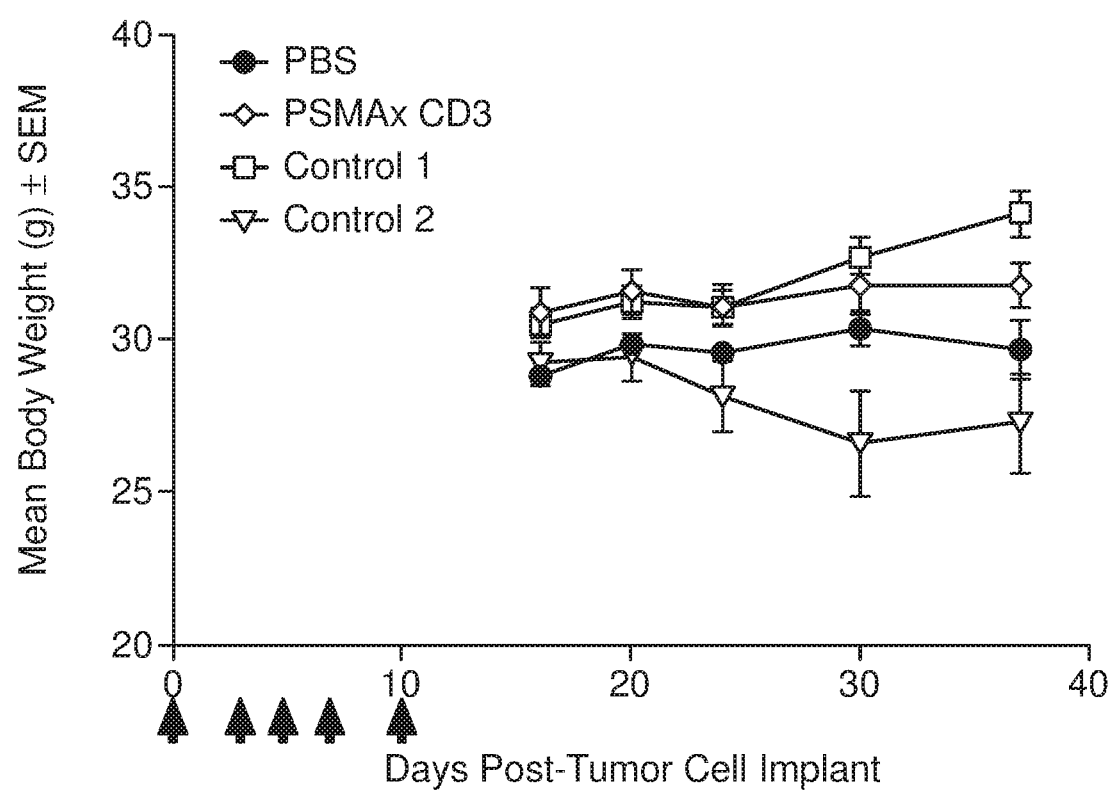
FIG. 7 shows mean body weights of PBMC-humanized NSG mice bearing HEK293-PSMA xenografts with PS3B27 and control bispecific antibody treatment.

Animal groups receiving PBMCs eventually succumb to progressive GvHD, however body weight loss was slight in the current study. No significant difference was observed between mean body weights of animals treated with 0.4 mg/kg PS3B27vs PBS as shown in FIG. 7 up to day 37 post-tumor implant (p>0.05). Therefore PS3B27-mediated T cell redirection did not further contribute towards GvHD-related body weight loss.

Despite minor weight loss in the current study, sporadic GvHD-related deaths were noted. One mouse in the PSMA× Null bispecific antibody PS3B46 group was euthanized due to excessive GVHD-related (>20%) body weight loss on day 30-post tumor implant. By day 42 post-tumor implant, additional GvHD-related deaths were noted in the PBS (n=1), and PSMA×Null bispecific antibody PS3B46 groups (n=2), and several additional mice were removed from the study due to reaching the 1500 mm$^3$ tumor volume endpoint, at which time the entire study was terminated.

Example 9. Efficacy of PS3B27 in Tumorigenesis Prevention of Admixture HEK293-PSMA/T Cell Xenografts in Male CD1 Node Mice Efficacy of PS3B27 was evaluated in an admixture xenograft model where human CD3+ pan T cells and tumor cells were co-injected into male CD1 nude mice (NU-Foxn1nu, Charles River Laboratories, Wilmington, Mass.).

Human PSMA×human CD3 bispecific antibody PS3B27, or control bispecific antibodies were administered iv every 2-3 days (q2d or q3d) for a total of 5 doses as indicated. Mice were monitored (body weight and tumor caliper measurement) twice weekly throughout the studies. Drug doses expressed as μg/animal were converted to mg/kg based on a 25 g body weight (example: 10 μg/animal=0.4 mg/kg). Drug doses administered as mg/kg, were dosed 10 mL/kg based on body weight (example: 25 g mouse=0.25 mL).

Tumor volume was calculated using the formula: Tumor Volume (mm3)=(a×b2/2); where 'a' represents the length, and 'b' the width of the tumor as determined by caliper measurements and monitored twice weekly throughout the study. Percent tumor growth inhibition (TGI) was defined as the difference between mean tumor volumes of the treated and control (PBS) groups, calculated as TGI=[((TVc−TVt)/TVc)*100] where TVc is the mean tumor volume of a given control group and TVt is the mean tumor volume of the treated group. As defined by NCI criteria, ≥60% TGI is considered biologically significant [1]. Animals were removed from studies when a maximum tumor volume of 1500 mm$^3$ was reached.

The tolerability of PS3B27 could not be assessed with respect to CD3 binding in host tissues due to lack of cross-reactivity of the CD3 arm to corresponding mouse antigens. The T cell injected with the tumor cells do however express human CD3 and can bind PS3B27 and CD3×Null controls. Percent body weight change was calculated using the formula: Body weight change=[((Bt B0)/B0)*100] where Bt is the body weight on a given day of study and B0 is the body weight at the initiation of treatment.

Statistical significance was evaluated using a 1-way ANOVA with multiple comparisons using Dunnett's multiple comparisons test using Graph Pad Prism software.

Efficacy of PS3B27 was evaluated by prevention of tumorigenesis of admixture xenografts containing HEK293-PSMA cells and activated and expanded CD3 positive pan T-cells in a 1:5 effector to target ratio in male CD1 nude mice (ELN ref: CD3-PSMA-2013-00003). T-cells were activated and expanded in vitro using the T-cell activation/expansion kit in IL-2 containing media (Miltenyi Biotech, Auburn, Calif., catalog #130-091-441, 130-097-743) for 12 days. Mice were implanted sc with an admixture of 5×106 HEK293-PSMA cells and 1×106 activated and expanded T-cells per mouse in 50% Cultrex (Trevigen, Gaithersburg, Md., catalog #3433-005-01) and 50% serum-free RPMI 1640 media in the right hind flank. Beginning on the same day as tumor implantation, PBS, PS3B27 at 0.005-0.5 mg/kg, CD3B288 (CD3×Null bispecific antibody) 0.5 mg/kg or PS3B46 (PSMA×Null bispecific antibody) 0.5 mg/kg were administered iv, by body weight, q2d-q3d for a total of 5 doses on days 0, 2, 4, 7 and 9. (n=10/group). Treatment with PS3B27 was also evaluated with ip administration (data not shown). One animal was removed each on days 46 and 49 in the PBS control group for excessive tumor burden. Tumor volume data was plotted up to day 64 after which half of the control animals were removed from study due to excessive tumor volume.

Figure 8:
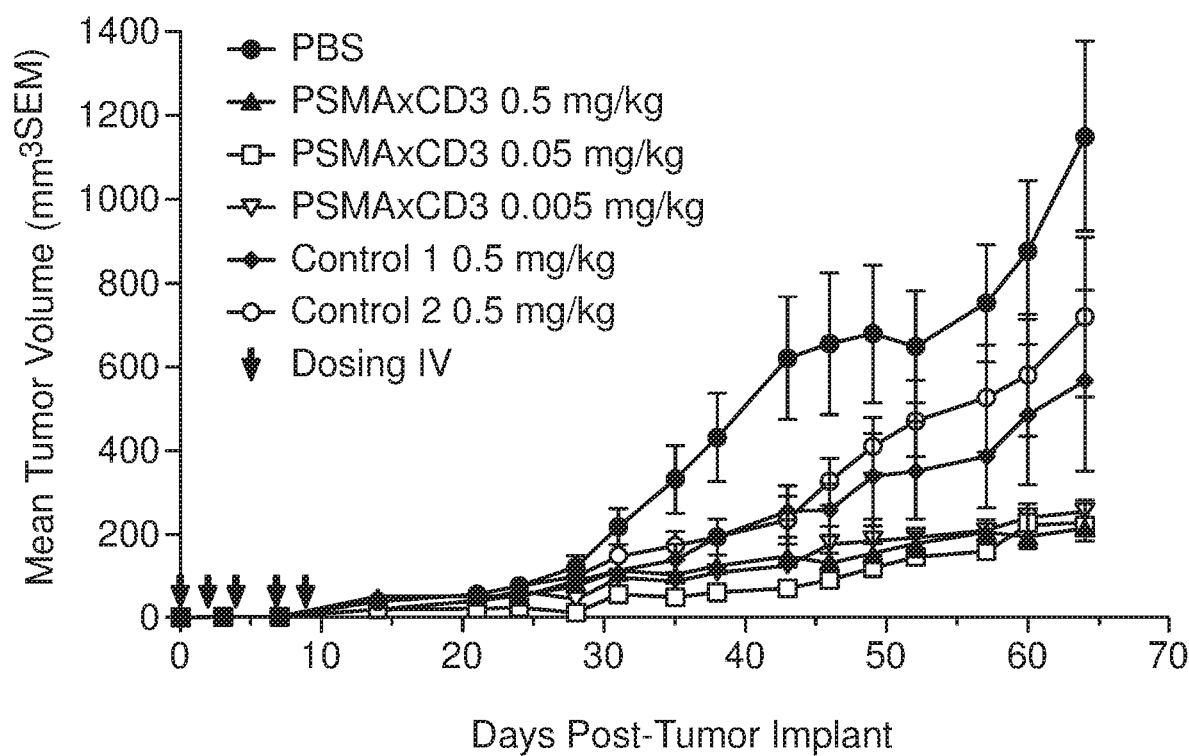
FIG. 8 shows efficacy of PS3B27 and control bispecific antibodies in tumorigenesis prevention of admixture HEK293-PSMA/T cell xenografts in male CD1 nude mice.

As shown in FIG. 8, tumorigenesis and growth were evaluated for 55 days following cessation of treatment (up to day 64). Treatment with PS3B27 significantly inhibited tumorigenesis and delayed growth compared to PBS control at all doses (0.005, 0.05 or 0.5 mg/kg) resulting in TGI of 73%, 81% and 82%, respectively (p<0.001, P<0.0001, P<0.001, respectively) on day 64. Treatment of PS3B27 by ip administration showed similar efficacy as iv administration (data not shown). Animals treated with CD3B288 (CD3×Null bispecific antibody) or PS3B46 (PSMA×Null Bispecific antibody) showed some anti-tumor activity with 51% and 38% TGI, respectively on day 64 (p<0.05, p=ns, respectively), however this is not considered biologically significant based on the NCI criteria of 60% TGI, demonstrating the requirement for both CD3 and PSMA binding of the bispecific antibody to achieve efficacy.

Figure 9:
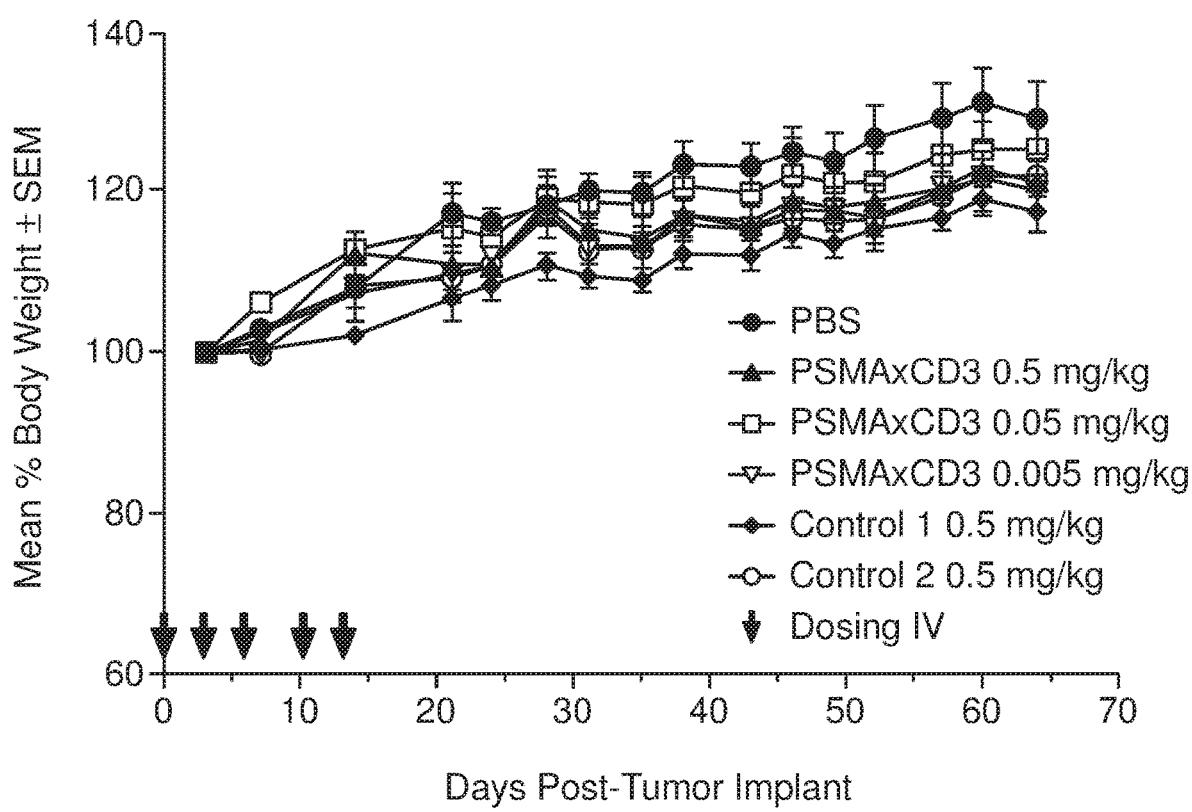
FIG. 9 shows body weight of CD1 male nude mice bearing Admixture HEK293-PSMA/T cell Xenografts Treated with PS3B27 and control bispecific antibodies.

There was no body weight loss over the course of the study, however, animals treated with PS3B27 at 0.5 and 0.005 mg/kg did have significantly less increase in body weight compared to PBS (p<0.001, p<0.0001, respectively, FIG. 9), however this could be due to a lower tumor burden in these animals.

Example 10: Toxicology Studies

Toxicological Evaluation of the Study Drug in Studies Conducted Via IV Administration.

The tolerability of IV administration of the study drug was evaluated in a single-dose/repeat-dose non-GLP exploratory toxicology study. Doses ranged from 0.03 to 3 mg/kg.) Different dose regimens were used for SA males and SM males and females. The most prominent and dose-limiting toxicity was cytokine release, which was predominantly a first-dose effect. Plasma cytokines appeared to directly correlate with mortality. Elevations in interferon (IFN)-γ, interleukin (IL)-2, IL-6, IL-10, and tumor necrosis factor (TNF)-α were observed primarily at 20.06 mg/kg (Q3D or Q1W). At non-tolerated doses (≥0.1 mg/kg) animals were either found dead or euthanized due to adverse effects, predominately between Day 1 and Day 2 of the first dose. The cause of death in all early decedents could not be determined histologically and was presumed to be due to severe cytokine release. The microscopic findings on the scheduled day of necropsy (Day 30) for monkeys in the 0.06 (Q3D and Q1W) and 0.3 mg/kg (Q1W) cohorts included mononuclear infiltrates in liver, kidney, and gallbladder; minimal to mild renal tubular degeneration/regeneration; minimal multifocal renal tubular mineralization; mononuclear interstitial infiltrates around the tubular findings or large vessels; and mild bone marrow hypercellularity. The maximum tolerated dose in SM males (most sensitive to the study drug-induced cytokine release) was 0.06 mg/kg (Q3D or Q1W). There was loss of exposure (apparently due to ADAs) in the majority of animals dosed beyond 2 weeks, and as a result, the duration of subsequent studies was limited to 2 weeks.

In the pivotal GLP study in SM *cynomolgus* monkeys, the study drug was administered by IV slow bolus injections Q1W (3 total doses) or Q3D (6 total doses) for 2 weeks due. The Q3D doses administered to males were 0, 0.03, or 0.06 mg/kg. Females received 0, 0.06, or 0.2 mg/kg. The Q1W doses for males were 0.06 mg/kg and for females were 0.2 mg/kg. Generally, dose-related increases in cytokine plasma concentrations were observed in both male and female monkeys at dose levels ≥0.03 mg/kg. Emesis (0.06 mg/kg Q3D and 0.2 mg/kg Q3D/Q1W) and hunched posture (0.03 and 0.06 mg/kg Q3D) were primarily associated with administration of the first dose. The clinical signs were considered to be related to cytokine release. One of 5 females (0.2 mg/kg Q1W) was euthanized on Day 3 due to declining clinical condition, and the cause was likely due to severe cytokine release. In animals that successfully completed dosing, there were no the study drug-related macroscopic changes, but microscopic findings (from scheduled necropsy on Day 16/17) were observed at ≥0.03 mg/kg. The findings were limited to lymphocytic infiltration noted in the perivascular regions of the kidney (minimal to mild), liver (minimal to moderate), and gallbladder (mild), which reversed by the end of recovery period on Day 57, except for mild perivascular infiltrate, in the kidney of 1 female (0.2 mg/kg; Q3D). The highest non-severely toxic dose (HN-STD) in the pivotal study was 0.06 mg/kg/dose. The corresponding mean Cmax for monkeys administered Q3D (males and females) or Q1W (males) was 1.85 or 1.99 µg/mL, and the AUCDay1-4 or AUCDay1-8 was 1.72 or 2.37 µg-day/mL, respectively, following dosing on Day 1.

A non-GLP investigative toxicology study was conducted to determine if the dose-limiting cytokine release seen in previous studies could be mitigated. Two approaches were tested, which included intra-animal dose escalation following priming with a low dose (0.01 mg/kg) or prophylactic treatment with tocilizumab (an IL-6 receptor antagonist). In the low dose priming study phase, the study drug was administered Q3D via IV slow bolus injection as either a slow intra-animal dose escalation scheme (0.01→0.02→0.04→0.12→0.6 mg/kg) (FIG. 10A) or a rapid intra-animal escalation scheme (0.01→0.03→0.1→0.4→41.5 mg/kg)(FIG. 10B).

Clinical Pathological Changes Across Studies Conducted Via IV Administration

A cross study analysis in male and female *cynomolgus* monkeys was conducted comparing the clinical pathology changes associated with IV administration of the study drug in the single-dose/repeat-dose non-GLP exploratory study, the pivotal GLP toxicology study (T-2015-072), and the non-GLP investigative study.

Changes in clinical pathology parameters were generally similar across all 3 studies (and did not correlate with the presence or severity of clinical signs for individual animals, including animals that were euthanized early due to declining condition. These findings suggest that the clinical pathology changes themselves were generally not sensitive or specific biomarkers for the study drug-related clinical signs or overall tolerability under the conditions of these studies.

Many clinical pathology changes were most prominent after the first dose, with changes of smaller magnitude or absence of consistent changes observed following subsequent doses. The changes included decreased platelets, red blood cell mass, reticulocytes, lymphocytes and monocytes (except after escalating doses as discussed below), eosinophils, coagulation times (except after escalating doses), blood urea nitrogen (BUN), creatinine, most hepatic enzymes, and bilirubin, and changes in phosphorus and electrolytes. Several clinical pathology changes were considered to be likely associated with the study drug-related cytokine release and a pro-inflammatory state, including the acute-phase response (pro-inflammatory state associated with decreased albumin and cholesterol, and increased C-reactive protein, triglycerides, and globulins) and, possibly, changes in neutrophils, eosinophils, and basophils, prolonged coagulation times, increased bilirubin, and increased BUN and creatinine. Decreased lymphocytes in all studies were considered likely a result of expected pharmacologic activity associated with CD3 engagement. Other clinical pathology changes, including increased hepatic enzymes and decreased minerals and electrolytes.

Of these changes, decreased lymphocytes and monocytes and mildly prolonged activated partial thromboplastin time (APTT) generally persisted longer in animals undergoing dose escalation than in animals dosed repeatedly at the same dose level; the longer duration of these changes was related to intra-animal dose escalation and not necessarily related to administration of the low priming dose. Other changes generally persisted throughout the dosing phase (or began later in the dosing phase) across most studies, including the acute-phase response, increased alkaline phosphatase, increases in some leukocyte parameters (eosinophils, basophils, and large unstained cells), and decreased calcium.

Despite the improved dose level tolerability noted upon low dose priming, the effects were restricted to selected clinical pathology parameters. The most notable differences in animals undergoing low dose priming were the absence of changes in renal parameters (increased BUN, creatinine, and phosphorus) and the persistence of decreased lymphocytes and monocytes and mildly prolonged APTT. These differences suggest a priming-related effect, although the contribution of the lack of renal parameter changes to improved tolerability was uncertain. Additionally, prolonged coagulation times (most notably APTT) were generally of smaller magnitude in animals undergoing low dose priming at all doses (through 0.6 or 1.5 mg/kg) than in animals at similar doses in the absence of priming.

Local Tolerance Study Upon Subcutaneous Administration of the Study Drug

The local tolerance of SC (subcutaneous) administration of the study drug was evaluated in sexually mature male *cynomolgus* monkeys. Animals received 2 weekly doses of the study drug, 0.9% saline, or the formulation buffer (aqueous solution containing 10 mM sodium acetate, 8% sucrose, 0.04% polysorbate 20, and 0.02 mg/mL EDTA disodium at pH 5.2). Injection sites were evaluated for up to 96 hours post dose after both doses, and animals were necropsied on Day 15. There were no the study drug-related changes in clinical observations, body weights, qualitative food evaluation, gross or microscopic findings in the injection sites or draining lymph nodes. The study drug-related increases in plasma cytokine (MCP-1, IL-10, IL-6, TNF-α, IFN-γ) concentrations were observed, albeit markedly lower than that observed upon IV administration of the same dose. The study drug-related changes in clinical pathology parameters included decreased lymphocytes, monocytes, eosinophils, large unstained cells, reticulocytes, and platelets, along with an acute phase response (increased C-reactive protein and decreased albumin). These changes were transient following the first dose. Following the second dose, clinical pathology changes were limited to mildly decreased lymphocytes. The mean Cmax on days 1 and 8 was 0.28 and 0.33 ug/ml respectively, and the AUCDay0-7 or AUCDay7-14 was 1.35 and 1.58 µg/day/mL, respectively Example 11: A Phase 1, First-in-Human, Dose Escalation Study of the Study Drug in Patients with Advanced Stage Solid Tumors Abbreviations

TABLE 13

| Abbreviations used throughout this Example are as follows | |
|---|---|
| β-hCG | β human chorionic gonadotropin |
| $^{18}$F-FDG | $^{18}$F-fluorodeoxyglucose |
| $^{99m}$Tc | technetium-99m |
| ADA | anti-drug antibody |
| ALT | alanine aminotransferase |
| AR | androgen receptor |
| AST | aspartate aminotransferase |
| BiTE | bispecific T cell engager |
| BLRM | Bayesian Logistic Regression Model |
| CR | complete response |
| CRS | cytokine release syndrome |
| CSR | clinical study report |
| CT | computed tomography |
| CTC | circulating tumor cells |
| CyTOF | cytometry by time of flight |
| DLT | dose-limiting toxicity |
| DNA | deoxyribonucleic acid |
| E:T | effector to target (cell ratio) |
| eCRF | electronic case report form |
| ECG | electrocardiogram |
| ECHO | echocardiogram |
| ECOG | Eastern Cooperative Oncology Group |
| EOIV | end of intravenous flush |
| EOT | end-of-treatment |
| EWOC | Escalation with Overdose Control (principle) |
| FIH | first-in-human |
| GCP | good clinical practice |
| GGT | gamma-glutamyl transferase |
| GLP | good laboratory practice |
| GnRH | gonadotropin-releasing hormone |
| HBcAg | hepatitis B core antigen |
| HBsAg | hepatitis B surface antigen |
| HCV | hepatitis C virus |
| HIV | human immunodeficiency virus |
| HNSTD | highest non-severely toxic dose |
| ICF | informed consent form |
| IEC | Independent Ethics Committee |
| IFN | interferon |
| Ig | immunoglobulin |
| IL | interleukin |
| IPPI | investigator product preparation instructions |
| irAE | immune-related adverse event |
| IRB | Institutional Review Board |
| IRR | infusion-related reactions |
| IV | intravenous |
| Kd | affinity |
| MABEL | minimum anticipated biologic effect level |
| mCRM | modified continual reassessment method |

TABLE 13-continued

Abbreviations used throughout this Example are as follows

| | |
|---|---|
| mCRPC | metastatic castration-resistant prostate cancer |
| mTOR | mammalian target of rapamycin [inhibitors] |
| MRI | magnetic resonance imaging |
| MTD | maximum tolerated dose |
| MUGA | multigated acquisition scan |
| NCICTCAE | National Cancer Institute Common Terminology Criteria for Adverse Events |
| OS | overall survival |
| PBMC | peripheral blood mononuclear cells |
| PCWG3 | Prostate Cancer Working Group 3 |
| PFS | progression-free survival |
| PK/PD | pharmacokinetic/pharmacodynamic |
| PK/TK | pharmacokinetics/toxicokinetics |
| PQC | product quality complaint |
| PR | partial response |
| PSA | prostate specific antigen |
| PSMA | prostate-specific membrane antigen |
| Q1W | once a week |
| Q3D | once every 3 days |
| QD | daily |
| RCC | renal cell carcinoma |
| RECIST | Response Evaluation Criteria in Solid Tumors |
| RP2D | recommended Phase 2 dose |
| SET | Study Evaluation Team |
| SIPPM | site investigational product and procedures manual |
| SM | sexually mature |
| SUSAR | suspected unexpected serious adverse reaction |
| T cells | T lymphocytes |
| TCR | T cell receptor |
| TNF | Tumor necrosis factor |
| TTR | time to response |
| ULN | upper limit of normal |

Definition of Terms

TABLE 14

Terms used throughout this Example.

| | |
|---|---|
| AUC | area under the serum concentration versus time curve |
| $AUC_{(t1-t2)}$ | area under the concentration-time curve from time t1 to time t2 |
| CL | |
| $C_{max}$ | maximum observed serum concentration |
| $C_{min}$ | minimum observed serum concentration |
| $EC_{20, 50, 90}$ | drug concentration required to produce 20%, 50%, or 90% of the maximal effect |
| RA | accumulation ratio |
| $t_{1/2}$ | Apparent elimination half-life associated with the terminal slope ($\lambda_z$) of the semilogarithmic drug concentration-time curve |
| $T_{max}$ | time corresponding to the last quantifiable serum concentration |
| VSS | volume of distribution |

1. Protocol Summary 1.1. Synopsis

The study drug is a bispecific antibody developed to evaluate the therapeutic potential of targeting prostate-specific membrane antigen (PSMA) for CD3-mediated T cell redirection. the study drug is a human IgG4 antibody. The bispecific antibody was generated by controlled fragment antigen binding arm exchange from 2 antibodies: PSMB127 and CD3B219. PSMB127 is an anti-PSMA antibody originated from a whole cell panning of a phage library on a PSMA over-expressing cell line. CD3B219 is an anti-CD3ε antibody that originated from a public domain antibody, SP34, which was further humanized, and affinity matured.

PSMA is a transmembrane protein expressed in the normal prostate and its expression is increased during malignant transformation including expression on bone metastases. In addition, PSMA is over-expressed in the neovasculature of other malignant tumors. It is hypothesized that the study drug, a bispecific antibody that targets PSMA and CD3 simultaneously, will direct the body's immune cells to kill these malignant cells overexpressing PSMA. The mechanism of action of the study drug enables T cell-mediated cytotoxicity through recruitment of CD3 expressing T cells to the PSMA expressing target cells. This mechanism for cell killing is unique, which offers an opportunity to treat patients whose disease has proved resistant to current therapy.

Objectives, Endpoints and Hypothesis

TABLE 15

Objectives, endpoints and hypothesis

| Objectives | Endpoints |
|---|---|
| Primary | |
| Part 1 (Dose Escalation) Determine the recommended Phase 2 dose (RP2D) regimen and the maximum tolerated dose | Incidence and severity of adverse events, including dose-limiting toxicity |
| Part 2 (Expansion) Determine the safety of the study drug at the RP2D regimen | Incidence and severity of all adverse events |
| Secondary | |
| To assess the pharmacokinetics of the study drug following multiple IV doses. | Serum concentration-time profiles and pharmacokinetic parameters for the study drug including but not limited to $C_{max}$, $T_{max}$, $AUC_{(t1-t2)}$, $AUC_{tau}$, $C_{min}$, and accumulation ratio (RA) |
| To assess the pharmacodynamics of the study drug following multiple IV doses. | Pharmacodynamic markers including but not limited to systemic cytokine concentrations, markers of T cell activation, RO, and serum prostate specific antigen (PSA) |
| To assess the immunogenicity of the study drug. | Presence of anti-the study drug antibodies. |

Hypothesis

No formal statistical hypothesis testing will be conducted in this study. The study will evaluate the following:

Dose Escalation (Part 1): the RP2D of the study drug can be identified such that <33% of participants experience a dose-limiting toxicity (DLT).

Dose Expansion (Part 2): the study drug is safe and shows preliminary clinical activity at the RP2D.

Figure 11:
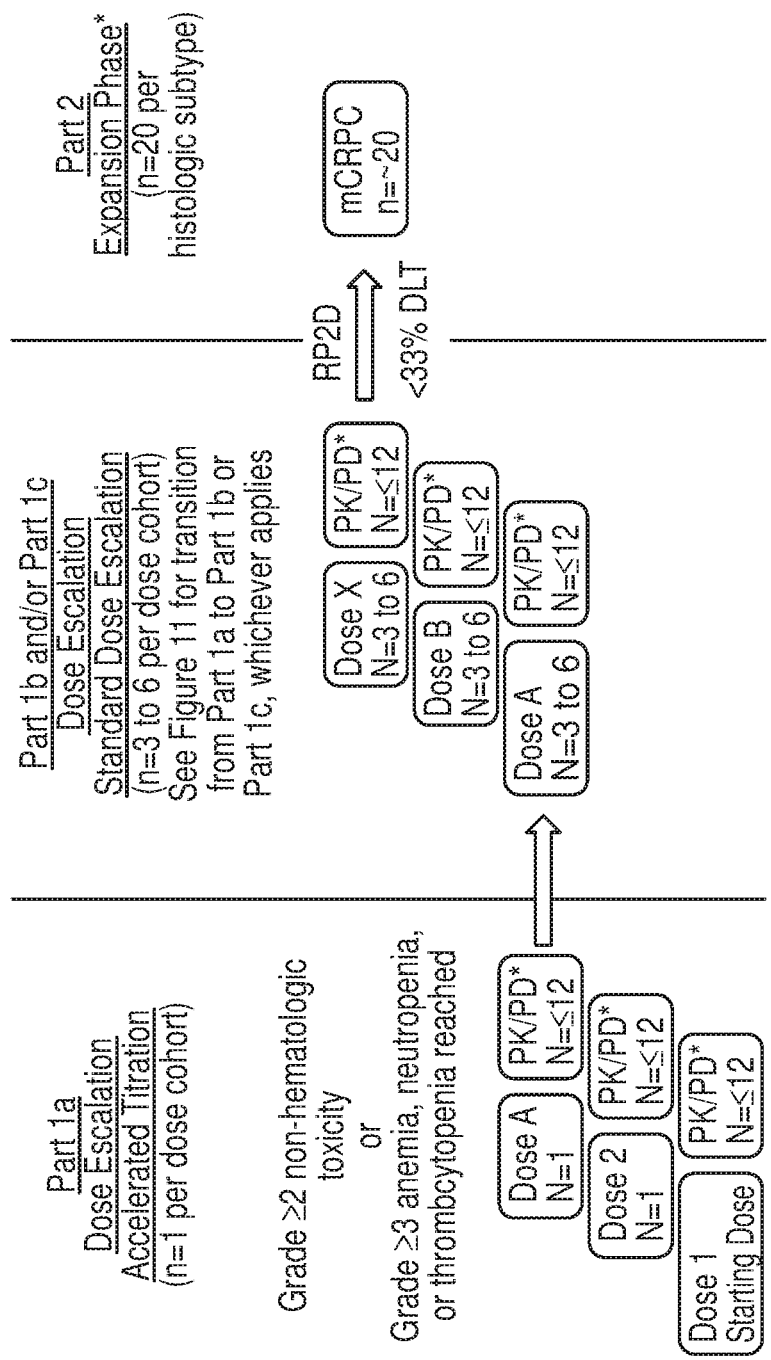
FIG. 11 shows a diagram of the dose escalation and dose expansion plan and potential exploration of a priming dose schedule—Part 1 dose escalation scheme and Part 2 dose expansion cohorts.
Figure 12:
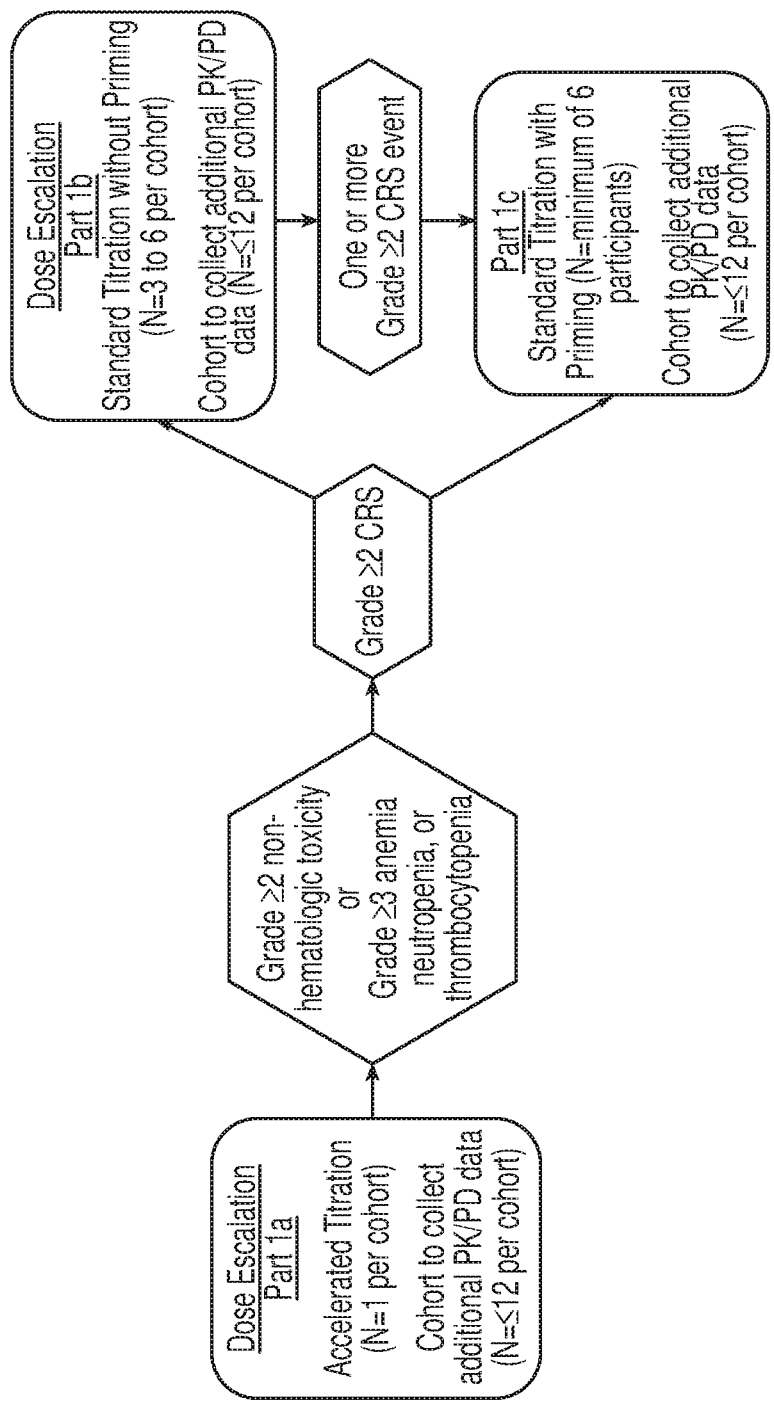
FIG. 12 shows a schematic overview of the study design—Part 1 dose escalation phase. (CRS=cytokine release syndrome; PK/PD=pharmacokinetic/pharmacodynamic)

A diagram of the dose escalation and dose expansion plan and potential exploration of a priming dose schedule is provided in FIG. 11 and FIG. 12.

Overall Design

This is a FIH, open-label, multicenter, Phase 1 study to evaluate the safety, pharmacokinetics, pharmacodynamics, and preliminary clinical activity of the study drug monotherapy in participants with advanced cancers. The study will be conducted in 2 parts: dose escalation (Part 1) and dose expansion (Part 2). In Part 1, adult men with metastatic castration-resistant prostate cancer (mCRPC) who have relapsed disease following androgen receptor (AR)-targeted therapy will be enrolled. Dose escalation will be supported by a modified continual reassessment method (mCRM) based on a statistical model, Bayesian logistic regression model (BLRM), using escalation with overdose control (EWOC) principle. The study will be initiated with accelerated titration followed by a standard titration phase. The goal of Part 1 is to determine the MTD of the study drug and to select the dose(s) and regimen(s) that will be used in Part 2, dose expansion (ie, RP2Ds). The goal of Part 2 is to further evaluate safety, pharmacokinetics, pharmacodynamics, and biomarkers (blood and tissue), as well as to assess the preliminary clinical activity of the study drug in mCRPC.

Participants will be hospitalized for 48 hours after the first 2 study drug administrations (and any priming doses, if administered) to facilitate safety monitoring and pharmacokinetic assessments. Subsequent hospitalization for study drug administration will be required for participants who meet certain safety criteria (prior Grade ≥2 neurologic toxicity, intrapatient dose escalation for priming schedules, or prior Grade ≥2 CRS that does not resolve to Grade ≤1 within 72 hours). To minimize the risk associated with anticipated infusion-related reactions (IRR), corticosteroid premedication is required prior to the first dose of study drug and will be decreased or eliminated for subsequent doses for participants who experience neither a Grade ≤1 IRR nor CRS after the first dose.

During the study, safety will be monitored by the Study Evaluation Team (SET), particularly at each dose escalation step of Part 1. The study will be initiated with a weekly dosing schedule. Alternative schedules (eg, twice weekly or priming schedules) may be explored based on emerging data as determined by the SET.

Participants will continue to receive study drug until radiographic disease progression, unequivocal clinical progression, unacceptable toxicity, withdrawal of consent, the investigator or the sponsor decision, or end of study. The end of study (study completion) is defined as the last safety assessment for the last participant on study.

Number of Participants

Approximately 70 participants will be treated in this study. However, the sample size will depend on the number of cohorts explored.

Study Drug and Duration

TABLE 16

Study Drug Duration

| | |
|---|---|
| Dose | Dose escalation will be initiated at a study drug starting dose of 0.1 µg/kg. Subsequent dose levels will be administered at a dose assigned by the sponsor using an adaptive dose escalation strategy guided by the modified continual reassessment method (mCRM) based on a statistical model, Bayesian Logistic Regression Model (BLRM) with Escalation with Overdose Control principle. |
| Route of administration | Intravenous (IV) infusion. |
| Duration of infusion | Approximately 2 hours (±30 minutes). |
| Dosing Schedule | The study will be initiated with a once weekly study drug infusion schedule (without priming). The study drug administration schedule (ie, weekly or twice weekly) may be changed and a priming dose schedule may be explored. Treatment dose schedules: Weekly: study drug treatment dose administered once weekly. There must be at least 5 days between each study drug administration. Twice weekly (if explored); study drug treatment dose administered twice weekly (ie, once every 3 to 4 days). There must be at least 72 hours between each study drug administration. Note: Study visit may occur ±2 days of the scheduled day. |

Efficacy Evaluations

Clinical activity will be assessed using the following evaluations: computed tomography (CT) scan, with contrast of neck, chest, abdomen, and pelvis; magnetic resonance imaging (MRI) (ie, for sites not adequately imaged using CT). Additional evaluations for participants with mCRPC include serum prostate specific antigen (PSA) and whole-body bone scans ($^{99m}$Tc). Evaluation of prostate treatment response will be performed according to Prostate Cancer Working Group 3 (PCWG3) criteria and Response Evaluation Criteria in Solid Tumors (RECIST) version 1.1 to evaluate progression of soft tissue lesions (CT or MRI).

Pharmacokinetic, Biomarker, and Immunogenicity Evaluations

Blood samples will be collected to characterize serum pharmacokinetics and anti-drug antibodies of the study drug. Blood samples will also be collected to evaluate pharmacodynamics, safety, and biomarkers predictive of response or resistance to the study drug treatment. Mandatory fresh tumor biopsies from accessible site of metastatic disease will be collected prior to and during the study from participants in selected PK/PD cohorts in Part 1 and in Part 2, to evaluate PSMA expression and pharmacodynamic markers in tumor tissue.

Safety Evaluations

The safety of the study drug will be assessed by physical examinations (including basic neurological assessment), ECOG performance status, clinical laboratory tests, vital signs, electrocardiograms, adverse event monitoring. Concomitant medication usage will be recorded. The severity of adverse events will be assessed using National Cancer Institute Common Terminology Criteria for Adverse Events (Version 5.0). Cytokine release syndrome has been identified as adverse event of special interest and will require enhanced reporting and data collection.

Statistical Methods

No formal statistical hypothesis testing will be conducted in this study. Dose escalation will be supported by a mCRM based on a statistical model, BLRM, with EWOC principle.

1.2. Schema

A diagram of the dose escalation and dose expansion plan and potential exploration of a priming dose schedule is provided in FIG. 11 and FIG. 12.

1.3. Schedule of Activities

TABLE 17

Schedule of Activities - Weekly Dosing Schedule Part 1 and Part 2

| Assessments/Procedures[a] | Screening ≤30 days | Week 1 Day 1 | Week 1 Day 2 | Week 1 Day 3 | Week 2 Day 1 | Week 2 Day 2 | Week 2 Day 3 | All Other Weeks Day 1 | EOT visit[m] | Post-treatment Follow-up |
|---|---|---|---|---|---|---|---|---|---|---|
| Informed consent[b] | X | | | | | | | | | |
| Eligibility criteria (Inclusion/Exclusion) | X | X | | | | | | | | |
| Demography | X | | | | | | | | | |
| Medical history | X | | | | | | | | | |
| Disease characteristics[c] | X | | | | | | | | | |
| ECOG[d] | X | X | | | X | | | X | | |
| ECHO or MUGA[d] | X | | | As clinically indicated | | | | | | |
| Physical exam[e] | X | X | | | X | | | X | | |
| Basic neurological exam[e] | X | | X | | | X | | If neurotoxicity occurred, perform for next 2 doses | | |
| Height | X | | | | | | | | | |
| 12-lead ECG[d] | X | | | | | | | | | |
| Predose | | X | | | | | | Dose 5 only | | |
| End of IV flush | | X | | | | | | Dose 5 only | | |
| Serology[f] | X | | | | | | | | | |
| Hematology[g] | X | X | X | | X | X | | X | X | |
| Chemistry[g] | X | X | X | | X | X | | X | X | |
| Coagulation[g] | X | X | X | | X | X | | X | | |
| Pregnancy test[g] | X | X | | Urine pregnancy test every 4 weeks, and as clinically indicated | | | | | X | |
| Urinalysis[g] | X | | | As clinically indicated | | | | | | |
| Vital signs including temperature and O$_2$ saturation[h] | X | X | X | X | X | X | X | X | | |
| Hospitalization See Section 4.1 and Table 24 | | At least 48 h after end of infusion (IV flush) | | | At least 48 h after end of infusion (IV flush) | | | See Table 24 for observation period requirements | | |
| Preinfusion medications[i] | | X | | | X | | | X | | |
| Study drug administration[j] | | X | | | X | | | X | | |
| Weight[j] | X | X | | | X | | | X | | |
| Fresh tumor biopsy | | | | See Table and 19 | | | | | | |
| PSA (mCRPC only)[k] | X | | | Every 4(+1) weeks after the first dose | | | | | X | |
| CT/MRI scan[k] | X | | | Every 8 weeks for first 24 weeks then every 12 weeks | | | | | | |
| Bone scan - $^{99m}$Tc (mCRPC)[k] | X | | | Every 8 weeks for first 24 weeks then every 12 weeks | | | | | | |
| PK/Immunogenicity/PD | | | | See Table 18 (Part 1) and Table 19 (Part 2) | | | | | | |
| Adverse events | | | | Continuous from signing of ICF to up to 30 days after the last dose of the study drug or until the start of subsequent anticancer therapy, if earlier (Section 8.3). | | | | | | |

TABLE 17-continued

Schedule of Activities - Weekly Dosing Schedule Part 1 and Part 2

| Assessments/ Procedures[a] | Screening ≤30 days | Week 1 | | | Week 2 Day of the Week | | | All Other Weeks Day 1 | EOT visit[m] | Post-treatment Follow-up |
|---|---|---|---|---|---|---|---|---|---|---|
| | | Day 1 | Day 2 | Day 3 | Day 1 | Day 2 | Day 3 | | | |
| Concomitant medications | Continuous from signing of ICF to up to 30 days after the last dose of the study drug or until the start of subsequent anticancer therapy, if earlier (Section 6.5). | | | | | | | | | |
| Subsequent anticancer therapy[j] | | | | | | | | | | X |
| Survival[l] | | | | | | | | | | X |

Abbreviations: $^{99m}$Tc = technetium-99; CT = computed tomography; D = day; ECG = electrocardiogram; ECHO = echocardiogram; ECOG = Eastern Cooperative Oncology Group; Ga = gallium; ICF = informed consent form; MUGA = multigated acquisition scan; O$_2$ = oxygen; PD = pharmacodynamic; PK = pharmacokinetic; PSA = prostate specific antigen; SET = Study Evaluation Team.

[a]Each planned site visit may be ±2 days from the scheduled date. Assessments and procedures (including laboratory tests) may be performed up to 48 hours prior to the scheduled study drug administration. Based on emerging data, adjustments to the planned schedule of assessments may be made by the sponsor in order to protect patient safety or fully characterize the PK or PK/PD profile of the study drug. Additional (ie, unscheduled) blood sample for cytokine profile, PK, or PD assessment may be collected up to 8 times during the first 4 cycles of treatment with the study drug.
[b]Must be signed before first study-related activity.
[c]Disease characteristics include tumor type and histology, time of diagnosis, tumor stage at diagnosis and at screening, available pathology and molecular data, prior anticancer therapies, and date of most recent disease progression.
[d]See Section 8.2.
[e]Complete physical exam at screening. A symptom- and disease-directed exam will be performed prior to all the study drug administrations. A basic neurologic examination will be performed during the physical exam at screening, prior to the first treatment dose, and any priming dose(s), and at least every 12 hours during a hospital stay. For drug administration as outpatients, neurologic examinations can be performed as clinically indicated.
[g]Laboratory assessment instructions:
Inclusion and none of the exclusion criteria presented in Section 5.1 and Section 5.2, respectively, must be met prior to first dose of the study drug.
On the study drug administration days, laboratory assessments performed within 48 hours prior to the infusion do not need to be repeated.
Additional samples may be collected and analyzed, as clinically indicated.
Laboratory assessments will be performed at a local laboratory.
Pregnancy test must be a highly sensitive serum (β human chorionic gonadotropin [β hCG]) conducted at screening and prior to the first dose of the study drug.
[h]Vital signs for the first dose of the study drug will be evaluated immediately before start of infusion, every 30 minutes during infusion, end of IV flush and 1, 2, and 3 hours after end of IV flush. All other infusions: immediately before start of infusion, every 30 minutes during infusion, end of IV flush, and as clinically indicated. Oxygen saturation and temperature are to be monitored on the same schedule as the vital signs. Monitor vital signs and O2 saturation until normalized after a CRS event.
[i]See Section 6.5.3 for instructions on medications to be administered prior to the study drug administration.
[j]Each study drug administration must be at least 5 days apart for the weekly dosing schedule. The actual dose (μg) for administration will be calculated based on the participant's weight (kg) at baseline on study Day 1 (see Table 24)
[k]See Section 8.1 for efficacy assessments. Baseline assessment acceptable if performed within 6 weeks (42 days) prior to the first dose of the study drug.
Objective response per RECIST v1.1 must have a confirmatory scan performed 4 weeks later.
If the study drug is discontinued prior to the onset of disease progression, disease evaluation should continue to be performed per local standard of care (see Section 8).
The same methodology used at baseline to evaluate disease status should be used throughout the study.
Disease assessments should not be delayed if there is a delay in the study treatment schedule.
[l]Information may be obtained via telephone contact every 12 weeks after the study drug discontinuation until one of the discontinuation criteria in Section 7.2 is met.
[m]End-of-treatment visit completed ≤30 (+7) days after the last dose of the study drug and prior to the start of a new anticancer therapy, whichever comes first (see Section 8 for end-of-treatment visit instructions).

TABLE 18

Schedule of Activities for Biomarker, Pharmacokinetic, and Immunogenicity Samples - Weekly Dosing Schedule Part 1

| Weekly Dosing Part 1 | | | Tumor biopsy[c] | T cell activation/ exhaustion; TBNK[d] | Cytokine profile[e] | TCR seq | PK[e] | Immuno-genicity[e] | RO[f] |
|---|---|---|---|---|---|---|---|---|---|
| | | | | | Sample[a,b] | | | | |
| Dose | Time | Window | Fresh tumor | Whole blood | Serum | Whole blood | Serum | Serum | Whole Blood |
| | Screening | | X | | | | | | |
| Dose 1 | Predose | −4 hours | | X | X | X | X | X | X |
| | EOF | ±15 min | | | X | | X | | |
| | 2 h | ±15 min | | | X | | X | | X |
| | 6 h | ±30 min | | | X | | X | | |
| | 24 h | ±2 hours | | X | X | | X | | X |
| | 72 h[g] | ±2 hours | | X | | | X | | X |
| Dose 2 | Predose | −4 hours | | X | X | X | X | | X |
| | EOF | ±15 min | | | X | | X | | |
| | 2 h | ±15 min | | | X | | X | | |
| | 24 h | ±2 hours | | | X | | X | | |
| Dose 3 | Predose | −4 hours | X | X | X | | X | X | X |
| | EOF | ±15 min | | | X | | X | | X |

TABLE 18-continued

Schedule of Activities for Biomarker, Pharmacokinetic, and Immunogenicity Samples - Weekly Dosing Schedule Part 1

| Weekly Dosing Part 1 | | | Tumor biopsy[c] | T cell activation/ exhaustion; TBNK[d] | Cytokine profile[e] | TCR seq | PK[e] | Immuno-genicity[e] | RO[f] |
|---|---|---|---|---|---|---|---|---|---|
| | | | | | Sample[a,b] | | | | |
| Dose | Time | Window | Fresh tumor | Whole blood | Serum | Whole blood | Serum | Serum | Whole Blood |
| Dose 4 | Predose | −4 hours | X[c] | X | X | X | X | | |
| | EOF | ±15 min | | | X | | X | | |
| Dose 5 | Predose | −4 hours | | | X | | X | X | |
| | EOF | ±15 min | | | X | | X | | |
| | 2 h | ±15 min | | | | | X | | |
| | 6 h | ±30 min | | | | | X | | |
| | 24 h | ±2 hours | | | | | X | | |
| | 72 h[g] | ±2 hours | | | | | X | | |
| Dose 6 | Predose | −4 hours | | X | | X | X | | X |
| | EOF | ±15 min | | | | | X | | X |
| Dose 7 | Predose | −4 hours | | | | | X | | |
| | EOF | ±15 min | | | | | X | | |
| Dose 8 | Predose | −4 hours | | X | | X | X | | |
| | EOF | ±15 min | | | | | X | | |
| Doses 9, 13, 17[h] | Predose | −4 hours | | | | | X | X | |
| | EOF | ±15 min | | | | | X | | |
| EOT | | | | X | X | X | X | X | X |
| Post-treatment at 4 and 8 weeks after the last dose of the study drug. | | | | | | | X | X | |

Abbreviations: CRS = cytokine release syndrome; DLT = dose-limiting toxicity; EOF = end of intravenous flush; EOT = end of treatment; h = hour; IRR = infusion-related reaction; seq = sequencing; PBMC = peripheral blood mononuclear cells; PK = pharmacokinetic; RO = receptor occupancy; SET = study evaluation team; TCR = T cell receptor; TBNK = T cells, B cells, natural killer cells.
[a]All reasonable attempts should be made to collect samples within ±10% of the planned sampling time (ie, calculated from the end of IV flush) and the time of collection must be recorded.
[b]Samples will be shipped to laboratories designated by the sponsor; the analysis will be conducted by the sponsor. Repeat or unscheduled samples (ie, pharmacokinetic, pharmacodynamic, biomarkers) may be taken for safety reasons or for technical issues with the samples.
[c]Participants with accessible lesions enrolled in selected PK/PD cohorts in Part 1 and in Part 2 must agree to undergo the mandatory fresh tumor biopsies, unless collection of the biopsy presents a safety risk.
The fresh biopsy at screening maybe collected within 6 weeks (42 days) before the first dose of the study drug provided no active anticancer treatment was initiated during this time.
The post-treatment tumor biopsy sample collection time (ie, after the completion of the DLT evaluation period and between 4 to 8 weeks after the start of treatment) may be changed by the SET based on emerging data.
The samples will be sent to a central laboratory designated by the sponsor (see Laboratory Manual for details).
[d]Samples will be collected in two different tubes (see Laboratory Manual for details).
[e]If a suspected Grade ≥2 IRR or Grade ≥2 CRS event is observed or reported, the following unscheduled samples should be collected:
Pharmacokinetic/immunogenicity sample(s): as close to the time of the event as possible, at 24 hours, and at 72 hours after the onset of the event.
Cytokine sample: within 4 hours after the onset of the event.
[f]Receptor occupancy samples will be collected for dose escalation cohorts treated at doses of 1 μg/kg or above.
[g]If the 72-hour sampling timepoint occurs on a weekend this sample may be collected at 96 hours.
[h]For all subsequent doses, predose and immediately after EOI (±15 min) blood samples should be collected for PK.

TABLE 19

Schedule of Activities for Biomarker, Pharmacokinetic and Immunogenicity Samples - Weekly Dosing Schedule Part 2

| Weekly Dosing Part 2 | | | Tumor biopsy[c] | T cell activation/ exhaustion TBNK[f] | Cytokine profile[d] | TCR seq | CyTOF/ T cell activation | ctDNA | CTC | PK[d] | Immuno-genicity[d] | RO |
|---|---|---|---|---|---|---|---|---|---|---|---|---|
| | | | | | | | Sample[a,b] | | | | | |
| Dose | Time | Window | Fresh tumor | Whole blood | Serum | Whole blood | Whole blood | Plasma | Whole blood | Serum | Serum | Whole Blood |
| | Screening | | X | | | | | | | | | |
| Dose 1 | Pre-dose | −4 hours | | X | X | X | X | X | X | X | X | X |
| | EOF | ±15 min | | | X | | | | | X | | |
| | 2 h | ±15 min | | | X | | | | | X | | X |
| | 6 h | ±30 min | | | X | | | | | X | | |
| | 24 h | ±2 hours | | X | | | X | | | X | | |
| | 72 h[g] | ±2 hours | | X | | | X | | | X | | X |
| Dose 2 | Pre-dose | −4 hours | | X | | X | X | | | X | | X |
| | EOF | ±15 min | | | X | | | | | X | | |
| | 2 h | ±15 min | | | X | | | | | X | | |
| | 24 h | ±2 hours | | | X | | | | | X | | |

TABLE 19-continued

Schedule of Activities for Biomarker, Pharmacokinetic and Immunogenicity Samples - Weekly Dosing Schedule Part 2

| Weekly Dosing Part 2 | | | Tumor biopsy[c] | T cell activation/ exhaustion TBNK[f] | Cytokine profile[d] | TCR seq | CyTOF/ T cell activation Sample[a,b] | ctDNA | CTC | PK[d] | Immuno- genicity[d] | RO |
|---|---|---|---|---|---|---|---|---|---|---|---|---|
| Dose | Time | Window | Fresh tumor | Whole blood | Serum | Whole blood | Whole blood | Plasma | Whole blood | Serum | Serum | Whole Blood |
| Dose 3 | Pre-dose | −4 hours | | X | X | | | | | X | X | |
|  | EOF | ±15 min | | | X | | | | | X | | |
| Dose 4 | Pre-dose | −4 hours | X[e] | X | | X | X | | | X | | |
|  | EOF | ±15 min | | | | | | | | X | | |
| Doses 5, 6, 7 | Pre-dose | −4 hours | | Dose 6 only | | Dose 6 only | Dose 6 only | | | X | Dose 5 only | |
|  | EOF | ±15 min | | | | | | | | X | | |
| Dose 8 | Pre-dose | −4 hours | | X | | X | X | | X | X | | |
|  | EOF | ±15 min | | | | | | | | X | | |
| Dose 9 | Pre-dose | −4 hours | | | | | | | | X | X | |
|  | EOF | ±15 min | | | | | | | | X | | |
| Dose 13 | Pre-dose | −4 hours | | | | | | X | | X | X | |
|  | EOF | ±15 min | | | | | | | | X | | |
| Dose 17[e] | Pre-dose | −4 hours | | | | | | | | X | X | |
|  | EOF | ±15 min | | | | | | | | X | | |
| EOT | | | | X | X | X | X | X | | X | X | |
| Post-treatment at 4 and 8 weeks after the last dose of the study drug. | | | | | | | | | | X | X | |

Abbreviations: CRS = cytokine release syndrome; CTC = circulating tumor cells; ctDNA = circulating tumor DNA; CyTOF = cytometry by time of flight; EOF = end of IV flush; EOT = end of treatment; IRR = infusion-related reaction; IV = intravenous; seq = sequencing; PK = pharmacokinetic; SET = study evaluation team; TCR = T cell receptor; TBNK = T cells, B cells, natural killer cells.
[a] All reasonable attempts should be made to collect samples within ±10% of the planned sampling time (ie, calculated from the end of IV flush) and the time of collection must be recorded.
[b] Samples will be shipped to laboratories designated by the sponsor; the analysis will be conducted by the sponsor. Repeat or unscheduled samples (ie, pharmacokinetic, pharmacodynamic, biomarkers) may be taken for safety reasons or for technical issues with the samples.
[c] Participants with accessible lesions enrolled in selected PK/PD cohorts in Part 1 and in Part 2 must agree to undergo the mandatory fresh tumor biopsies, unless collection of the biopsy presents a safety risk.
The fresh biopsy at screening maybe collected within 6 weeks (42 days) before the first dose of the study drug provided no active anticancer treatment was initiated during this time.
The post-treatment tumor biopsy sample collection time (ie, after the completion of the DLT evaluation period and between 4 to 8 weeks after the start of treatment) may be changed by the SET based on emerging data.
The samples will be sent to a central laboratory designated by the sponsor (see Laboratory Manual for details).
[d] If a suspected Grade ≥2 IRR or Grade ≥2 CRS event is observed or reported, the following unscheduled samples should be collected:
Pharmacokinetic/immunogenicity sample(s): as close to the time of the event as possible, at 24 hours, and at 72 hours after the onset of the event.
Cytokine sample: within 4 hours after the onset of the event.
[e] For all subsequent doses, predose and immediately after EOI (±15 min) blood samples should be collected for PK.
[f] Samples will be collected in two different tubes (see Laboratory Manual for details)
[g] If the 72-hour sampling timepoint occurs on a weekend this sample may be collected at 96 hours.

2. Introduction

The study drug is a humanized immunoglobulin G4 proline, alanine, alanine (IgG4 PAA) bispecific antibody targeting the CD3 receptor complex on T lymphocytes (T cells) and prostate-specific membrane antigen (PSMA) expressed on tumor cells and tumor associated neovasculature. the study drug is designed to promote the activation of T cells in close proximity with PSMA expressing target cells with subsequent tumor cell lysis by cytotoxic T cells (Buhler P, Wolf P, Gierschner D, et al. Cancer Immunol Immunother. 2008; 57(1):43-52).

A summary of the in vitro and in vivo pharmacology, safety pharmacology, and toxicology are presented within this section. The term "study drug" throughout this document refers to the study drug and the term "sponsor" refers to the entities listed in the Contact Information page(s), which will be provided as a separate document.

2.1. Study Rationale
2.1.1. Prostate Specific Membrane Antigen

PSMA is a transmembrane glycoprotein comprised of 750 amino acids and 3 protein domains; a small intracellular domain, a single-pass transmembrane domain, and a large extracellular domain. In prostate cancer, PSMA is expressed in both early and advanced disease settings and its expression is upregulated in response to anti-androgen therapies. Because of the unique expression profile of PSMA in prostate cancer, several therapeutic platforms that target PSMA are being explored for the treatment of prostate cancer including CD3-redirection approaches.

2.1.2. CD3 Redirection Approach

Recently, several approaches were developed to redirect T cells to tumor surface antigens. These include drugs that break tumor tolerance by T cell checkpoint blockade (McDermott D F, Atkins MB. Cancer Med. 2013; 2(5):662-673) and the bispecific T cell engager (BiTE) targeting CD19 (CD3×CD19), Blincyto® (blinatumomab) (Blincyto® [US FDA Product Label]. Thousand Oaks, USA: Amgen Inc.; December 2018).

The tumor microenvironment in PSMA positive tumors such as mCRPC may lack a sufficient immune presence, perhaps explaining the lack of efficacy of checkpoint inhibitors monotherapy in prostate cancer. T cell redirection is an important approach to enhance the immunogenicity of such tumors.

Two other CD3-redirecting approaches targeting PSMA with a mechanism of action similar to that intended for the study drug are currently being evaluated in clinical studies for the treatment of prostate cancer. The first, an Fc-competent bivalent bispecific CD3-PSMA molecule (Hernandez-Hoyos G, Sewell T, Bader R, et al. Mol Cancer Ther. 2016; 15(9):2155-2165). The second, a non-Fc-bearing CD3-PSMA bispecific T cell engager (BiTE) molecule (Klinger M, Benjamin J, Kischel R, Stienen S, Zugmaier G. Harnessing Immunol Rev. 2016; 270(1):193-208). Preliminary clinical data from this Phase 1 study indicate that doses up to 80 µg/day were tolerated and induced radiographic response in patients with CRPC. Another study of a tri-specific T cell activating construct (TriTAC) compound is also being evaluated in mCRPC (Lemon B, Aaron W, Austin R, et al. Cancer Research. 2018. Abstract 1773).

The study drug contains a mutated IgG4 Fc with significantly reduced binding to FcγRs but uninterrupted binding to FcRn to ensure extended half-life ($t_{1/2}$). Compared with the Fc-competent bivalent bispecific CD3-PSMA molecule and the TriTAC compound, the study drug more resembles an endogenous human IgG antibody, which could lead to reduced production of antidrug antibodies (ADAs), and ultimately an improved pharmacokinetic exposure and efficacy profile.

In vitro cytotoxicity assays were conducted to characterize the study drug-induced T cell activation, PSMA+ tumor cell killing, and release of cytokines. These assays were conducted using purified human T cells from 6 healthy human donors and C4-2B, a human prostate cancer cell line that expresses PSMA and demonstrates sensitivity to T cell mediated killing. Purified T cells from healthy donors, rather than cancer patients, were used to obtain a more conservative estimate of MABEL starting dose. Among the readouts that were evaluated (T cell activation, cytotoxicity, and cytokine release), T cell activation was shown to be the most sensitive readout (20). The MABEL concentration of 0.023 nM (3.45 ng/mL) was determined from the median effective concentration (EC) $EC_{20}$ value of T cell activation from the 6 normal donors.

Human pharmacokinetics of the study drug was predicted from the *cynomolgus* monkey pharmacokinetic data using allometric scaling. A clinical starting dose of 0.1 µg/kg was predicted to result in a C. of approximately 0.020 nM following the first dose, which is slightly below the MABEL concentration of 0.023 nM, as determined above.

The following considerations were also critical in determining the starting dose:
- A purified T cell system (instead of whole blood) was selected as the effector cell population because PSMA-expressing target cells are not reported to be present in the peripheral circulation in any significant amount.
- The C4-2B cell line is physiologically relevant with PSMA target expression similar with that observed in prostate cancer. Among the several prostate cancer cell lines evaluated (22-RV, C4-2/C4-2B, and LNCAP/LNCAP-AR), C4-2B is the one most sensitive to T cell-mediated target cell killing.
- The effector to target (E:T) ratios of 3:1, 5:1, 10:1, and 20:1 were evaluated in the in vitro cytotoxicity assay, and an E:T ratio of 3:1 was selected to provide a conservative estimate of the starting dose.
- Based on highest non-severely toxic dose (HNSTD) of 0.06 mg/kg from a pivotal GLP toxicology study, the human equivalent dose of HNSTD is 20 µg/kg using the body surface area conversion method, and the HNSTD-based maximum recommended starting dose is 3.3 µg/kg, which is 33-fold higher than the proposed MABEL-based starting dose.
- The lowest dose of the study drug tested in *cynomolgus* monkeys was 0.01 mg/kg. At this dose level, minimal levels of cytokine release, and minimal clinical signs and symptoms were observed.

TABLE 20

Summary of Exposure-response Analysis of T Cell-mediated Cytotoxicity, Cytokine Release, and T-cell Activation Assays with the study drug using C4-2B Cells

| | N (number of donors) | Median | Range |
|---|---|---|---|
| T cell Activation | | | |
| $EC_{20}$ (nM) | 6 | 0.023 | (0.011-0.027) |
| Cytotoxicity | | | |
| $EC_{20}$ (nM) | 6 | 0.039 | (0.011-0.074) |
| Cytokine release (based on most sensitive cytokine - IFN-γ) | | | |
| $EC_{20}$ (nM) | 6 | 0.032 | (0.018-0.065) |

Abbreviations: $EC_{20}$ = drug concentration required to produce 20% of the maximal effect.

Based on an overall assessment of the in vitro and in vivo data, and the MABEL-based FIH starting dose selection, 0.1 µg/kg weekly dose of the study drug should result in drug exposure that has minimal biological activity in participants treated in this study.

The $t_{1/2}$ of the study drug is predicted to be approximately 4.9 days in humans (at doses where non-linear clearance is saturated), which supported the decision to initiate the study with a weekly dosing schedule. An alternative dosing schedule of twice weekly treatment may be explored. Monoclonal antibodies can exhibit faster clearance at lower doses due to target-mediated drug disposition. Depending on the emerging pharmacokinetic, pharmacodynamic, and safety data, a decision to switch from the once weekly to a twice weekly schedule will be determined by the Study Evaluation Team (SET).

2.2. Background
2.2.1. Summary of Nonclinical Studies
PSMA Tumor and Normal Tissue Expression Profile In patient prostate adenocarcinoma tumor samples, PSMA protein was detected in 26 out of the 30 patient samples with the majority of samples displaying a heterogenous staining pattern for PSMA. To assess PSMA expression on human normal tissue, human tissue-microarrays were stained by immunohistochemistry for PSMA protein. Of all the different tissues tested, only prostate, brain, kidney, liver, mammary gland, small intestine, and salivary gland were positive for PSMA. Overall, PSMA expression in extra-prostatic normal tissues appears to be highly restricted, mostly cytoplasmic, and expressed at much lower levels than in prostatic tumoral tissue. These results are generally consistent with that reported in literature (Kinoshita Y, Kurastukuri K, Landas S, et al. World J Surg. 2006; 30:628-636; Spatz S, Tolkach Y, Jung K, et al. J Urol. 2018; 199(2):370-377)

Binding of the Study Drug to Prostate Tumor Cell Lines

The study drug specifically binds to endogenous PSMA-expressing prostate tumor cell lines in a concentration-dependent manner, as measured by flow cytometry for all PSMA-expressing tumor cell lines that were tested (C4-2B, LNCaPAR, 22RV1). In contrast, the study drug did not bind to PSMA-negative cell lines, PC-3 cells.

Study Drug-Mediated T Cell Activation

To measure the study drug-mediated T cell activation, PSMA-positive tumor cell lines were co-cultured with donor T cells from 6 normal donors for 48 hours in the presence of the study drug. The study drug caused a dose-dependent increase in CD25 expression, a marker of T cell activation in PSMA positive cell lines (C4-2B), but not in PSMA-negative cells (PC-3). Median EC ($EC_{20/50/90}$) values were determined across all donors from 3 separate experiments and were reported for the PSMA-positive cell line, C4-2B (EC$_{20}$: 0.02 nM, EC$_{50}$: 0.06 nM, EC$_{90}$: 0.40 nM). The 2 null control antibodies did not produce T cell activation in either C4-2B or PC-3 cell lines.

The Study Drug-Mediated T Cell Dependent Cytotoxicity of Prostate Tumor Cell Lines In Vitro To measure the ability of the study drug to induce cytotoxicity of PSMA-expressing tumor cells, donor T cells were co-cultured with tumor target cells at a 3:1 ratio for 72 hours and incubated with increasing amounts of the study drug or null antibodies lacking either CD3 or PSMA fragment antigen binding arms. the study drug caused dose-dependent cytotoxicity only in the PSMA-positive C4-2B cell line but not in the PSMA-negative PC-3 cell line. Median EC values were calculated for all 6 donors from 3 separate experiments and were reported for the C4-2B cell line (EC$_{20}$: 0.04 nM, EC$_{50}$: 0.08 nM, EC$_{90}$: 0.31 nM). The 2 null control antibodies did not produce T cell dependent cytotoxicity in either C4-2B or PC-3 cell lines.

Effects of the study drug In prostate tumor xenograft models In vivo Efficacy of the study drug was evaluated in LNCaP androgen receptor (AR) tumors, a human PSMA-positive prostate tumor xenograft model. Established tumors were implanted in non-obese diabetic (NOD) severe combined immunodeficiency (SCID) gamma (NSG) mice that were engrafted with human T cells. Statistically significant antitumor efficacy was observed at 2.5, 5.0, and 10 mg/kg dose levels of the study drug, with 51, 72, and 74% tumor growth inhibition (TGI), respectively achieved, as compared with vehicle-treated control mice ($p<0.0001$).

In Vivo Pharmacodynamic Effects of the Study Drug on CD8+ T Cell Tumor Infiltration To determine if the anti-tumor activity of the study drug was associated with immune cell infiltrate into tumors, LNCaP AR tumor-bearing mice were injected with human T cells, and serum and tumors were collected from phosphate-buffered saline control treated mice or from mice treated with 2.5, 5.0, and 10 mg/kg of the study drug. Time-dependent increases in tumor CD8+ T cell infiltration were observed by immunohistochemical staining at all dose levels of the study drug.

CONCLUSION

The in vitro and in vivo results indicate that the study drug specifically binds to PSMA-expressing tumor cells, induces T cell activation, and effectively redirects T cells to induce cytotoxicity of PSMA-expressing tumor cells.

2.2.2. Summary of Nonclinical Toxicology, Pharmacokinetics, and Safety Pharmacology 2.2.2.1. Toxicology Cynomolgus monkey was selected as the pharmacologically relevant toxicology species because the study drug has similar binding affinity to cynomolgus monkey PSMA and CD3 (compared with human) and has similar functional activity (cytotoxicity) on cynomolgus monkey and human PSMA expressing cells. Rodents were not pharmacologically relevant.

The potential toxicity of the study drug was characterized in 3 studies in cynomolgus monkeys, as summarized here.

Non-GLP Exploratory Toxicology Study

In a non-GLP exploratory study (n=1 to 6), tolerability of intravenous (IV) study drug in cynomolgus monkeys was assessed (0.03 to 3 mg/kg) utilizing several dose regimens in standard, and sexually mature (SM) males and in SM females. The most prominent dose-limiting toxicity (DLT) was cytokine release, which was predominantly a first-dose effect. Plasma cytokines appeared to directly correlate with mortality. Elevations in IFN-γ, IL-2, IL-6, IL-10 and TNF-α were observed. Sexually mature male cynomolgus monkeys were noted to be most sensitive to the effects of the study drug and had higher cytokine release than standard males and sexually mature females. Significant loss of exposure was observed after Days 10 to 15 in most of the monkeys (due to anti-drug antibody [ADA]) and hence, the duration of subsequent studies was limited to 2 weeks. At the maximum tolerated dose (MTD) of 0.06 mg/kg, both the once every 3 days (Q3D; total 8 doses) and the once a week (Q1W; total of 4 doses) dose frequencies were well-tolerated and cytokine release was mostly observed (and highest) at the first dose.

At non-tolerated doses, monkeys were either moribund or euthanized between Day 1(≥6 hours) and Day 2 of the first dose except one female (0.6 mg/kg) who was euthanized on Day 8 (post the first dose). Mortalities in this study generally correlated with plasma cytokine levels. The cause of death in all early decedents could not be determined histologically and was presumed to be due to severe cytokine release. The microscopic findings on the scheduled day of necropsy (Day 30) included mononuclear infiltrates in liver, kidney, gall-bladder, minimal to mild tubular degeneration/regeneration, mineralization (0.06 mg/kg, Q3D; 8 doses), mononuclear interstitial infiltrates around the tubular findings or large vessels, and mild bone marrow hypercellularity. Additionally, minimal multifocal tubular mineralization was noted in the kidney of the single female that received the 0.3 mg/kg dose. No histological correlates related to mortality were identified in the early decedents. The MTD in SM males (most sensitive) was 0.06 mg/kg (Q3D or Q1W).

GLP Toxicology Study

In the pivotal GLP study in SM cynomolgus monkeys, the study drug was administered by IV bolus injections Q1W (3 total doses) or Q3D (6 total doses) for 2 weeks, followed by a 6-week recovery period. The Q3D doses administered to males were 0, 0.03 or 0.06 mg/kg; females received 0, 0.06, or 0.2 mg/kg. The Q1W doses for males were 0.06 mg/kg and for females were 0.2 mg/kg. Clinical signs (emesis, hunched posture) were primarily associated with administration of the first dose and generally not observed during the latter dosing phase (in line with cytokine release). Generally, dose-related increases in cytokine plasma concentrations were observed in both male and female monkeys at dose levels ≥0.03 mg/kg.

One of the 5 females (0.2 mg/kg Q1W) was euthanized on Day 3 due to declining clinical condition. The cause of death in this monkey could not be determined and was likely due to severe cytokine release. In monkeys that successfully completed dosing, there were no study drug-related changes in body weights, food consumption, physical examination measurements, and ocular effects, and no abnormalities in electrocardiograms (ECGs) or changes in blood pressure, heart rate, respiratory rate, body temperature, urinalysis, gross necropsy findings, or absolute or relative organ weights. The study drug-related microscopic findings (from scheduled necropsy on Day 16/17) at ≥0.03 mg/kg were limited to lymphocytic infiltration noted in the perivascular regions of the kidney (minimal to mild), liver (minimal to moderate), and gall bladder (mild). All microscopic findings resolved after a six-week recovery period on Day 57, except mild perivascular infiltrate, which remained in the kidney of one female that received 0.2 mg/kg on 6 occasions. The HNSTD in the pivotal study was 0.06 mg/kg/dose.

Non-GLP Investigative Study (Effects of Using Low Dose Priming or Prophylactic Tocilizumab to Manage Cytokine Release)

A non-GLP study was conducted to determine if the dose-limiting cytokine release seen in previous studies could be mitigated. Two approaches were tested which included intra-animal dose escalation following a priming dose or prophylactic treatment with tocilizumab.

In the low dose priming part of the study phase, the study drug was administered as a slow dose escalation (0.01→0.02→0.04→0.12→0.6 mg/kg) and a rapid intra-animal escalation (0.01→0.03→0.1→0.4→1.5 mg/kg), via IV slow bolus injection on Days 1, 4, 7, 10, and 13. Both escalation cohorts successfully completed dosing without mortality and with marked improvement in clinical signs, and there were no study drug-related effects on apparent food consumption or changes in physical examination measurements. Improvement in clinical signs (sporadic slight to moderate emesis on Day 1, liquid feces, transient and minimal changes in body temperature) were likely related to low levels of cytokine release at the priming dose of 0.01 mg/kg and markedly reduced cytokine release at subsequent escalated doses. At scheduled necropsy on Day 19, mixed cell infiltration into multiple organs and degeneration/regeneration of tubules (minimal) and acinar cells (minimal to mild) in the kidney and prostate, respectively, was observed in both dose escalating groups. Additional changes considered consistent with a systemic inflammatory response included hematopoietic aggregates in the heart (in the rapid escalation group) and mononuclear cell infiltration with fibrin accumulation within the femorotibial synovial joint in both dose escalating dose groups. There were no findings that were considered adverse.

In the tocilizumab prophylactic treatment study phase, the study drug was administered via IV slow bolus injection at 0, 0.1, 0.3, or 0.9 mg/kg on Days 1 and 8 following a single dose of tocilizumab given the day prior (~8 to 24 hours prior to administration of the study drug). Tocilizumab appeared to have some protective effect (at 0.1 mg/kg) or delayed mortality (at 0.3 mg/kg), when compared with observations in previous studies without tocilizumab pretreatment. Tocilizumab did not improve tolerability in a monkey that received 0.9 mg/kg and the monkey was euthanized approximately 7 hours after the Day 1 dose. Prophylactic tocilizumab did not appear to have a discernible effect on the study drug-mediated cytokine release (or related clinical signs) and the microscopic and clinical pathology findings were similar to that noted in studies without tocilizumab pretreatment.

Summary of Clinical Pathology Changes Noted Across Studies

A cross-study analysis in male SM monkeys was conducted to compare the clinical pathology changes associated with administration of the study drug in the non-GLP exploratory study, the 2-week pivotal GLP toxicity study, and the non-GLP low-dose priming study. Changes in clinical pathology parameters were generally similar across all 3 studies and were representative of a systemic inflammatory response. These findings did not correlate with the presence or severity of clinical signs for individual monkeys including monkeys that were euthanized early due to declining condition. Clinical pathology changes themselves were generally not sensitive or specific biomarkers for the study drug-related clinical signs or overall tolerability. Changes observed included a decrease in leukocyte counts (neutrophil, lymphocyte, monocyte and eosinophil counts), increase in neutrophil, eosinophil, and basophil counts in some studies, decreased red blood cell mass, decrease in platelet count, increase in acute phase reactants, increase in alkaline phosphatase, increase in renal parameters such as urea nitrogen and creatinine, decrease in serum calcium, increase in coagulation times, increase in enzyme activities and increased bilirubin. There was no discernible dose-dependent relationship noted with the above findings.

2.2.2.1.1. Tissue Cross-Reactivity

A GLP cross-reactivity study was conducted in cryosections of normal human tissues with the study drug and its anti-PSMA parental (bivalent) antibody (positive control). No unanticipated tissue cross-reactivity of the study drug was observed. Membrane staining of epithelial cells and staining of extracellular material in the prostate with both the study drug and the anti-PSMA parental antibody was anticipated due to PSMA expression in these tissues. Staining of mononuclear cells with the study drug only was expected based on the expression of CD3ε on T cells.

2.2.2.1.2. Assays in Human Serum or Whole Blood

The study drug did not cause hemolysis in whole human blood and was compatible with human serum at in vitro concentrations of 0.010 and 10 mg/mL 2.2.2.1.3. Cytokine Release In an in vitro assay, the study drug induced statistically significant and concentration-dependent cytokine release in 6 of 10 cytokines measured (IL-1β, IL-2, IL-8, IL-10, IFN-γ, and TNF-α) in whole blood from healthy donors.

2.2.2.2. Safety Pharmacology

There were no study drug-related changes in body temperature, blood pressure, heart rate, respiration rate, or neural behavioral clinical observations. No study drug-related abnormalities in cardiac rhythm or ECG waveform morphology were found at any dose level based on comparison of predose and postdose ECGs. Hypotension and tachycardia have been observed in monkeys following treatment with other CD3 redirector antibodies, possibly related to cytokine release.

2.2.2.3. Nonclinical Pharmacokinetics and Immunogenicity

The pharmacokinetics/toxicokinetics (PK/TK) of the study drug was characterized following a single IV administration in *cynomolgus* monkeys at intended doses of 0.3, 0.6, and 3 mg/kg as part of the non-GLP exploratory toxicology study in standard age (juvenile—2.5 to 4 years) or SM male monkeys. Based on limited data from surviving monkeys, the study drug exposure increased with dose in an approximately dose-proportional manner over the tested dose range. Similar clearance (CL), volume of distribution (Vss), and $t_{1/2}$ were estimated across the dose groups. The study drug exhibited relatively high CL (18.69 to 26.17 mL/day/kg) and shorter $t_{1/2}$ (2.48 to 3.12 days) in comparison to typical IgG-based therapeutic monoclonal antibodies.

The PK/TK of the study drug following multiple IV administrations were characterized in the GLP toxicology study in SM *cynomolgus* monkeys. The monkeys received IV bolus injections of the study drug either Q3D (6 doses) or Q1W (3 doses) for 2 weeks, followed by a 6-week recovery period. Due to anticipated gender-related differences in tolerability, the male monkeys received Q3D doses at 0.03 and 0.06 mg/kg, respectively, and Q1W doses at 0.06 mg/kg; the female monkeys received Q3D doses at 0.06 and 0.2 mg/kg, respectively, and Q1W doses at 0.2 mg/kg. The mean $C_{max}$ and AUC increased in an approximately dose-proportional manner over the tested dose range. Following Q3D dosing, mean drug accumulation ratios ranged from 1.30 to 1.57 in the 0.03 and 0.06 mg/kg dose groups, and 0.95 for the 0.2 mg/kg dose group. There was no systemic accumulation of the study drug following Q1W dosing.

Compared with the PK/TK after the first dose on Day 1, decreases in drug exposure following either the fifth Q3D dose or the second Q1W dose were observed in multiple monkeys, which may be related to the development of ADA. There was no apparent PK/TK difference between male and female monkeys.

The PK/TK of the study drug following multiple (ie, Q3D or Q1W) IV administrations were also examined as part of the non-GLP exploratory toxicology study and the non-GLP investigative toxicity study in *cynomolgus* monkeys and the results were similar. In the non-GLP investigative toxicity study in SM *cynomolgus* monkeys, the study drug was administered as a slow dose escalation (0.01→0.02→0.04→0.12→0.6 mg/kg) and a rapid escalation (0.01→0.03→0.1→0.4→1.5 mg/kg) via IV injections on Days 1, 4, 7, 10, and 13, respectively, the study drug exposure increased with dose in an approximately dose-proportional manner. The mean C. and AUC following the highest dose of 1.5 mg/kg were >0-fold higher than that following the 0.06 mg/kg Q3D IV doses in the GLP toxicology study.

The immunogenicity of the study drug in *cynomolgus* monkeys was assessed in the non-GLP exploratory toxicity study and the GLP toxicity study. Forty out of the 56 monkeys treated with IV doses of the study drug tested ADA-positive. Among the other 16 monkeys, 13 did not have appropriate samples for immunogenicity determination (ie, no sample on or after Day 13) and therefore, their ADA status was unevaluable; the remaining 3 monkeys tested ADA-negative. Overall, the incidence of ADA for the study drug was high. Immunogenicity in animals is not expected to be predictive of the human immunogenic response.

2.3. Benefit/Risk Assessment

This is the first clinical study of the study drug. The potential risks and mitigation strategies are based on safety data available from nonclinical studies, known mechanism of action (ie, T cell activation and tumor cell lysis), and route of administration. Although expression of PSMA in normal tissues is highest in prostate tissue, relatively low-levels of membrane expression is also detected in the brain, kidney, liver, mammary gland, small intestines and salivary gland (see Section 2.2.1). Therefore, there is the potential for study drug-induced toxicities in these organs. Safety monitoring will include frequent laboratory evaluations (blood chemistry and hematology) and physical examinations including neurologic assessments, to monitor for potential toxicities in these organs.

Potential risks are noted below. Precautions relevant to immunological effects and PSMA expression pattern are discussed in Section 6.1.2. Dose modification guidance is provided in Section 6.6.

Immunological effects: Guidance for pretreatment medications to manage these potential safety risks is provided in Section 6.1.2.

Infusion-related reactions (IRRs)(Section 6.1.2.1)

Immune-related adverse events (Section 6.1.2.2)

Cytokine release syndrome (CRS)(Section 6.1.2.3)

Potential toxicities due to PSMA expression pattern:

Tumor lysis syndrome—monitoring of adverse events and chemistry parameters after the first study drug administration Renal toxicity—monitoring of adverse events and chemistry parameters Liver toxicity—monitoring of adverse events and chemistry parameters Neurotoxicity (Section 6.1.2.4)

Parotid/salivary gland toxicity—monitoring of adverse events

Gastrointestinal toxicity—monitoring for adverse events

Clinical laboratory abnormalities: Consistent with the expected pharmacologic functions from CD3 engagement, the most noteworthy changes of laboratory parameters observed in toxicology studies with *cynomolgus* monkeys consisted of changes in leukocytes (primarily decreased lymphocytes, monocytes, and eosinophils sometimes followed by increases in these and other leukocytes), increases or decreases in neutrophils, decreased platelets, decreased red blood cell mass, an acute phase response, increased renal parameters, prolonged coagulation times, and increased hepatic enzyme activities and bilirubin.

It is unknown if there is clinical benefit associated with the study drug treatment. The study drug has the potential to lead to effective killing of target cells that express PSMA such as, tumor or tumor associated neovasculature cells, and possibly result in an increase in overall survival for patients with advanced disease and limited treatment options.

3. Objectives and Endpoints

TABLE 21

Objectives and Endpoints.

| Objectives | Endpoints |
|---|---|
| *Primary* | |
| Part 1 (Dose Escalation) Determine the recommended Phase 2 dose (RP2D) regimen and the maximum tolerated dose | Incidence and severity of adverse events, including dose-limiting toxicity |
| Part 2 (Expansion) Determine the safety of the study drug at the RP2D regimen | Incidence and severity of all adverse events |
| *Secondary* | |
| To assess the pharmacokinetics of the study drug following multiple IV doses. | Serum concentration-time profiles and pharmacokinetic parameters for the study drug including but not limited to $C_{max}$, $T_{max}$, $AUC_{(t1-t2)}$, $AUC_{tau}$, $C_{min}$, and accumulation ratio (RA) |
| To assess the pharmacodynamics of the study drug following multiple IV doses. | Pharmacodynamic markers including but not limited to systemic cytokine concentrations, markers of T cell |

TABLE 21-continued

Objectives and Endpoints.

| Objectives | Endpoints |
|---|---|
|  | activation, RO, and serum prostate specific antigen (PSA) |
| To assess the immunogenicity of the study drug. | Presence of the study drug antibodies. |
|  | Exploratory |
|  | To evaluate the preliminary clinical activity of the study drug in participants with advanced solid tumors: Objective response rate and duration of response. Response for solid tumors will be assessed according to response criteria of Prostate Cancer Working Group 3 (PCWG3) for prostate cancer or Response Evaluation Criteria in Solid Tumors (RECIST) v1.1 To explore the relationships between pharmacokinetics, pharmacodynamics, adverse event profile, and clinical activity of the study drug. To investigate biomarkers predictive of clinical response or resistance to the study drug. |

Hypothesis

No formal statistical hypothesis testing will be conducted in this study. The study will evaluate the following:

Dose Escalation (Part 1): the RP2D of the study drug can be identified such that <33% of participant experiences a DLT.

Dose Expansion (Part 2): the study drug is safe and shows preliminary clinical activity at the RP2D.

3.1.1. The Study Drug

The study drug is a bispecific antibody developed to evaluate the therapeutic potential of targeting PSMA for CD3-mediated T cell redirection. The study drug is a human IgG4 antibody engineered. The bispecific antibody was generated by controlled fragment antigen binding arm exchange from 2 parental antibodies: PSMB127 and CD3B219. PSMB127 is an anti-PSMA antibody originated from a whole cell panning of a phage library on a PSMA over-expressing cell line. CD3B219 is an anti-CD3ε antibody that originated from a public domain antibody, SP34, which was further humanized, and affinity matured. It is hypothesized that the study drug will induce enhanced T cell-mediated cytotoxicity through recruitment of CD3-expressing T cells to the PSMA-expressing cells. This will lead to the activation of T cells and induce subsequent PSMA-positive cell lysis mediated by cytotoxic T cells.

4. Study Design 4.1. Overall Design

This is a FIH, open-label, multicenter, Phase 1 study to evaluate the safety, pharmacokinetics, pharmacodynamics, and preliminary clinical activity of the study drug monotherapy in participants with advanced cancers. Approximately 70 participants will be treated in this 2-part study. Additional participants may be enrolled if priming dose schedule(s) are explored. Once a participant is determined to be eligible (ie, inclusion/exclusion criteria) for the study and has provided informed consent for study participation, the study drug will be administered as an IV infusion. The overall safety of the study treatment will be continually assessed throughout the study by the SET (see Section 4.1.4). Preliminary clinical activity will be evaluated according to the assessments outlined in Section 8.1. The pharmacodynamics of the study drug will be characterized by pretreatment and on-treatment biopsies in selected cohorts, as determined by the sponsor.

Part 1 (Dose Escalation)

Part 1 of the study is designed to determine the MTD of the study drug in participants with metastatic castration-resistant prostate cancer (mCRPC) and to select the RP2D(s) and regimen(s). Dose Escalation will begin at the MABEL-based starting dose and proceed as shown in Table 18. Dose escalation will be supported using an adaptive design dose escalation strategy guided by the modified continual reassessment method (mCRM) based on a statistical model, Bayesian Logistic Regression Model (BLRM), with Escalation with Overdose Control (EWOC) principle. Dose escalation will be carried out in 2 phases: accelerated and standard titration phases.

Study Evaluation Team decisions will be based on the review of all available data including, but not limited to, pharmacokinetic, pharmacodynamic, safety, and efficacy. Dose escalation will proceed according to the dose escalation strategy outline in Section 4.1.1.

In Part 1a, single participant cohorts will be enrolled during accelerated dose escalation at doses assigned by the SET. Up to 12 additional participants may be treated in the pharmacokinetic/pharmacodynamic (PK/PD) cohorts at doses determined to be safe by the SET to better understand the safety, pharmacokinetics, pharmacodynamics, and preliminary clinical activity. Once a Grade ≥2 non-hematologic toxicity or Grade ≥3 hematologic toxicity of anemia, neutropenia or thrombocytopenia occurs, the study will transition from an accelerated titration phase to standard titration phase and begin enrolling 3 to 6 participants per cohort. Standard titration may occur without priming (Part 1b), or if the toxicity is Grade ≥2 CRS, the standard titration may occur with a priming dose (Part 1c). During standard dose escalation, additional participants may be enrolled in PK/PD cohorts to obtain additional data.

Part 2 (Dose Expansion)

Once the RP2D(s) is determined, participants with mCRPC (n=20) will be treated to confirm the safety, pharmacokinetics, pharmacodynamics, and preliminary clinical activity of the study drug at the RP2D(s).

Overall Treatment Plan

The treatment and priming dose(s) schedules are described below and in Table. The initiation of a priming dose(s) may be considered to mitigate toxicities.

Treatment Dose Schedule: Based on the projected $t_{1/2}$ of 4.9 days at the saturating dose scaled from a *cynomolgus* monkey model, the study will be initiated with once a week treatment doses. The starting dose will be 0.1 µg/kg administered via IV infusion once a week. An alternative schedule of twice a week treatment doses may be explored. The decision to switch from once weekly to twice weekly treatment will be based on emerging data and after approval by the SET. Dose escalation decisions as well as subsequent dose levels will be determined based on a statistical model using all available safety, pharmacokinetic, pharmacodynamic, and clinical activity data to identify safe and tolerable RP2D(s). Enrollment to Part 2 will begin after the RP2D(s) for the study drug has been determined in Part 1.

Prior to the first dose of study drug, corticosteroid premedication will be administered to minimize the risk associated with IRR (see Table). Corticosteroid premedication may be reduced or omitted for subsequent doses. For participants who experience a Grade 2 or higher IRR, pre-infusion corticosteroid will be required for at least 1 subsequent dose administered to that participant.

Priming Dose Schedule(s): Priming dose strategies have been effectively utilized for bispecific T cell engager antibodies such as blinatumomab due to the potential for these antibodies to cause acute cytokine-mediated toxicities associated with first dose administration. In this study, a priming dose schedule will be initiated after the first incidence of Grade ≥2 CRS. One or more initial lower doses may be administered prior to a subsequent higher treatment dose to mitigate the acute toxicities that may be associated with T cell activation and cytokine release. See Section 4.1.1 for selection of the priming dose(s).

Required Hospitalization and Discharge Criteria

Part 1: Participants will be hospitalized for at least 48 hours after the IV flush for the first 2 treatment doses and any associated priming dose(s) of the study drug. Hospitalization will be optional for subsequent doses unless certain safety criteria are met: prior Grade ≥2 neurologic toxicity, intrapatient dose escalation for priming schedules, or prior Grade ≥2 CRS that does not resolve to Grade ≤1 within 72 hours. If any one of these toxicities occurs during administration of the study drug, the participant will be hospitalized for at least 48 hours after the next study drug administration (after IV flush) to monitor for signs and symptoms related to CRS or neurologic toxicity.

Part 2: Based on the experiences from Part 1, hospitalization may not be required. However, if the participant has prior Grade ≥2 neurologic toxicity or prior Grade ≥2 CRS that does not resolve to Grade ≤1 within 72 hours, hospitalization will be required for at least 48 hours after the next study drug administration.

Discharge Criteria

The following criteria must be met before the participant is discharged from the hospital: vital signs and oxygen saturation within normal range, including absence of fever, defined as a temperature ≤100.4° F. (38° C.) for at least 24 hours, and absence of any significant Grade ≥2 adverse event that is not attributed to the underlying disease.

Treatment Discontinuation/Follow-up

Participants will receive the study drug until radiographic disease progression, unequivocal clinical progression, unacceptable toxicity, or any other treatment discontinuation criteria are met (see Section 7). However, treatment beyond disease progression may be considered (see Section 8.1.2). For participants who discontinue study treatment for reasons other than disease progression (eg, adverse event), disease assessments will continue to be performed per local standard of care until disease progression or a new anticancer therapy is initiated (or another study withdrawal criterion is met). After treatment discontinuation, participants will have an end-of-treatment (EOT) visit within 30 (+7) days after the last dose of study drug and continue in the study for follow-up as outlined in Section 8.

Data Cutoff and End of Study

The sponsor will establish a clinical data cutoff date for clinical study report (CSR) analysis reporting, which may occur before the end of study. The data cutoff will be communicated to the sites. Participants who continue to receive the study drug or who are in follow-up after the data cutoff will continue to be monitored according to Table 7 until the end of study. These data will be reported to the appropriate health authorities in a final CSR. The final data from the study site will be sent to the sponsor (or designee) after completion of the final participant visit at that study site, in the timeframe specified in the Clinical Trial Agreement. The end of study (study completion) is defined in Section 4.4.

4.1.1. Dose Escalation Rules

Part 1: Dose escalation decisions will be made by the SET based on mCRM utilizing all the DLT data, as well as safety, pharmacodynamic, pharmacokinetic, and other biomarker(s) data of all prior dose levels. Preliminary clinical activity, if available, will also be reviewed by the SET at each dose escalation step.

In Part 1, the mCRM will be carried out in 2 phases: (1) accelerated titration phase and (2) standard titration phase (with and without priming). Dose escalation will begin with treatment doses administered weekly; twice weekly dosing may be initiated based on emerging data. A priming schedule may be explored as described later in this section. The mCRM will be carried out as follows:

Part 1a—Accelerated Titration

The following rules apply during accelerated titration using mCRM.

Dose escalation will begin with single (at least 1) participant cohorts.

If more than 1 participant is treated at a dose level, the first participant treated at that given dose level must be observed for 48 hours prior to treating subsequent participants.

Evaluation of at least 1 participant who has completed the DLT evaluation period (see Section 4.1.3) is required prior to the SET determination that the dose is safe and prior to enrollment in the next cohort.

Dose escalation will proceed as guided by BLRM with EWOC principle (ie, providing a highest recommended dose) except that the next dose level may not exceed a 3.5-fold increment from the previous dose.

The study may switch from accelerated titration to standard titration if one of the following occurs during the DLT evaluation period:

A Grade ≥2 non-hematologic toxicity or Grade ≥3 hematologic toxicity of anemia, neutropenia, or thrombocytopenia: Part 1b—standard titration without priming.

For clinical laboratory abnormalities, the timeframes in Table will be used to assess DLTs and these events also will trigger the switch to Part 1b.

One or more Grade ≥2 CRS events: Part 1c—standard titration with priming.

Up to 12 additional participants may be enrolled in a PK/PD cohort at doses determined to be safe by the SET to obtain additional pharmacokinetic, pharmacodynamic, or biomarker data. Once the criteria for stopping the accelerated dose titration have been met, dose escalation will transition to standard titration as described below.

Part 1b—Standard Titration (without Priming)

The following rules apply during standard titration using mCRM.

Evaluation of a dose level with at least 3 participants completing the DLT evaluation period (Section 4.1.1) is required before determining the dose for the next cohort.

The first participant treated at a given dose level must be observed for 48 hours prior to treating subsequent participants.

Primary Model Determined by DLT (see Section 9.1.1)
If no participant in a cohort experiences a DLT, dose escalation of the treatment dose may proceed as guided by BLRM with EWOC principle (ie, providing a highest recommended dose) except that the next dose level may not exceed a 3.5-fold increment from the previous dose.
If one participant in a cohort experiences DLT during the DLT period, then the SET (as guided by BLRM with EWOC principle) may either,
  Agree to enroll additional participants before determining the next dose level or
  Reassess the cohort based on all available data and the updated probability of DLT, and determine the next dose cohort guided by BLRM with EWOC principle (ie, providing a highest recommended dose)
If 2 participants in a specific dose cohort experience a DLT, further enrollment to that dose cohort will stop, and the SET will re-evaluate the cohort based on all available data and the updated probability of DLT. Based on the re-evaluation of the dose cohort, additional participants may be enrolled into the current or a lower dose cohort only if that dose level still meets the EWOC principle and is agreed to by the SET.
Up to 12 additional participants may be enrolled in a PK/PD cohort at doses determined to be safe by the SET to obtain additional pharmacokinetic, pharmacodynamic, or biomarker data.
The study may initiate priming (Part 1c) if a Grade ≥2 CRS event is observed.

Part 1 c—Standard Titration (with Priming)

A priming dose will be administered on Day 1 followed by the treatment dose administered on Day 8. However, more than one priming dose may be administered based on review of available data and after review by the SET.
  The priming dose(s) will be determined as follows:
  If the first CRS event is Grade 2 or 3, the dose level at which the first event occurred will be expanded to at least 6 participants.
    If no additional Grade ≥2 CRS is observed, this dose level will be considered the priming dose.
    If additional participants have Grade ≥2 CRS, a previous dose level at which no CRS was observed will be expanded to at least 6 participants.
    If no more than 1 of 6 participants experience a Grade 2 or 3 CRS, this dose level will be considered the Day 1 priming dose.
  If the first CRS event was Grade ≥4 CRS, a previous dose level at which no CRS was observed will be expanded to at least 6 participants.
    If no more than 1 of 6 participants experience a Grade 2 or 3 CRS at this lower dose level, this dose level will be considered the Day 1 priming dose.

Initial Priming Cohort
  In the first priming cohort, the treatment dose will be determined as follows:
  The first treatment dose will be determined by the mCRM.
    If the first CRS event is Grade >2, the treatment dose may be reduced below the dose at which the Grade >2 CRS was observed.
  Evaluation of a priming schedule with at least 3 participants completing the DLT evaluation period (Section 4.1.3) is required before determining the dose for the next cohort.
  The first participant treated at a given dose level must be observed for 48 hours prior to treating subsequent participants.

Primary model determined by DLT
If no participant in a cohort experiences a DLT, dose escalation may proceed as guided by BLRM with EWOC principle (ie, providing a highest recommended dose) except that the next dose level may not exceed a 100% increment from the previous dose.
If one participant in a cohort experiences DLT during the DLT period, then the SET (as guided by BLRM with EWOC principle) may either;
  Agree to enroll additional participants before determining the next dose level
    or
  Reassess the cohort based on all available data and the updated probability of DLT, and determine the next dose cohort guided by BLRM with EWOC principle (ie, providing a highest recommended dose)
If 2 participants in a specific dose cohort experience a DLT, further enrollment to that dose cohort will stop, and the SET will re-evaluate the cohort based on all available data and the updated probability of DLT. Based on the re-evaluation of the dose cohort, additional participants may be enrolled into the current or a lower dose cohort only if that dose level still meets the EWOC principle (see Section 9.1.1) and is agreed to by the SET.
Up to 12 additional participants may be enrolled in a PK/PD cohort at doses determined to be safe by the SET to obtain additional pharmacokinetic, pharmacodynamic, or biomarker data.
Multiple dose level and dose schedule cohorts may be enrolled in parallel provided all the criteria above have been met and that each of the new dose cohort(s)/schedules(s) is recommended by the SET and supported by the statistical model, with EWOC principle.

Provisional Dosing Table

A sample provisional dosing table is provided in 22. Dose levels will be discussed at SET meetings (see Section 4.1.4) and are subject to change based on emerging data. Intermediate dose-level increments are possible to ensure the safety of study participants. The actual ascending dose levels will be guided by mCRM based on BLRM. A maximum dose level has not been identified for this study.

TABLE 22

Provisional Dosing Table

| Dose Level | Dose (µg/kg) | Increment |
|---|---|---|
| Dose Level 1 | 0.1 µg/kg | Starting Dose (MABEL) |
| Dose Level 2 | 0.3 µg/kg | 300% |
| Dose Level 3 | 1 µg/kg | 300% |
| Dose Level 4 | 3 µg/kg | 300% |
| Dose Level 5 | 10 µg/kg | 300% |
| Dose Level 6 | 20 µg/kg | 100% |
| Dose Level 7 | 40 µg/kg | 100% |
| Dose Level 8 | 80 µg/kg | 100% |
| Dose Level 9 | 120 µg/kg | 50% |

Note:
this table shows the treatment dose level (not priming doses).

4.1.2. Determination of the RP2D

The RP2D(s) will be determined after review of all available pharmacokinetic, pharmacodynamic, safety, and efficacy data from at least 6 participants treated at the RP2D and at least 12 participants with pharmacokinetic data across all cohorts and will take into consideration the recommended dose by BLRM. One or more RP2D(s) may be selected.

4.1.3. Definition of Dose-Limiting Toxicity

The DLT evaluation period is defined as the first 21 days of treatment. If priming dose(s) are explored, then the priming period will be included in the DLT evaluation period. Participants who do not complete the DLT period for reasons other than DLT may be replaced. If the participant received less than 75% of each assigned dose during this time period for reasons other than toxicities (eg, disease progression, missed appointments, non-compliance, participant withdrawal), the participant may be replaced with a new participant at the discretion of the SET. All available safety data from non-evaluable participants will be taken into consideration by the SET. Criteria for DLT are outlined in Table below. Dose-limiting toxicities leading to treatment discontinuation are described in Section 7. These events are evaluated according to National Cancer Institute Common Terminology Criteria for Adverse Events (NCI CTCAE Version 5.0).

TABLE 23

Dose-Limiting Toxicity Criteria[a]

| Non-hematological Toxicity | |
|---|---|
| Non-hematological toxicity except chemistry abnormalities listed below | Grade 3<br>Grade 4<br>Grade 5 |
| Chemistry abnormalities other than AST, ALT, GGT, total bilirubin, lipase or amylase[d] | Grade 3 for >7 days without clinical sequelae or >3 days if associated with clinical sequelae despite best supportive care[b]<br>Grade 4 |
| Specific chemistry abnormalities | AST, ALT or total bilirubin: Grade 3 that has not returned to Grade ≤1 or baseline within 5 days, or meets criteria for Hy's law[c]<br>Lipase or amylase: Grade ≥3 associated with clinical or radiological evidence of pancreatitis |

Exceptions

Tumor lysis syndrome and related chemistry abnormalities (potassium, uric acid, calcium, phosphate): Grade ≤4 that recovers to Grade <2 within 72 hours
Grade 3 asthenia, fever, or constipation lasting <7 days
Grade 3 nausea, vomiting, or diarrhea <7 days with best supportive care
Isolated Grade 3 or 4 GGT elevation (without concurrently either AST or ALT that meets Grade 3 or total bilirubin that meets Grade 2) associated with liver metastases
Grade 3 IRR or Grade 3 CRS that returns to Grade ≤1 within <72 hours

| Hematological Toxicity | |
|---|---|
| Neutrophil count decreased | Febrile neutropenia: Grade ≥3<br>Neutropenia: Grade 4 for ≥7 days |
| Platelet count decreased | Grade 3 thrombocytopenia with bleeding or any Grade 4 |
| Any hematological toxicity | Grade 5 |

Abbreviations: ALP = alkaline phosphatase; ALT = alanine aminotransferase; AST = aspartate aminotransferase; CRS = cytokine release syndrome; DLT = dose-limiting toxicity; GGT = gamma-glutamyl transferase; IRR = infusion-related reaction; ULN = upper limit of normal.
Unless toxicity is unequivocally due to the underlying malignancy or an extraneous cause.
Best supportive care (including electrolyte and hormone supplementation where clinically applicable) according to institutional standards.
Hy's Law criteria defined as, ALT or AST value ≥3 x ULN, total bilirubin ≥2 x ULN, and ALP ≤2 x ULN; with no alternative etiology.
Chemistry abnormalities Grade ≥3 occurring during the DLT period need to be repeated within 72 hours to confirm grade or resolution.

4.1.4. Study Evaluation Team

Participant safety and study conduct will be monitored throughout the study by the SET established by the sponsor. This committee will monitor all treatment-emergent data (eg, pharmacokinetic, pharmacodynamic, safety) on an ongoing basis throughout the study to ensure the continued safety of participants enrolled in this study. Cumulative data will be monitored for late onset toxicities.

The SET will be chaired by the sponsor's Study Responsible Physician. Membership will include principal investigators, a sponsor clinical scientist, safety physician (sponsor's Safety Management Team chair), statistician, clinical pharmacologist, along with additional sponsor staff, as appropriate. The team will meet at regular frequency throughout study conduct and may be conducted at any time during the study at the request of either the sponsor or investigators to assess emerging safety signals. Documentation of meeting outcomes will be maintained by the sponsor. Decisions will be communicated to investigators and decisions with the potential to affect participant safety (eg, unfavorable change in risk/benefit assessment) will also be promptly communicated to regulatory authorities, as required.

Dose escalation decisions and changes to the treatment and procedure schedule (s) will be made by the SET. The schedule of dose escalation meetings will depend on the frequency of DLTs and if/when the MTD or maximum administered dose (MAD) is determined or when an RP2D (s) is determined.

The SET may also decide on modifications in study conduct or stop further enrollment into one or more cohorts if treatment-emergent toxicity is determined to result in an unfavorable change in participant risk/benefit. Enrollment may be temporarily held, if needed, for the SET to evaluate the emerging data. The SET charter will outline the communication plan regarding decisions or recommendations that are made by the SET.

4.2. Scientific Rationale for Study Design

The more recent introduction of T cell redirecting bispecific agents represents a particularly promising form of immunotherapy. Bispecific agents use heterobivalent binding through 2 separate antigen recognition domains; one that recognizes a tumor antigen and the other that targets CD3 on T cells to achieve tumor clearance and circumvents many resistance mechanisms (Ramadoss N S, Schulman A D, Choi S H, et al. J Am Chem Soc. 2015; 137(16):5288-5291).

PSMA is a transmembrane protein expressed in the normal prostate and its expression is increased during malignant transformation including expression on bone metastases (Chang S S et al, Urology. 2001; 57(4):801-805). In addition, PSMA is over-expressed in the neovasculature of other malignant tumors (Baccala A, et al., Urology. 2007; 70(2): 385-390; Chang S S. Rev Urol. 2004; 6(Suppl 10): S13-S18; Chang S S et al. Cancer Res. 1999; 59(13):3192-3198. It is hypothesized that the study drug will direct the body's immune cells to kill these malignant cells overexpressing PSMA. The mechanism of action of the study drug enables T cell-mediated cytotoxicity through recruitment of CD3 expressing T cells to the PSMA expressing target cell. This mechanism for cell killing is unique, which offers an opportunity to treat patients whose disease has proved resistant to current therapy.

4.2.1. Study-Specific Ethical Design Considerations

This study is being conducted to evaluate the safety, pharmacokinetics, pharmacodynamics, and potential clinical benefit of the study drug following repeat doses to participants with mCRPC. The results of this study will provide useful information for further development of the compound. The primary ethical concern is that the risks and benefits associated with the administration of the study drug in this FIH study are unknown. To evaluate the study drug-related risks in humans, in vitro and in vivo evaluations were conducted using tumor cell lines. Preclinical toxicology and PK/PD studies were conducted in the *cynomolgus* monkey as this was the only relevant species demonstrating binding of both the PSMA and CD3 arms of the study drug. Although non-clinical studies indicate a potential for anti-tumor activity in the dose range proposed for evaluation in this study, the therapeutic benefit of the study drug has not been determined in humans. The main findings identified for the study drug in studies conducted in *cynomolgus* monkey were related to cytokine release (dose-limiting) and a generalized systemic inflammatory response.

It is possible that the participant's disease does not respond to the study drug or that the participant may receive a subtherapeutic dose, particularly in the lower dose cohorts. Furthermore, toxicities not observed in preclinical studies may occur. Based on the preclinical evaluation, there is reason to believe in a positive risk-benefit profile based on preclinical data. To ensure the well-being of participants treated in this study, safety and clinical benefit will be closely monitored, as discussed throughout this protocol.

As with all FIH dose-finding PK/PD studies, there are risks associated with venipuncture and multiple blood sample collection. To avoid multiple venipunctures, which cause additional discomfort and other potentially toxic effects, the use of IV indwelling catheters is permitted in this study (see investigator product preparation instructions [IPPI] for further details). The blood sample collection scheme was designed to collect the minimum number of blood samples that accurately and completely describe the PK/PD profile of the study drug. This minimizes the number of venipunctures and the total volume of blood collected from each participant during the study. Most blood samples will be collected during the first 8 weeks of treatment. The total blood volume to be collected is considered to be an acceptable amount of blood collected over this time period from the population in this study, based upon the standard of the American Red Cross.

The timing of imaging is designed to capture progression events and allow the clinical investigator to make timely treatment decisions yet balancing this with preventing participant overexposure to radiation. Efficacy assessments will occur as recommended by the internationally accepted Response Evaluation Criteria in Solid Tumors (RECIST) v1.1 or PCWG3 criteria.

Participants who have tumor biopsies may be at risk for toxicities associated with the biopsy procedure, which include pain, bleeding, and infection as well as the risks of any local or general anesthesia provided according to local standard of care.

Potential participants will be fully informed of the risks and requirements of the study and, during the study, participants will be given any new information that may affect their decision to continue participation. They will be told that their consent to participate in the study is voluntary and may be withdrawn at any time with no reason given and without penalty or loss of benefits to which they would otherwise be entitled. Only participants who are fully able to understand the risks, benefits, and potential adverse events of the study, and provide their consent voluntarily will be enrolled.

4.3. Justification for Dose

See Section 2.1.3. for the starting dose rationale.

4.4. End of Study Definition

A participant will be considered to have completed the study if he or she has died or has not met the withdrawal from study criteria (see Section 7). The end of study (study completion) is considered as the last safety assessment for the last participant in the study.

5. Study Population

Screening for eligible participants will be performed within 30 days before administration of the study drug. Refer to Section 5.4, Screen Failures for conditions under which the repeat of any screening procedures are allowed.

The inclusion and exclusion criteria for enrolling participants in this study are described below. If there is a question about these criteria, the investigator must consult with the appropriate sponsor representative and resolve any issues before enrolling a participant in the study. Waivers are not allowed.

5.1. Inclusion Criteria

Each potential participant must satisfy all of the following criteria to be enrolled in the study:

1. ≥18 years of age.
2. Criterion revised per amendment 1.
   2.1 Histology:
   Part 1: Metastatic CRPC (mCRPC) with histologic confirmation of adenocarcinoma. Adenocarcinoma with small-cell or neuroendocrine features is allowed.
   mCRPC is defined as: total serum testosterone ≤50 ng/dL or 1.7 nmol/L and evidence of progressive disease, defined as 1 or more PCWG3 criteria PSA level ≥1 ng/mL that has increased on at least 2 successive occasions at least 1 week apart, nodal or visceral progression as defined by RECIST 1.1 with PCGW3 modification, and/or appearance of 2 or more new lesions in bone scan.
   Part 2: mCRPC as defined above.
3. Criterion modified per Amendment 1.
   3.1 Prior treatment as follows:
   Part 1 and 2: mCRPC—at least 1 prior line of novel AR-targeted therapy (ie, abiraterone acetate, apalutamide, enzalutamide) for mCRPC. Patients who have received prior chemotherapy are also eligible if they have received at least 1 prior line of novel androgen receptor (AR)-targeted therapy.
4. Measurable or evaluable disease:
   Part 1: Either measurable or evaluable disease for prostate cancer.
   Part 2: At least one measurable lesion that can be accurately assessed at baseline by CT (or MRI where CT is contraindicated) and is suitable for repeated assessment as per RECIST v1.1. Documented progression of disease and a 4-week interval since completion of radiotherapy is required if the only site of measurable disease has been previously irradiated. Additionally, lesions selected at baseline or on treatment for biopsy cannot be selected as a target lesion for disease assessment.
5. Evidence of disease progression on prior therapy that requires a new line of treatment.
6. mCRPC: If the participant is receiving treatment with gonadotropin-releasing hormone agonists analogs (GnRH)(ie, participant who has not undergone bilateral orchiectomy), this therapy must have been initiated prior to first dose of study drug and must be continued throughout the study.
7. Participants with accessible lesions enrolled in selected PK/PD cohorts and in Part 2 must agree to undergo the mandatory fresh tumor biopsies, unless collection of the biopsy presents a safety risk.
8. Eastern Cooperative Oncology Group (ECOG) performance status grade of 0 or 1.
9. Hematology laboratory parameters within the following ranges, independent of transfusion or growth factors, within 3 weeks prior to first dose of study drug. Participant must not be transfusion dependent:
    a. Hemoglobin $\geq 9$ g/dL
    b. Absolute neutrophil count $\geq 1.5 \times 10^9$/L
    c. Platelets count $\geq 100 \times 10^9$/L
10. Chemistry laboratory parameters within the following range:
    a. Serum albumin $\geq 3.0$ g/dL
    b. Calculated or measured creatinine clearance >50 mL/min/1.73 m$^2$
    c. Serum total bilirubin $\leq 1.5 \times$ the upper limit of normal (ULN); in participants with Gilbert's syndrome, if total bilirubin is $\geq 1.5 \times$ ULN, measure direct and indirect bilirubin and if direct bilirubin is within the normal limit, participant may be eligible
    d. Aspartate aminotransferase (AST) and alanine aminotransferase (ALT)$\leq 2.5 \times$ ULN
11. Cardiac parameters within the following range:
    a. Left ventricular ejection fraction within institutional normal limits
    b. Corrected QT interval (QTcF or QTcB)$\leq 480$ milliseconds based on the average of triplicate assessments performed 5 minutes apart ($\pm 3$ minutes). This criterion is not applicable to participants with pacemakers.
12. Women of childbearing potential must have a negative highly sensitive serum ($\beta$-human chorionic gonadotropin [$\beta$-hCG]) at screening and prior to the first dose of study drug. Urine pregnancy test will be required every 4 weeks during treatment.
    A woman must be:
    Not of childbearing potential
    Of childbearing potential and
        Practicing a highly effective, preferably user-independent method of contraception (failure rate of <1% per year when used consistently and correctly) and agrees to remain on a highly effective method while receiving study drug and until 30 days after last dose.
        Pregnancy testing (serum or urine) within 30 days after the last study drug administration.
13. In addition to the user independent highly effective method of contraception, a male or female condom with or without spermicide is required, eg, condom with spermicidal foam/gel/film/cream/suppository. Male condom and female condom should not be used together (due to risk of failure with friction).
14. A male participant must wear a condom when engaging in any activity that allows for passage of ejaculate to another person. Male participants should also be advised of the benefit for a female partner to use a highly effective method of contraception as condom may break or leak.
15. Contraceptive (birth control) use, as described above, for both men or women should be consistent with local regulations regarding the acceptable methods of contraception for those participating in clinical studies. Typical use failure rates may differ from those when used consistently and correctly. Use should be consistent with local regulations regarding the use of contraceptive methods for participants in clinical studies.
16. A woman must agree not to donate eggs (ova, oocytes) for the purposes of assisted reproduction during the study and for at least 30 days after the last study drug administration.
17. A male participant must agree not to donate sperm for the purpose of reproduction during the study and for a minimum 90 days after receiving the last dose of study drug.
18. Willing and able to adhere to the prohibitions and restrictions specified in this protocol.
19. Must sign an informed consent form (ICF) indicating that he or she understands the purpose of, and procedures required for, the study and is willing to participate in the study.

5.2. Exclusion Criteria

Any potential participant who meets any of the following criteria will be excluded from participating in the study:
1. History of or known brain metastases.
2. Adenoma, oncocytoma, and mesenchymal renal cell tumors.
3. Criterion modified per Amendment 1
    3.1—mCRPC with a primary histology of prostatic neuroendocrine or small cell carcinoma tumor.
    Non-metastatic CRPC.
4. At least 2 weeks between prior anticancer treatment (including radiotherapy) discontinuation and the first dose of study drug, and toxicities have returned to Grade 1 or baseline.
5. Prior treatment with PSMA-targeted therapy including but not limited to chimeric antigen T cell receptors, PSMA T cell redirection therapy, PSMA-targeted monoclonal antibodies, including antibody drug conjugates. Prior treatment with a PSMA-targeted vaccine is permitted.
6. Solid organ or bone marrow transplantation.
7. Seizure or known condition that may predispose to seizure or intracranial masses such as schwannomas and meningiomas that are causing edema or mass effect.
8. Other active malignancy requiring systemic treatment 512 months prior to enrollment.
9. Any of the following within 6 months prior to screening:
    a. Myocardial infarction
    b. Severe or unstable angina
    c. Clinically significant ventricular arrhythmias
    d. Congestive heart failure (New York Heart Association class II to IV)
    e. Cerebrovascular accident or transient ischemic attack
    f. Any grade arterial event 10. Venous thromboembolic events (ie, pulmonary embolism) within 1 month prior to the first dose of study drug; uncomplicated (Grade ≤2) deep vein thrombosis is not considered exclusionary.
11. Uncontrolled hypertension (Grade ≥2); participants receiving anti-hypertensive therapy are allowed.
12. Known allergies, hypersensitivity, or intolerance to the study drug or its excipients (refer to Investigator's Brochure).
13. Concurrent use of any other anticancer treatment or investigational agent for the treatment of advanced disease.
14. Active infection or condition that requires treatment with systemic antibiotics within 7 days prior to the first dose of study drug.
15. Received immunosuppressive doses of systemic medications, such as corticosteroids (doses>10 mg/day prednisone or equivalent) within 2 weeks before first dose of study drug. A single course of corticosteroids is permitted as prophylaxis for imaging contrast (ie, for participants with allergies to contrast).
16. Active autoimmune disease within the past 2 years that requires systemic immunosuppressive medications (ie, chronic corticosteroid, methotrexate, or tacrolimus).
17. Major surgery (eg, requiring general anesthesia). Participant must have recovered adequately without sequelae at least 3 weeks prior to starting the study drug. Insertion of a central venous catheter under general anesthesia within 1 week prior to starting the study drug is permitted. Note: Participants with planned surgical procedures to be conducted under local anesthesia may participate.
18. Active or chronic hepatitis B or hepatitis C infection. Hepatitis B infection defined by a positive test for both hepatitis B surface antigen (HBsAg) and one antibody to either hepatitis B surface antigen or core antigens (anti-HBs and anti-HBc, respectively). Hepatitis C infection defined by a positive hepatitis C antibody.
   Participants who test positive for anti-HBs or anti-HBc must have hepatitis B DNA by polymerase chain reaction performed and confirmed as negative prior to study drug administration. Participants who test positive for hepatitis C antibody are eligible if previously treated and achieved a sustained viral response, defined as a negative viral load for hepatitis C after completion of the treatment for hepatitis.
19. History of human immunodeficiency virus (HIV) antibody positive, or tests positive for HIV at screening.
20. Vaccinated with a live vaccine within 28 days prior to the first dose of study drug; vaccination with inactivated vaccines, such as annual influenza vaccine, is allowed.
21. Pregnant, breast-feeding, or planning to become pregnant while enrolled in this study or within 30 days after the last dose of study drug.
22. Plans to father a child while enrolled in this study or within 90 days after the last dose of study drug.
23. Any condition for which, in the opinion of the investigator, participation would not be in the best interest of the participant (eg, compromise the well-being) or that could prevent, limit, or confound the protocol-specified assessments.

NOTE: Investigators should ensure that all study enrollment (inclusion/exclusion) criteria have been met at screening and prior to the first dose of study drug. If a participant's clinical status changes (including any available laboratory results or receipt of additional medical records) after screening but before the first dose of study drug is given such that he or she no longer meets all eligibility criteria, then the participant should be excluded from participation in the study. Section 5.4, Screen Failures, describes options for retesting.

5.3. Lifestyle Considerations

Potential participants must be willing and able to adhere to the following lifestyle restrictions during the course of the study to be eligible for participation:

1. Therapies that must be discontinued or substituted at least 4 weeks prior to first dose of study drug include medications known to lower the seizure threshold and products that may decrease PSA levels. Refer to Section 6.5.2 for details regarding prohibited and restricted therapy during the study.
2. Agree to follow all requirements that must be met during the study as noted in the eligibility (Inclusion and Exclusion) criteria (eg, contraceptive requirements).
3. Participants in dose escalation must be willing to be hospitalized after the first and second treatment doses, and any priming doses if administered, for at least 48 hours from the end of study drug infusion (IV flush) and as noted in Section 4.1.
4. Participants must agree to refrain from driving and engaging in hazardous occupations or activities during the timeperiod described in Section 6.1.2.4.

5.4. Screen Failures

Participant Identification, Enrollment, and Screening Logs

Participants who meet the criteria for a screen failure may be rescreened. Retesting of abnormal screening values that lead to exclusion are allowed only once during the screening phase (to reassess eligibility). The last result obtained prior to the first dose of study drug will be used to determine eligibility. The measurements collected at the time closest to, but prior to, the start of study drug administration will be defined as the baseline values for safety assessment and treatment decisions.

If a participant's clinical status changes (including any available laboratory results or receipt of additional medical records) after screening but before the first dose of study drug is given such that he or she no longer meets all eligibility criteria, the participant should be excluded from participation in the study.

The investigator agrees to complete a participant identification and enrollment log to permit easy identification of each participant during and after the study. This document will be reviewed by the sponsor study-site contact for completeness. The participant identification and enrollment log will be treated as confidential and will be filed by the investigator in the study file. To ensure participant confidentiality, no copy will be made. All reports and communications relating to the study will identify participants by participant identification and age at initial informed consent (as allowed by local regulations). In cases where the participant is not enrolled into the study, the date seen and age at initial informed consent (as allowed by local regulations) will be used.

6. Study Drug 6.1. Study drug Administration

Description of the Study Drug and Diluent

The study drug is a fully humanized IgG4-based bispecific antibody directed against the CD3 and PSMA receptors, produced by cultivation of recombinant Chinese Hamster Ovary cells followed by isolation, chromatographic purification, and formulation.

The study drug and diluent will be manufactured and provided under the responsibility of the sponsor. The study drug administration will be captured in the source documents and the electronic case report form (eCRF). For details on rescue medications, refer to Section 6.5.4. For a definition of the study drug overdose, refer to Section 8.4.

For the purpose of this study, 'the study drug' refers to the study drug and its diluent. All dosing information must be recorded in the eCRF. The enrollment staggering interval for participants in the dose escalation is provided in Section 4.1.1. Infusion times and recommendations may be adjusted by the sponsor in consultation with investigators, based on emerging safety information. Such changes will be documented in the study files, SET meeting minutes or the IPPI revisions. Infusion durations that exceed the planned length of time due to IV bag overfill, minor equipment calibration factors, or participant factors not under the control of administering personnel, will not be considered protocol deviations. The actual infusion time should be accurately recorded. Table provides details on drug administration.

TABLE 24

Study drug Administration
Table 24. Study drug Administration

| | |
|---|---|
| Starting dose/Dose levels | Dose escalation will be initiated at a starting dose of 0.1 µg/kg. Subsequent dose levels will be evaluated as per Section 4.1.1. A maximum dose level has not been identified for this study. |
| Route of administration/ Duration of infusion | Intravenous (IV) infusion will initially be administered over approximately 2 hours (±30 minutes). The recommended infusion duration time may change as determined by the SET based on emerging data and will be described in the IPPI. Longer infusion times may be needed if an IRR occurs or otherwise clinically indicated. Refer to the IPPI for complete details regarding the study drug administration. |
| Dosing Schedule/Regimen | The study will be initiated with a once weekly study drug infusion schedule (without priming). The study drug administration schedule (ie, weekly or twice weekly) may be changed and a priming dose schedule may be explored as determined by the SET based on emerging data. (see Section 4.1.1). Treatment dose schedules: Weekly: The study drug treatment dose administered once weekly. There must be at least 5 days between each study drug administration. Twice weekly (if explored): The study drug treatment dose administered twice weekly (ie, once every 3 to 4 days). There must be at least 72 hours between each study drug administration. After 6 months of treatment, the sponsor will evaluate, on a case by case basis, in consultation with the investigator, whether to decrease the frequency of dosing to every 2 weeks. Priming Dose Schedule: Priming dose(s) (Day 1) may be administered prior to the first treatment dose (Day 8); the dose and frequency will be determined by the SET.. Note: Study visit may occur ±2 days of the scheduled day. |
| Dosing instructions | The study drug infusions will be prepared and administered as described in the IPPI. Calculate the actual dose (µg) for administration based on the participant's weight (kg) on study Day 1. If the participant's weight on dosing day has changed by >10% from study Day 1 value, the dose should be recalculated. Administration of pre-infusion medications as described in Section 6.5.3. In the event of an IRR or CRS, see Table 26 and Table 27, respectively, for dosing instructions (eg, infusion rate change, interruption, and discontinuation). See Section 6.1.2 for necessary equipment/medications to be available prior to the study drug administration. |
| Hospitalization | See Section 4.1 for mandatory hospitalization(s). |
| Study drug instructions | Refer to the IPPI for the study drug preparation, storage, and administration. |
| Observation Period | The observation period begins after the end of IV flush. Beginning with the third treatment dose, participants should be observed for at least 2 hours after study drug administrations during the first 56 days. Subsequent doses: the participant may be released from the site after being evaluated by study site staff for at least 1 hour, and after completing all required assessments. |

6.1.1. Retreatment Criteria

Before each dose, the participant will be evaluated for possible toxicities that may have occurred. Laboratory results and general physical status must be reviewed. Toxicity and concurrent illnesses must have returned to Grade 1 or baseline (except alopecia). The participant must be without fever for at least 72 hours. Treatment with the study drug may resume provided the participant's clinical status meets all of the retreatment criteria outlined in 25 and none of the treatment discontinuation criteria presented in Section 7.1.

TABLE 25

Retreatment Criteria Prior to Each Dose

| Hematology[a,b] | | |
|---|---|---|
| Hemoglobin | | ≥8 g/dL |
| Platelets | | ≥75 × $10^9$/L |
| Neutrophils | | Absolute count ≥1.0 × $10^9$/L |
| Non-hematologic Toxicities | | |
| IRR | | See Section 6.1.2.1 for retreatment criteria. |
| CRS | | See Section 6.1.2.3 for retreatment criteria. |
| Neurotoxicity | | See Section 6.1.2.4 for retreatment criteria. |
| Other Non-hematologic Toxicity | Grade 2 (except alopecia) or | Treatment should be delayed until toxicity returns to Grade ≤1 or baseline, then therapy may be restarted at the same dose and schedule. |

TABLE 25-continued

Retreatment Criteria Prior to Each Dose

| | | |
|---|---|---|
| | Grade 3 | If Grade 3 toxicity (except for blood chemistry that can be corrected by supportive care) recurs, treatment should be delayed until toxicity returns to Grade ≤1 or baseline and the dose should |

TABLE 25-continued

Retreatment Criteria Prior to Each Dose

| | |
|---|---|
| Grade 4 | be reduced according to Section 6.6.2. Treatment should be delayed until the toxicity returns to Grade ≤1 or baseline and the dose should be reduced according to Section 6.6.2. |

[a]Transfusions and growth factors may be used to manage hematological toxicities.
[b]Must have adequately recovered from toxicity and be off transfusions or growth factors for at least 5 days before the next study drug administration.

In all cases of clinically significant impaired wound healing or imminent surgery or potential bleeding complications, it is recommended that dose administration be interrupted, appropriate clinical laboratory data (e.g., coagulation) be carefully monitored, and supportive therapy administered, where applicable. Dose administration may be restarted when it is considered safe, according to the investigator's assessment, at an appropriate dose determined in consultation with the sponsor.

6.1.2. Management Guidelines for Potential Toxicities

Best supportive care should be administered, as applicable. Management of specific potential toxicities noted in Section 2.3 are outlined in this section. Appropriate personnel and appropriate resuscitation equipment should be readily available in or near the infusion room and a trained physician should be readily available during the infusion of the study drug. Resources necessary for resuscitation include agents such as epinephrine and aerosolized bronchodilator, medical equipment such as oxygen, tracheostomy equipment, and a defibrillator. Vital signs and laboratory parameters must be monitored at regular intervals until the toxicity has normalized. Unscheduled pharmacokinetic, immunogenicity, cytokine, and pharmacodynamic samples should be collected in the event of an IRR or CRS event (see Section 1.3).

6.1.2.1. Management of Infusion-Related Reactions

Participants who experience IRR that manifest as wheezing, flushing, hypoxemia, fever, chills, rigors, bronchospasm, headache, rash, pruritus, arthralgia, hypo- or hypertension or other symptoms, should have the symptoms managed according to the recommendations provided in 26.

All Grade 3 or 4 IRRs should be reported within 24 hours to the sponsor medical monitor. If the event meets the criteria of a serious adverse event, follow serious adverse event reporting criteria in Section 8.3. After the initial IRR event, prophylactic medications must be administered as described in Section 6.5.3 prior to the next the study drug infusion.

TABLE 26

Dose Modification and Guidelines for the Management of Infusion-related Reactions

| Graded according to NCI CTCAE 5.0 | Treatment/Drug |
|---|---|
| Grade 1 or Grade 2 Mild or moderate reaction: requires therapy or infusion interruption but responds promptly to symptomatic treatment | Interrupt infusion: Start IV fluids; give diphenhydramine 50 mg IV (or equivalent) or paracetamol 650 to 1,000 mg (acetaminophen) or both; consider corticosteroids and bronchodilator therapy; monitor participant closely until recovery from symptoms. Restart infusion at 50% of initial rate: If no further complications occur after 30 minutes, the rate may be increased to 100% of the original infusion rate. Monitor participant closely. Symptoms recur: Stop the study drug infusion; administer diphenhydramine 50 mg IV and monitor participant until resolution of symptoms. The amount of the study drug infused must be recorded on the eCRF. Treatment rechallenge at next scheduled dose at the discretion of investigator, in consultation with the sponsor, if the participant has no further symptoms in the interval. |
| Grade 3 or 4 Grade 3: prolonged (eg, not rapidly responsive to symptomatic medication or brief interruption of infusion); recurrence of symptoms following initial improvement; hospitalization indicated for clinical sequelae (eg, renal impairment, pulmonary infiltrates) Grade 4: life-threatening; urgent intervention indicated (eg, pressor or ventilator support indicated) | Stop Infusion: Start IV saline infusion. Recommend the following treatment and any other therapies deemed necessary to manage the event: bronchodilators, epinephrine 0.2 to 1 mg of a 1:1000 solution for subcutaneous administration or 0.1 to 0.25 mg of a 1:10000 solution injected slowly for IV administration, and diphenhydramine 50 mg IV with methylprednisolone 100 mg IV (or equivalent). Investigators should follow institutional guidelines for the treatment of anaphylaxis. Monitor until medically stable, per the investigator's medical judgment. Discontinuation of treatment: See Section 7 for details. |

6.1.2.2. Management and Prevention of Immune-Related Adverse Events

The study drug may lead to specific immune-related adverse events (irAEs). Continuous, careful monitoring and timely management of irAEs may help to mitigate more severe toxicity. Symptomatic and best supportive care measures for specific potential irAEs should be in progress as soon as clinically indicated and should follow the institutional standards. These treatments may include corticosteroids and other immune suppressive agents as required for the specific irAEs.

6.1.2.3. Prevention and Management of Cytokine Release Syndrome

As the specific mode-of-action of the study drug is based on the binding and activation of T cells and the release of cytokines in the tumor environment, adverse events of CRS should be anticipated. The limited clinical experience with T cell activating bispecific antibodies appears to indicate that CRS occurs most frequently within minutes up to hours after the start of the infusion Klinger M, et al. Blood. 2012, 119(26):6226-6233; Lee D W et al. Blood. 2014, 124(2): 188-195; Zimmerman Z, et al. Int Immunol. 2015, 27(1): 31-37.

Clinical symptoms indicative of CRS may include but are not limited to fever, tachypnea, headache, tachycardia, hypotension, rash, and hypoxia caused by the release of cytokines. Also consider effects to other organs such as, hallucinations, confusion, headache, seizure, dysphasia, tremor, or other neurological toxicities. Potentially life-threatening complications of CRS may include cardiac dysfunction, adult respiratory distress syndrome, renal and hepatic failure, and disseminated intravascular coagulation. Participants should be closely monitored for early signs and symptoms indicative of CRS and the study drug infusion should be interrupted immediately. Laboratory testing for coagulation and inflammatory markers may be conducted as clinically indicated, to monitor for disseminated intravascular coagulation and inflammation, which can occur as manifestations of CRS. Cytokine release syndrome will be captured as an adverse event of special interest (see Section 8.3.5) and will be evaluated according to the NCI CTCAE version 5.0.

Recommendations for the clinical management of CRS are provided in Table 27 below and include treatment with tocilizumab ACTEMRA® (tocilizumab). Prescribing Information. South San Francisco, Calif.: Genentech, Inc; 2017. Administration of tocilizumab should be considered for Grade ≥2 CRS (per CTCAE v5.0); additionally, tocilizumab may be administered according to institutional standard of care guidelines. Therefore, ensure that tocilizumab is available at the site prior to infusion of the study drug (see Section 6.5.4). See Section 4.1 for hospitalization requirements for a CRS event.

Dose modification/discontinuation guidelines for participants who experience CRS are provided in Table 28. Post-treatment medications should be administered as needed. Participants must be hospitalized as described in Section 4.1.

TABLE 28

Dose Modification Guidelines for the Management of Cytokine Release Syndrome

| Toxicity Grade | Action |
| --- | --- |
| Grade 1 and 2 | Following recovery, continue at same dose. If these events occur during priming, the priming schedule may continue. |
| Grade 3 | $1^{st}$ occurrence: Following recovery to baseline or Grade ≤1 reduce current dose by 1 dose level.$^a$ If no additional Grade ≥3 CRS occurs, subsequent doses may be re-escalated after consultation with the sponsor. $2^{nd}$ occurrence: Permanently discontinue. |
| Grade 4 | Permanently discontinue the study drug and follow until recovery. |

$^a$See Section 6.6.2 for dose reduction schedule.

6.1.2.4. Neurological Adverse Events

It is not known if the study drug will cause neurologic toxicities; however, it is a potential risk due to the expression (cytoplasmic) of PSMA in the neuroglial cells of cerebellum and spinal cord. Additionally, neurological toxicity has been observed with CD3 redirecting agents such as CD19×CD3 blinatumomab. The etiology of these toxicities is not clear

TABLE 27

Guidelines for the Management of Cytokine Release Syndrome
Source: Modified based on Kymriah ™ (tisagenlecleucel) US package insert Kymriah ™ [US FDA Package Insert]. East Hanover, USA. Novartis Pharmaceutical Corporation; May 2018.

| Toxicity Grade | Cytokine Release Syndrome Severity | Management |
| --- | --- | --- |
| Grade 1 | Prodromal Syndrome: Low-grade fever, fatigue, anorexia | Observe in person; exclude infection; administer antibiotics per local guidelines if neutropenic; provide symptomatic support. |
| Grade 2 to Grade 3 | CRS requiring mild intervention (one or more of the following): High fever Hypoxia Mild hypotension | Administer antipyretics, oxygen, intravenous fluids and/or low-dose vasopressors as needed. Administer tocilizumab per institutional guidelines: Patient weight less than 30 kg: 12 mg/kg intravenously over 1 hour Patient weight greater than or equal to 30 kg: 8 mg/kg intravenously over 1 hour (maximum dose 800 mg) Repeat tocilizumab up to a maximum frequency of every 8 hours as needed if no clinical improvement |
| Grade 4 | CRS requiring moderate to aggressive intervention (one or more of the following): Hemodynamic instability despite intravenous fluids and vasopressor support Worsening respiratory distress, including pulmonary infiltrates increasing oxygen requirement including high-flow oxygen and/or need for mechanical ventilation Rapid clinical deterioration | Administer high dose or multiple vasopressors, oxygen, mechanical ventilation and/or other supportive care as needed. Administer tocilizumab: Patient weight less than 30 kg: 12 mg/kg intravenously over 1 hour Patient weight greater than or equal to 30 kg: 8 mg/kg intravenously over 1 hour (maximum dose 800 mg) Repeat tocilizumab as needed at a minimum interval of 8 hours if there is no clinical improvement. If no response to second dose of tocilizumab, consider a third dose of tocilizumab or pursue alternative measures for treatment of CRS. Limit to a maximum total of 4 tocilizumab doses. If no clinical improvement within 12 to 18 hours of the first tocilizumab dose, or worsening at any time, administer methylprednisolone 2 mg/kg as an initial dose, then 2 mg/kg per day until vasopressors and high flow oxygen are no longer needed, then taper. | and may be related specifically to CD19 expression, T cell redirection or cytokine release in general. In clinical trials with blinatumomab (CD19×CD3 BiTE), neurological toxicities occurred in approximately 50% of patients and included encephalopathy, convulsions, speech disorders, disturbances in consciousness, confusion and disorientation, and coordination and balance disorders. Most events resolved following interruption of blinatumomab, but some resulted in treatment discontinuation. Monitoring of signs and symptoms associated with neurological effects will occur throughout the study.

Based on the specific mode-of-action of the study drug, severe or serious neurological toxicities may occur. Early recognition of neurologic adverse events is critical to management. Participants should be monitored for neurological toxicities including, but not restricted to, speech disorders, convulsions, and disturbances in consciousness, confusion, disorientation, or coordination and balance disorders. Participants should be advised to seek medical evaluation if they notice impairment in motor function (e.g., weakness), changes in sensation (e.g., numbness), or symptoms suggestive of possible central nervous system abnormalities, such as new onset of headache or mental status changes.

Participants should also be advised to refrain from driving and engaging in hazardous occupations or activities, such as operating heavy or potentially dangerous machinery during the first 72 hours after treatment, and to be extended to the first 4 weeks of treatment for participants who experience Grade ≥2 neurologic toxicity that would impair such activity. If at any time the participant's status worsens, these restrictions should be reinstituted.

A basic neurological examination will be conducted by study site staff to evaluate neurological status as indicated in 29. If these or other neurological toxicities are observed, the sponsor medical monitor must be consulted. Dose modification/discontinuation guidelines for participants who experience neurological toxicity are provided in Table 29. Post-treatment medications should be administered as needed. Participants who experience neurotoxicity must be hospitalized as described in Section 4.1.

TABLE 29

Dose Modification Guidelines for the Management of Neurotoxicity

| Toxicity Grade | Action |
|---|---|
| Grade 1 and Grade 2 | Administer supportive therapy as per local/institutional guidelines. Following recovery, continue at same dose. If these events occur during priming, the priming dose administration may continue. |
| Grade 3 | Administer supportive therapy as per local/institutional guidelines.<br>1$^{st}$ occurrence: Following recovery to baseline or Grade ≤1 reduce current dose by 1 dose level$^a$<br>2$^{nd}$ occurrence: Permanently discontinue. |
| Grade 4 | Administer supportive therapy as per local/institutional guidelines. Permanently discontinue the study drug and follow until recovery. |

$^a$See Section 6.6.2 for dose reduction schedule.

6.2. Preparation/Handling/Storage/Accountability

Storage

The study drug must be stored at controlled temperatures. Detailed instructions for storage conditions and handling of the study drug will accompany clinical drug supplies to the clinical study sites. The study drug labels will contain information to meet the applicable regulatory requirements Accountability The investigator is responsible for ensuring that all the study drug and diluent received at the site is inventoried and accounted for throughout the study. The study drug and diluent administered to the participant must be documented on the study drug accountability form. All study drug and diluent will be stored and disposed of according to the sponsor's instructions. Study-site personnel must not combine contents of the study drug containers.

The study drug must be handled in strict accordance with the protocol and the container label and must be stored at the study site in a limited-access area or in a locked cabinet under appropriate environmental conditions. Unused study drug must be available for verification by the sponsor's study site monitor during on-site monitoring visits. The return to the sponsor of unused study drug will be documented on the study drug return form. When the study site is an authorized destruction unit and the study drug supplies are destroyed on-site, this must also be documented on the study drug return form.

Potentially hazardous materials such as used ampules, needles, syringes and vials containing hazardous liquids, should be disposed of immediately in a safe manner and therefore will not be retained for the study drug accountability purposes.

The study drug should be dispensed under the supervision of the investigator or a qualified member of the study-site personnel, or by a hospital/clinic pharmacist. The study drug and diluent will be supplied only to participants of this study. The study drug or diluent may not be relabeled or reassigned for use by other participants. The investigator agrees neither to dispense the study drug from, nor store it at, any site other than the study sites agreed upon with the sponsor.

6.3. Measures to Minimize Bias: Randomization and Blinding

Not applicable.

6.4. Study Drug Compliance

The study drug is to be administered as an intravenous infusion by the principal investigator or a qualified physician listed as a sub-investigator on required forms. Drug supplies for each participant will be inventoried and accounted for throughout the study. Administration of the study drug must also be recorded in the participant's source documents.

An interactive web response system will be used to assign centrally supplied study treatment kits for each participant enrolled in the study. The study drug may not be used for any purpose other than that outlined in this protocol, including other human studies, animal investigations, or in vitro testing.

Intravenous study drug will be administered in the controlled environment of a clinical research center, under the direct observation of qualified study-site personnel. The details of each administration will be recorded in the eCRF (including date, start, and stop times of the IV infusion, and volume infused). Precautions associated with the use of the study drug and prohibited concomitant medications will be reviewed with the participant.

Upon termination of the study, or at the request of the sponsor or its designee, the pharmacist must return the study drugs to the sponsor or its designee, after all drug supplies have been accounted for, unless it is destroyed at the site as agreed upon by both the sponsor and the site.

6.5. Concomitant Therapy

During screening, prior lines of therapy should be recorded on the eCRF. Throughout the study, investigators may prescribe any concomitant medications or treatments deemed necessary to provide adequate supportive care except for those listed in Section 6.5.2. All medications (including prescriptions and over-the-counter products, and transfusions of blood products) different from the study drug must be recorded throughout the study beginning with the signing of the ICF until 30 days after the last dose of study drug, or until the start of subsequent anticancer treatment, if earlier. This includes any concomitant therapies and any medications used to treat or support adverse events or serious adverse events. Recorded information will include a description of the type of the drug, dosing regimen, route of administration, duration of treatment, and its indication.

Modification of an effective preexisting therapy should not be made for the explicit purpose of entering a participant into the study. Participants with mCRPC without orchiectomy will remain on androgen deprivation therapy or the GnRH analog of investigator's choice throughout study treatment. All medications should be documented in the appropriate section of the eCRF.

6.5.1. Permitted Therapies

Participants are to receive full supportive care during the study. The following are examples of supportive therapies that may be used during the study:

Standard supportive care therapies (antiemetics, antidiarrheals, anticholinergics, antispasmodics, antipyretics, antihistamines, analgesics, antibiotics and other antimicrobials, histamine receptor [H2] antagonists or proton pump inhibitors, and other medications intended to treat symptoms or signs of disease or adverse events) as clinically indicated, according to institutional standards and as deemed necessary by the investigator.

Documented infectious complications should be treated with oral or IV antibiotics or other anti-infective agents as considered appropriate by the treating investigator for a given infectious condition, according to standard institutional practice.

Growth factor support, erythropoietin-stimulating agents, and transfusions such as red blood cells and platelets are permitted to treat symptoms or signs of neutropenia, anemia, or thrombocytopenia according to local standards of care; these agents are not allowed as prophylactic treatment during the DLT period.

Corticosteroids used as pretreatment medication of study drug are permitted, as noted in Table, and for the treatment of pre-existing diseases if daily dose is less than 10 mg prednisone or equivalent. Corticosteroids may be used as prophylaxis for imaging contrast.

Best supportive care to prevent or manage potential toxicities noted in Section 6.1.2.

Palliative radiotherapy to bone lesions.

GnRH agonists and antagonists

Medication that may decrease PSA levels (e.g., megestrol acetate, estrogens, progestins, 5 alpha-reductase inhibitors [.e.g, finasteride, dutasteride]) are permitted if started prior to the first dose of the study drug.

6.5.2. Prohibited or Restricted Therapies

The following medications are prohibited during the study. The sponsor must be notified in advance (or as soon as possible thereafter) of any instances in which prohibited therapies are administered.

Any chemotherapy, anticancer immunotherapy (other than the study drug), experimental therapy, or radiotherapy to visceral lesions.

Medications known to lower the seizure threshold.

To minimize the potential effect of CRS on CYP450 enzyme activities, which in turn could impact blood concentrations of CYP450 substrates, concomitant administration of CYP450 substrates, particularly those with narrow therapeutic index (e.g., warfarin) should be withheld for 48 hours during the first dose administration of the study drug. Participants should be monitored for potential toxicity from all CYP450 substrates and the dose of concomitant drugs may be adjusted as needed.

Chronic doses of corticosteroids in excess of 10 mg daily of prednisone or equivalent administered for >10 days are prohibited other than for the management of adverse events.

Other immunosuppressant agents unless used as protocol-specified pretreatment medications or to treat an adverse event (e.g., CRS).

Routine transfusions should not be given on the study drug administration days.

Herbal products.

6.5.3. Pre-Infusion Medications

Prior to each study drug infusion, participants in this study must receive premedication as noted below in Table 30. In the event the study drug infusion was interrupted for ≥4 hours due to acute toxicity, antihistamine and antipyretic treatment in Table 30 should be administered again. Pre-infusion medications may be changed based on emerging safety and other data as determined by the SET.

TABLE 30

Medications to be Administered Prior to the Study Drug Infusion

| Pre-medication | Dose | Administration | Action |
|---|---|---|---|
| Corticosteroid Medication[a] | | | |
| Note: Administer full (16 mg) dose of dexamethasone (or equivalent) noted below for first treatment dose and the priming dose(s) (if priming is administered). If no reactions are observed then administer half (ie, 8 mg) the corticosteroid dose for second treatment dose. If no reactions after second dose, then no further corticosteroids are required. If a Grade 3 CRS occurs, administer full (16 mg) dose of dexamethasone (or equivalent) prior to the next study drug administration. If no reactions are observed then administer half (ie, 8 mg) the corticosteroid dose for following study drug administration. Corticosteroids may be omitted if no further CRS event occurs after 2 consecutive study drug administrations. | | | |
| Glucocorticoid | dexamethasone (16 mg) | IV - administer approximately 30-60 minutes prior to the infusion | Required[b] - see above |
| Glucocorticoid | dexamethasone (8 mg) | IV - administer approximately 30-60 minutes prior to the infusion | Required[b] - see above |
| Other Medications | | | |
| Antihistamine | diphenhydramine (50 mg) or equivalent | Oral - administer at least 1 hour (±15 minutes) prior to study drug or IV - start infusion approximately 15 to 30 minutes prior to the study drug | Required |

TABLE 30-continued

Medications to be Administered Prior to the Study Drug Infusion

| Pre-medication | Dose | Administration | Action |
|---|---|---|---|
| Antipyretic | acetaminophen (650 mg to 1,000 mg) or equivalent | Oral or IV- administer approximately 15 to 30 minutes prior to the study drug | Required |
| H$_2$-antagonist | ranitidine (50 mg) or equivalent | IV - start infusion 30 (±15) minutes prior to the study drug | Optional |
| Antiemetic | ondansetron (16 mg) or equivalent | IV - start infusion approximately 15 to 30 minutes prior to the study drug | Optional |

Abbreviations: CRS = cytokine release syndrome; IRR = infusion-related reaction; IV = intravenous.
[a]Pre-infusion medications are only required up to and including the first treatment dose and the priming dose(s), if administered.

6.5.4. Rescue Medication

Recommendations for the clinical management of CRS include treatment with tocilizumab.[0] Therefore, the site must ensure that tocilizumab is available at the site prior to the administration of the study drug. The study site will supply tocilizumab rescue medication that will be sourced locally and reimbursed by the sponsor. The date and time of rescue medication administration as well as the name and dosage regimen of the rescue medication must be recorded.

6.5.5. Subsequent Anticancer Therapy

Subsequent anticancer therapy administered after the last dose of the study drug (including start and end date and best response, if available) should be documented in the eCRF.

6.6. Dose Modification

Any dose/dosage adjustment should be overseen by medically-qualified study-site personnel (principal or subinvestigator unless an immediate safety risk appears to be present). Dose delay and dose reduction are the primary methods for managing toxicities. The priming dose schedule may be implemented for specific toxicities noted in Section 6.6.3. Treatment will be discontinued if toxicity meets the criteria for treatment discontinuation in Section 7.1.

6.6.1. Dose Delays

If a dose is delayed by more than 72 hours, the subsequent doses are to be delayed assuring a minimum 5-day interval between weekly doses and 3-day interval between twice weekly doses. The dose de-escalation schedule shown in Table 31 should be followed for the events outlined in Section 6.1.2, in consultation with the sponsor.

In the event of DLT (Table) during treatment, treatment must be temporarily withheld, and supportive therapy administered, as clinically indicated. For other Grade 3 clinically significant toxicity during treatment, supportive therapy should be administered, and treatment may be withheld, as clinically indicated.

If the toxicity resolves to Grade ≤1 or baseline within 28 days, then treatment may be restarted, in consultation with the sponsor, except for criteria that meet reasons for discontinuation (see Section 7).

6.6.2. Dose Reductions

If determined to be in the best interest of the participant, the study drug may be restarted at the same or a lower dose, as shown in Table after consultation with the sponsor medical monitor provided the criteria for discontinuation of study therapy in Section 7 are not met. The lower dose levels shown in Table represent previously assessed dose levels declared to be safe.

TABLE 31

Dose Reduction Schedule

| Dose Reduction | Dose Level |
|---|---|
| Current dose | Current dose |
| First dose reduction | 1 dose level below or lower [a] |
| Second dose reduction | 2 dose levels below or lower [a] |

[a] A lower dose may be selected if deemed clinically appropriate, and after discussion between the sponsor medical monitor and investigator. Lower dose levels are those assessed and declared to be safe.

6.6.3. Dose Modification During the Priming Dose(s)

If the toxicity occurs during priming dose administration:

All retreatment criteria in Section 6.1.1 must be met prior to administration of the next priming or treatment dose of the study drug.

If a Grade 2 toxicity resolves to baseline or Grade ≤1 within 72 hours, the participant may continue study treatment at the last priming dose level.

If a Grade ≥3 CRS occurs during or after the priming dose, but resolves to Grade ≤1 within 72 hours, the dose will be reduced as described in Table. Dose re-escalation may be considered after consultation with the sponsor.

If a Grade 4 CRS occurs during or after the priming dose, permanently discontinue study treatment.

Retreatment may be allowed, in consultation with the sponsor, for other Grade ≥3 toxicities.

6.7. The Study Drug after the End of the Study

The sponsor will ensure that participants who continue to benefit from treatment with the study drug will be able to continue treatment after the data cutoff for the CSR. Participants will also be instructed that the study drug will not be made available to them after they have completed/discontinued the study drug and that they should return to their primary physician to determine standard of care.

7. Discontinuation of the Study Drug and Participant Discontinuation/Withdrawal

7.1. Discontinuation of the Study Drug

A participant will not be automatically withdrawn from the study if he or she has to discontinue the study drug. A participant's study drug must be discontinued if:

The participant received concurrent (non-protocol) anticancer treatment.

Confirmed disease progression unless judged by the investigator to be in the best interest of the participant to continue treatment with the study drug after obtaining written approval from the sponsor medical monitor.

Intercurrent illness that prevents further administration of the study drug

Participant refuses further treatment with the study drug

The participant becomes pregnant

An adverse event does not resolve to Grade ≤1 within 4 weeks of the last dose of the study drug such that the study drug is interrupted consecutively for more than 28 days, unless otherwise agreed to by the sponsor medical monitor and the investigator based on evidence of clinical benefit.

Grade 3 or Grade 4 non-hematologic toxicity reoccurring despite 2 dose reductions and best supportive care, unless otherwise agreed to by the sponsor medical monitor and the investigator based on evidence of clinical benefit.

Grade 3 IRR that reoccurs after 2 consecutive doses of the study drug

Grade 4 IRR (Section 6.1.2.1).

CRS:
    Grade 2 or 3 CRS that does not improve to Grade ≤1 within 7 days
    Grade 3 CRS that does not improve to Grade ≤2 within 5 days
    Two separate Grade 3 CRS events (recurrent)
    Grade 4 CRS Recurrent Grade 3 or any Grade 4 neurotoxicity (Section 6.1.2.4)

Grade 4 hematologic toxicity reoccurring despite 2 dose reductions and best supportive care, unless otherwise agreed to by the sponsor medical monitor and the investigator based on evidence of clinical benefit Following treatment discontinuation, the participant should complete the EOT visit (see Section 1.3). The primary reason for treatment discontinuation will be documented in the eCRF. Participants who withdraw for reasons other than toxicity will be replaced at the discretion of the sponsor (see Section 4.1.1).

7.2. Participant Discontinuation/Withdrawal from the Study

A participant will be withdrawn from the study for any of the following reasons:

Lost to follow-up
Withdrawal of consent
The sponsor discontinues the study

When a participant withdraws before completing the study, the reason for withdrawal is to be documented in the eCRF and in the source document. The study drug assigned to the withdrawn participant may not be assigned to another participant.

If a participant discontinues the study drug, the EOT and the post-treatment follow-up assessments should be obtained. If the reason for withdrawal from the study is withdrawal on consent, then no additional assessments are allowed.

7.2.1. Withdrawal from the Use of Research Samples

A participant who withdraws from the study will have the following options regarding the research sample(s):

The collected sample(s) will be retained and used in accordance with the participant's original informed consent for research samples.

The participant may withdraw consent for research sample(s), in which case the sample(s) will be destroyed, and no further testing will take place. To initiate the sample destruction process, the investigator must notify the sponsor study site contact of withdrawal of consent for the research samples and to request sample destruction. The sponsor study site contact will, in turn, contact the biomarker representative to execute sample destruction. If requested, the investigator will receive written confirmation from the sponsor that the sample(s) have been destroyed.

Withdrawal from the Research Samples while Remaining in the Main Study

The participant may withdraw consent for research samples while remaining in the study. In such a case, the research sample(s) will be destroyed. The sample destruction process will proceed as described above.

Withdrawal from the Use of Samples in Future Research

The participant may withdraw consent for use of samples for research. In such a case, samples will be destroyed after they are no longer needed for the clinical study. Details of the sample retention for research are presented in the ICF.

73. Lost to Follow-Up

If a participant is lost to follow-up, every reasonable effort must be made by the study site personnel to contact the participant and determine the reason for discontinuation/withdrawal. The measures taken to follow up must be documented. Refer to Section 7.2, Participant Discontinuation/Withdrawal From the Study.

8. Study Assessments and Procedures

Overview

The study is divided into 3 periods: a screening phase, a treatment phase, and a posttreatment follow-up phase. The Schedule of Activities summarizes the frequency and timing of study procedures and assessments applicable to this study.

All planned assessments, including clinical laboratory tests must be completed and the results reviewed at each clinic visit. If multiple assessments are scheduled for the same timepoint, it is recommended that procedures be performed in the following sequence: ECG, vital signs, blood draw. Treatment decisions will be based on safety and disease assessments performed at the site. More frequent study visits may be performed, and clinical evaluations may be repeated more frequently, if clinically indicated.

Blood collections for pharmacokinetic and pharmacodynamic assessments should be kept as close to the specified time as possible. Other measurements may be done earlier than specified timepoints if needed. Actual dates and times of assessments will be recorded in the source documentation and eCRF or laboratory requisition form. Repeat or unscheduled samples (ie, pharmacokinetic, pharmacodynamic, biomarkers) may be taken for safety reasons or for technical issues with the samples. Additional serum or urine pregnancy tests may be performed, as determined necessary by the investigator or required by local regulation, to establish the absence of pregnancy at any time during the participant's participation in the study. For each participant, approximately 23 mL of blood will be drawn during the screening phase. During the treatment phase, most samples will be collected during the first 8 weeks of treatment. Approximately 450 mL (weekly schedule) to 490 mL (twice weekly schedule) of blood will be drawn during this time. An additional 25 mL may be required if the priming schedule is implemented. Samples will be or evaluation of safety, pharmacokinetic, and pharmacodynamic parameters.

If the study drug is infused peripherally, blood samples must be drawn from a vein contralateral to the arm into which the study drug is infused or via a central line. If the study drug is infused via a central line, blood samples must be drawn from a vein in either arm.

Screening Phase

All participants must sign an ICF prior to the conduct of any study-related procedures. The screening phase begins when the first screening assessment is performed and within 30 days before the first dose of the study drug. During screening, if an assessment was performed as part of the participant's routine clinical evaluation and not specifically for this study, then it does not need to be repeated after signed informed consent has been obtained provided that the assessments fulfill the study requirements and are performed within the specified timeframe prior to the first dose of the study drug. Results of tests such as radiologic tests (eg, MRI and CT scans) are acceptable for screening if performed within 6 weeks (42 days) prior to the first dose of the study drug. Fresh tumor biopsy sample (from an accessible site of metastatic disease) is required at screening. However, a sample obtained within 6 weeks (42 days) to the first dose of the study drug is acceptable provided the participant is not receiving active anticancer therapy during this timeframe. These samples will be sent to a central laboratory designated by the sponsor (see Laboratory Manual for details).

Treatment Phase

The treatment phase begins on Day 1 with the administration of the study drug and continues until the completion of the EOT visit. During the treatment phase, a biopsy sample will be collected from selected cohorts. To facilitate safety monitoring, participants will be hospitalized as outlined in Section 4.1. During the study drug infusion, vital signs, temperature, and oxygen saturation measurements will be monitored at regular intervals. The participant will be evaluated for possible toxicities at each site visit. Participants may continue to receive the study drug until any of the treatment discontinuation criteria outlined in Section 7 are met. For participants who discontinue treatment due to disease progression, the disease progression form must be completed and sent to the sponsor medical monitor prior to treatment discontinuation. Upon discontinuation of the study drug, the participant will complete an EOT visit.

End-of-Treatment

The EOT visit is required for all participants, including those who discontinue the study drug for any reason, except for lost to follow-up, death, or withdrawal of consent for study participation. The EOT visit will be completed ≤30 (+7) days after the last dose of the study drug or prior to the start of a new anticancer therapy, whichever comes first. If a participant is unable to return to the site for the EOT visit or if the EOT visit occurs prior to Day 30 after the last dose of the study drug, the participant should be contacted to collect adverse events and concomitant medications up to 30 days after the last dose of the study drug or until the start of a subsequent anticancer therapy.

Post-Treatment Phase (Follow-Up)

The post-treatment follow-up phase starts after the EOT visit and will continue until one of the withdrawal from study criteria in Section 7.2 is met. If the study drug is discontinued prior to the onset of disease progression, as defined by the disease-specific response criteria, the results of disease evaluation performed per local standard of care should be recorded on the eCRF. Once disease progression is confirmed subsequent disease assessments are not required.

After the EOT visit, survival status, as well as subsequent anticancer therapy, will be obtained every 12 weeks until the end of study, unless the participant has died, is lost to follow-up, or has withdrawn consent. Adverse events will be collected up to 30 days after the last dose of the study drug. Investigators may recontact the participant or a designated representative to obtain long-term follow-up information regarding the participant's safety or survival status as noted in the informed consent form. If the information on survival is obtained via telephone contact, written documentation of the communication must be available for review in the source documents. If the participant has died, the date and cause of death will be collected and documented on the eCRF, if or when available. Where allowed by local law, public records may be used to document death and to obtain survival status.

Sample Collection and Handling

The actual dates and times of sample collection must be recorded in the eCRF or laboratory requisition form. Instructions for the collection, handling, storage, and shipment of samples are found in the Laboratory Manual/site investigational product and procedures manual (SIPPM) that will be provided. Collection, handling, storage, and shipment of samples must be under the specified, and where applicable, controlled temperature conditions as indicated in the Laboratory Manual/SIPPM. Refer to the Schedule of Activities for the timing and frequency of all sample collections.

Study-Specific Materials

The investigator will be provided with the following supplies:

Study protocol
Investigator's Brochure
Study site SIPPM
Laboratory Manual
IPPI and ancillary supplies
ECG manual
ECG machine
Interactive web response system manual
Electronic data capture manual
Sample ICF 8.1. Efficacy Assessments Assessment of disease includes the evaluations listed below. The frequency timing of these assessments is provided in the Schedule of Activities (Section 1.3).

Identical methodology (CT scan or MRI or $^{99m}$Tc bone scan) should be used for disease assessment at baseline, and throughout the course of the study, to characterize each identified and reported lesion to document disease status. Ultrasound, fluorine $^{18}$F-fluorodeoxyglucose positron emission tomography (PET), and plain X-rays are not acceptable methods of evaluating disease response. Imaging should not be delayed due to delays in the study drug administration.

Response to treatment will be assessed by the investigator at the site and the results will be recorded in the eCRF. Unscheduled assessments should be considered, if clinically indicated, and results collected in the eCRF. Images should be retained until study completion to facilitate central review, if requested by the sponsor.

Efficacy evaluations include the following:
mCRPC Cancer only: PSA and whole-body bone scans ($^{99m}$Tc)
CT scan
MRI Evaluation of treatment response for prostate cancer will be performed according to PCWG3 criteria (Sawicki L M et al. Eur J Nucl Med Mol Imaging. 2017; 44(1):102-107).

Participants with an objective response per RECIST v1.1 must have a confirmatory scan performed 4 weeks later. If a participant is assessed with partial response (PR) or complete response (CR) anytime during the study drug treatment but without confirmation ≥4 weeks later, the participant's best response will be classified as stable disease/progressive disease/not evaluable depending on the participant's next immediate assessments. During the study, disease response will be assessed using CT or MRI scans of the locations of known lesions.

If symptomatic deterioration occurs without documentation of radiographic progression, then the clinical findings used to make this determination must be specified in the eCRF as "clinical disease progression" and documented in the source documents. Every effort should be made to document objective progression via radiographic confirmation even after discontinuation of treatment for symptomatic deterioration. Clinical activity will be reported by the investigator in the eCRF.

After disease progression is documented, participants will have an EOT visit and enter the study post-treatment follow-up phase (Section 8). For participants who discontinue study treatment prior to disease progression, efficacy assessments according to the standard of care at the site will continue after the EOT visit until disease progression is documented, a new anticancer therapy is initiated, a maximum of 52 weeks, or the end of the study, whichever comes first; results should be recorded in the CRF.

8.1.1. Assessment of Disease Response and Progressive Disease 8.1.1.1. Soft Tissue Lesion Assessment (CT or MRI, Physical Examination)

Baseline disease burden will be assessed using CT scans of the neck, chest, abdomen, and pelvis, plus other areas as appropriate, with IV contrast. Participants who are intolerant of IV contrast agents may have CT scans performed with oral contrast and the reason for not using IV contrast will be documented in source documents. Subsequent efficacy evaluations during the study will include radiographic imaging of all disease sites documented at baseline.

Magnetic resonance imaging may be used to evaluate sites of disease that cannot be adequately imaged using CT (in any case where an MRI is desirable, it must be the imaging technique used to assess disease at baseline and at all subsequent response evaluations). For all other sites of disease, MRI assessments do not replace the required neck, chest, abdomen, and pelvic CT scans, unless CT scan is contraindicated. Brain MRI is required only if clinically indicated. CT scan of the head can be used if MRI is contraindicated.

For participants with palpable/superficial lesions, clinical disease assessments by physical examination should be performed at baseline and throughout the study drug treatment, as clinically indicated. Irradiated or excised lesions will be considered not measurable and monitored only for disease progression.

8.1.1.2. Bone Lesion Assessment in Prostate Cancer

Bone disease for participants with prostate cancer will be evaluated according to PCWG3 (ie, to evaluate duration of response) as follows:

Progression of soft tissue lesions measured by CT or MRI as defined in RECIST v1.1.

Progression by bone lesions observed by bone scan and based on PCWG3. Under these criteria, any bone progression must be confirmed by a subsequent scan ≥6 weeks later. The Week 8 scan (first post-treatment scan) should be used as the reference scan to which all subsequent scans are compared to determine progression. Bone progression is defined as one of the following:

1. Participant whose Week 8 scan is observed to have ≥2 new bone lesions compared to baseline scan will need to have a confirmatory scan performed ≥6 weeks later and would fall into one of the 2 categories below:
    a. Participant whose confirmatory scan (which is performed ≥6 weeks later) shows ≥2 new lesions compared to the Week 8 scan (ie, a total of ≥24 new lesions compared to baseline scan) will be considered to have bone scan progression at Week 8.
    b. Participant whose confirmatory scan did not show ≥2 new lesions compared to the Week 8 scan will not be considered to have bone scan progression at that time. The Week 8 scan will be considered as the reference scan to which subsequent scans are compared.
2. For a participant whose Week 8 scan does not have ≥2 new bone lesions compared to baseline scan, the first scan timepoint that shows ≥2 new lesions compared with the Week 8 scan will be considered as the bone scan progression timepoint if these new lesions are confirmed by a subsequent scan 26 weeks later.

8.1.1.3. Immune Response Assessment or Soft Tissue Lesions

Response to treatment may be assessed by the investigator according to immune-RECIST v1.1 (iRECIST) (Seymour L. et al. Lancet Oncol. 2017; 18(3), e143-e152).

8.1.2. Treatment after Initial Disease Progression

In a situation where there is progressive disease as per RECIST v1.1 or PCWG3 prostate criteria, but the treating physician strongly believes that continuation of study treatment is in the best interest of the participant, then with written approval of the sponsor medical monitor, the participant may be allowed to continue the study drug. In this situation, after progressive disease is recorded, localized therapy such as radiation may be performed as per standard of care.

Once the specific criteria of RECIST v1.1 defined disease progression or PCWG3 prostate criteria are met, a repeat efficacy evaluation should be performed at the next per protocol scheduled assessment time point or earlier, if clinically necessary (but no sooner than 4 weeks from the previous assessment) to confirm disease progression. This allowance to continue treatment despite initial radiologic progression considers the observation that some participants can have a transient tumor flare in the first few months after the start of immunotherapy but develop subsequent disease response (Zimmerman Z, et al. Int Immunol. 2015; 27(1): 31-37). Participants should continue study treatment at the discretion of the treating physician while waiting for confirmation of disease progression if they are clinically stable as defined by the following criteria:

Absence of clinical signs and symptoms indicating disease progression

Clinical disease progression not requiring immediate therapeutic intervention

No decline in ECOG performance status

Absence of progressive tumor at critical anatomical sites (eg, cord compression) requiring urgent alternative medical intervention If after the evaluation a participant is deemed clinically unstable he or she may be taken off study treatment without repeat imaging for confirmation of progressive disease.

Participants will be required to provide written informed consent (as per local regulations or requirements) prior to continuing study treatment. All procedures noted in the Schedule of Activities (see Section 1.3) will continue per protocol.

8.2. Safety Assessments

Safety will be monitored by the SET. Details regarding the Study Evaluation Team are provided in Section 4.1.4. Safety will be measured by adverse events, clinical laboratory test results, ECGs, vital sign measurements, physical examination findings (including basic neurological exam), and assessment of ECOG performance status score at the timepoints in Section 1.3. Safety monitoring may be performed more frequently, if clinically indicated, and adverse events should be evaluated by the investigator according to the standard practice.

Adverse Events

Adverse events will be reported and followed by the investigator. Adverse Event will be graded according to the NCI CTCAE Version 5.0. Any clinically relevant changes occurring during the study must be recorded on the Adverse Event section of the eCRF. Any clinically significant toxicities persisting at the end of the study will be followed by the investigator until resolution or until a clinically stable condition is reached.

The study will include the following evaluations of safety and tolerability according to the time points provided in the Schedule of Activities.

8.2.1. Physical Examination

General Physical Exam

The screening physical examination will include, at a minimum, participant's height, weight, general appearance, examination of the skin, ears, nose, throat, lungs, heart, abdomen, extremities, musculoskeletal system, lymphatic system, and nervous system. Thereafter, a symptom- and disease-directed physical examination will be conducted at subsequent timepoints. Abnormalities will be recorded in the appropriate section of the eCRF. Body weight will be also measured. Clinically significant post-baseline abnormalities should be recorded as adverse events.

Neurological Examination

A basic neurological examination will be conducted by study site staff. The assessments will be performed with the physical examination during screening and the treatment phase to evaluate participants for central nervous system-related toxicity. Any clinically significant change from baseline will be recorded as an adverse event(s).

ECOG Performance Status

The ECOG performance status scale will be used to grade changes in the participant's daily living activities.

8.2.2. Vital Signs

Temperature, pulse/heart rate, respiratory rate, blood pressure, and oxygen saturation will be assessed. Blood pressure and pulse/heart rate measurements will be assessed with a completely automated device. Manual techniques will be used only if an automated device is not available. Blood pressure and pulse/heart rate measurements should be preceded by at least 5 minutes of rest in a quiet setting without distractions (eg, television, cell phones).

8.2.3. Electrocardiogram

The triplicate 12-lead ECGs will be performed by qualified site personnel using an ECG machine provided by the sponsor that automatically calculates the heart rate and measures pulse rate; and RR, QRS, QT, and QTc intervals. The 3 individual ECG tracings should be obtained as close as possible in succession, approximately 5 minutes apart (±3 minutes). During the collection of ECGs, participants should be in a quiet setting without distractions (eg, television, cell phones). Participants should rest in a supine position for at least 5 minutes before ECG collection and should refrain from talking or moving arms or legs for at least 10 minutes before the ECG is performed. It is important to note that the actual test times should be consistent for each timepoint for both the screening and on-study ECGs, to minimize variability in the results obtained.

Additional cardiovascular assessments should be performed as clinically appropriate to ensure participant safety. The clinical investigator will review the results, including ECG morphology, for immediate management. Abnormalities noted at screening should be included in the medical history. ECG data will be submitted to a central laboratory and reviewed by a cardiologist for interval measurements and overall interpretation.

8.2.4. Echocardiogram or Multigated Acquisition Scan

Echocardiogram (ECHO) or multigated acquisition (MUGA) scan (if ECHO not available) will be performed at screening to establish baseline cardiac status. Further evaluations will be conducted if clinically indicated.

8.2.5. Clinical Safety Laboratory Assessments

Clinical laboratory samples will be collected. The investigator must review the laboratory results, document this review, and record any clinically relevant changes occurring during the study in the adverse event section of the eCRF. The laboratory reports must be filed with the source documents. Laboratory certificates or accreditation and normal ranges of the laboratory facility at the site must be submitted to the sponsor before the enrollment of any participant at the site. If the participant has the laboratory assessments conducted at a laboratory facility other than the one associated with the investigational site, the investigator must submit to the sponsor laboratory certificates or accreditation and normal ranges for that facility as well. The laboratory reports must be filed with the source documents.

8.3. Adverse Events and Serious Adverse Events

Timely, accurate, and complete reporting and analysis of safety information from clinical studies are crucial for the protection of participants, investigators, and the sponsor, and are mandated by regulatory agencies worldwide. The sponsor has established Standard Operating Procedures in conformity with regulatory requirements worldwide to ensure appropriate reporting of safety information; all clinical studies conducted by the sponsor or its affiliates will be conducted in accordance with those procedures.

Adverse events will be reported by the participant (or, when appropriate, by a caregiver, surrogate, or the participant's legally acceptable representative) from the time a signed and dated informed consent is obtained up to 30 days after the last dose of the study drug or until the start of subsequent anticancer therapy, if earlier (see Section 8.3.1 for time period for reporting adverse events). Anticipated events will not be recorded and reported as this is a FIH study, where all serious adverse events are important in understanding the safety of the product.

8.3.1. Time Period and Frequency for Collecting Adverse Event and Serious Adverse Event Information All Adverse Events All adverse events and special reporting situations, whether serious or non-serious, will be reported from the time a signed and dated ICF is obtained up to 30 days after the last dose of the study drug or until the start of subsequent anticancer therapy, if earlier, and may include contact for follow-up of safety. Adverse events will be followed by the investigator and graded according to the NCI CTCAE Version 5.0. Participants with Grade 3 or higher toxicity or unresolved adverse events that lead to the study drug discontinuation will continue to be assessed until recovery to Grade ≤1 or baseline, the event is deemed irreversible, the end of the study, or a maximum of 6 months, whichever comes first.

Serious adverse events, including those spontaneously reported to the investigator within 30 days after the last dose of the study drug, must be reported using the Serious Adverse Event Form. The sponsor will evaluate any safety information that is spontaneously reported by an investigator beyond the time frame specified in the protocol.

Serious Adverse Events

All serious adverse events occurring during the study must be reported to the appropriate sponsor contact person by study-site personnel within 24 hours of their knowledge of the event. Information regarding serious adverse events will be transmitted to the sponsor using the Serious Adverse Event Form, which must be completed and signed by a physician from the study site and transmitted to the sponsor within 24 hours. The initial and follow-up reports of a serious adverse event should be made by facsimile (fax).

8.3.2. Follow-Up of Adverse Events and Serious Adverse Events

Adverse events, including pregnancy, will be followed by the investigator.

8.3.3. Regulatory Reporting Requirements for Serious Adverse Events

The sponsor assumes responsibility for appropriate reporting of adverse events to the regulatory authorities. The sponsor will also report to the investigator (and the head of the investigational institute where required) all suspected unexpected serious adverse reactions (SUSARs). The investigator (or sponsor where required) must report SUSARs to the appropriate Independent Ethics Committee/Institutional Review Board (IEC/IRB) that approved the protocol unless otherwise required and documented by the IEC/IRB.

8.3.4. Pregnancy

All initial reports of pregnancy in female participants or partners of male participants must be reported to the sponsor by the study-site personnel within 24 hours of their knowledge of the event using the appropriate pregnancy notification form. Abnormal pregnancy outcomes (eg, spontaneous abortion, fetal death, stillbirth, congenital anomalies, ectopic pregnancy) are considered serious adverse events and must be reported using the Serious Adverse Event Form. Any participant who becomes pregnant during the study must discontinue treatment with the study drug. Follow-up information regarding the outcome of the pregnancy and any postnatal sequelae in the infant will be required.

8.3.5. Adverse Events of Special Interest

Cytokine release syndrome of any grade will be followed as part of standard safety monitoring activities by the sponsor. These events will be reported to the sponsor within 24 hours of awareness of the event irrespective of seriousness (ie, serious and nonserious adverse events) and will require enhanced data collection. Events of CRS (any grade) must be followed until recovery or until there is no further improvement.

8.4. Treatment of Overdose

As this is the first experience with the study drug in humans, the MTD is unknown; therefore, overdose cannot be defined. In the event of a dosing error of >25% of the intended dose, the investigator or treating physician should:
  Immediately contact the sponsor medical monitor.
  Closely monitor the participant for AE/SAE and laboratory abnormalities until the study drug can no longer be detected systemically (at least 5 days).
  Obtain a serum sample for pharmacokinetic analysis as soon as possible and repeat sequentially for 5 consecutive days from the date of the last dose of the study drug.
  Document the prescribed dose in the eCRF.
  Document the actual dose administered in the eCRF.

8.5. Pharmacokinetics and Immunogenicity 8.5.1. Evaluations

Venous blood samples will be collected for measurement of serum concentrations of the study drug and anti-study drug antibodies. Each serum sample will be divided into 3 aliquots (1 each for pharmacokinetic, anti-study drug antibodies, and a back-up). Samples collected for analyses of the study drug serum concentration and antibody to the study drug may additionally be used to evaluate safety or efficacy aspects that address concerns arising during or after the study period, for further characterization of immunogenicity or for the evaluation of relevant biomarkers (e.g., possible presence of soluble PSMA). Genetic analyses will not be performed on these serum samples. Participant confidentiality will be maintained. Additional information about the collection, handling, and shipment of biological samples can be found in the Laboratory Manual.

8.5.2. Analytical Procedures

Pharmacokinetics

Serum samples will be analyzed to determine concentrations of the study drug using a validated, specific, and sensitive immunoassay method by or under the supervision of the sponsor.

Immunogenicity

The detection and characterization of anti-study drug antibodies will be performed using a validated assay method by or under the supervision of the sponsor. All samples collected for detection of anti-study drug antibodies will also be evaluated for the study drug serum concentration to enable interpretation of the antibody data.

8.5.3. Pharmacokinetic Parameters and Evaluations

Blood samples will be collected during the study for measurement of pharmacokinetics of the study drug at the timepoints outlined in Table and Table 19. Samples will also be collected at the end-of-treatment visit following the study drug discontinuation.

The exact dates and times of blood sampling must be recorded for all samples collected on the laboratory requisition form. Refer to the Laboratory Manual for sample collection requirements. Collected samples must be stored under specified controlled conditions for the temperatures indicated in the Laboratory Manual.

If needed, samples collected may additionally be used to evaluate safety or efficacy aspects that address concerns arising during or after the study period, or address questions about drug characteristics that may arise later. Participant confidentiality will be maintained. Additional information about the collection, handling, and shipment of biological samples can be found in the Laboratory Manual.

Pharmacokinetic Parameters

Pharmacokinetic parameters will be estimated for individuals, and descriptive statistics will be calculated for each dose level. Correlation of C. and AUC with dose may also be explored. Pharmacokinetic parameters may include, but are not limited to, $C_{max}$, $T_{max}$, $AUC_{(t1-t2)}$, $AUC_{tau}$, $C_{min}$ and accumulation ratio (RA); parameters will be calculated if sufficient data are available for estimation. In addition, exploratory population pharmacokinetic-based approach may also be applied for pharmacokinetic analysis.

8.5.4. Immunogenicity Assessments (Anti-the Study Drug Antibodies)

Anti-study drug antibodies will be evaluated in serum samples collected from all participants during both Part 1 and Part 2 according to Table and Table 19. Additionally, serum samples will also be collected at the final visit from participants who are discontinued from study drug or withdrawn from the study.

Serum samples will be used to evaluate the immunogenicity of anti-study drug antibodies. Samples collected for immunogenicity analyses may additionally be used to evaluate safety or efficacy aspects that address concerns arising during or after the study period.

8.6. Pharmacodynamics

Cytokine production from peripheral blood will be analyzed prior to, and post-treatment of the study drug. Analysis will monitor levels of cytokines including, which may include, but are not limited to IL-1β, IL-2, IL-6, IL-8, IL-10, IFN-γ, and TNF-α, that can inform activation of immune cells.

To determine if treatment with the study drug results in increased antitumor activity by redirected T cell-mediated killing of PSMA-positive tumor cells and increased activation of cytotoxic T cells, whole blood samples and metastatic tissue samples may be analyzed to evaluate tumor and immune cell populations by methods such as flow cytometry or cytometry by time of flight (CyTOF). A fresh tissue tumor biopsy from an accessible site of metastatic disease will be collected and tested for PSMA expression and pharmacodynamic markers in the tumor.

Whole blood samples may be analyzed to evaluate peripheral immune cell populations using flow cytometry. Venous blood samples will be collected for exploratory evaluations of CD3 receptor occupancy (RO) on T cells via flow cytometry. Refer to the Laboratory Manual for further details on tumor tissue sample requirements, preparation, and shipping. See Section 1.3 for pharmacodynamic sample collection times.

8.7. Genetics

Pharmacogenomics or pharmacogenetics will not be evaluated in this study.

8.8. Biomarkers

Biomarker assessment in this study will focus on following objectives: 1) Evaluate immune response indicative of T cell response in tumor and blood as potential contribution of the study drug; 2) evaluate cytokine production in response to the study drug administration; and 3) evaluate other markers predictive of response to treatment including PSMA expression.

PSMA is frequently expressed at high levels on certain tumors compared to normal human prostate. Previous studies show variable expression of PSMA expression in patients with mCRPC. Furthermore, neuroendocrine tumors of the prostate were shown to be resistant to PSMA targeting therapies. Therefore, expression of PSMA and neuroendocrine markers will be assessed from tumor by IHC. Pre- and post-treatment expression of PSMA and neuroendocrine markers in tumor may be assessed to evaluate treatment effect. Tumor samples will be collected from selected cohorts.

Baseline tumor immune status could be predictive of response, therefore, T cell activation, exhaustion, and other immune cells affecting T cell responses will be assessed from baseline tumor and after treatment. Immune cell responses in the tumors and peripheral blood will be assessed before and after treatment. Cytokines released because of T cell activation will be assessed from serum samples collected before and after infusion. In addition, PBMCs will be collected and stored. Potential future use may include the identification of immunophenotype subpopulations that respond differently to the study drug.

During Part 2, in addition to the biomarkers mentioned above, circulating tumor DNA and CTCs will be collected and used to explore changes in T cell clonality, identify markers predictive of response/resistance and assess immune profiles within the peripheral blood and the tumor.

Biomarkers will be assessed in tumor tissue samples, whole blood, and serum. Biomarker samples may be used to help address emerging issues and to enable the development of safer, more effective, and ultimately individualized therapies. These samples will be collected only at sites where local regulations and shipping logistics permit and analyses will be performed at a central laboratory.

To understand tumor microenvironment changes pre- and post-treatment with the study drug, next generation RNA sequencing will be performed on metastatic tumor derived RNA samples. Genes and gene groups will be correlated with treatment outcomes.

Stopping Analysis

Biomarker analyses are dependent upon the availability of appropriate biomarker assays and clinical response rates. Biomarker analysis may be deferred or not performed, if during or at the end of the study, it becomes clear that the analysis will not have sufficient scientific value for biomarker evaluation, or if there are not enough samples or responders to allow for adequate biomarker evaluation. In the event the study is terminated early or shows poor clinical efficacy, completion of biomarker assessments is based on justification and intended utility of the data.

Additional Collections

If it is determined at any time before study completion that additional material is needed from a formalin-fixed, paraffin-embedded tumor sample for the successful completion of the protocol-specified analyses, the sponsor may request that additional material be retrieved from existing samples. Also, based on emerging scientific evidence, the sponsor may request additional material from previously collected tumor samples during or after study completion for a retrospective analysis. In this case, such analyses would be specific to research related to the study drug(s) or diseases being investigated.

8.9. Health Economics or Medical Resource Utilization and Health Economics

Not applicable.

9. Statistical Considerations

No formal hypothesis testing will be conducted. Data will be summarized using descriptive statistics. Continuous variables will be summarized using the number of observations, mean, standard deviation, coefficient of variation, median, and range as appropriate. Categorical values will be summarized using the number of observations and percentages as appropriate.

9.1. Statistical Hypotheses

Not applicable. Dose escalation will be guided by the statistical model described below.

9.1.1. Statistical Model Supporting Dose Escalation

The probability of DLTs by a two-parameter BLRM with the EWOC principle will the primary guide that helps the dose escalation and RP2D(s) recommendation, which is at or lower than the estimated MTD.

The incidence of DLTs, eg, DLT occurred or not during the DLT evaluation period (Section 4.1.3), is the primary variable for dose escalation. These accumulated DLT data from the eligible participants for the DLT evaluable analysis set will be used to model the relationship between the dose and DLT of the study drug. The two parameter BLRM will be used to calculate the probability of DLTs at dose d.

$$\mathrm{logit}(\pi(d)) = \log(\alpha) + \beta \cdot \log(d/d^*) \quad \alpha > 0, \beta > 0$$

where, $\pi(d)$ be the probability of DLTs when the study drug is given as a single agent at dose=d, d is the planned dose during the DLT evaluation period, and $\mathrm{logit}(\pi(d)) = \log[\pi(d)/\{1-\pi(d)\}]$ and $d^*$ is the reference dose.

Probability of DLT by BLRM

The probability of the true DLT rate for each dose level will be summarized as follows:

| | |
|---|---|
| [0%, 20%) | Under-dosing interval |
| [20%, 33%) | Targeted toxicity interval |
| [33%, 100%] | Excessive toxicity interval |

The probability of DLT will be calculated by BLRM, as described above, when all participants in a dose cohort complete the DLT evaluation period. The highest dose level for the next dose cohort will be recommended using the probability of DLTs at all dose levels of the study drug. The highest dose will need to satisfy EWOC principle, ie, less than 25% probability that the estimated DLT rate is in the excessive toxicity interval, and to have the highest probability that the estimated DLT rate is in the target toxicity interval. In addition, dose selection for the next cohort and the decision for MTD or RP2D(s) will follow the rules described in Section 4.1.1.

9.2. Sample Size Determination

During dose escalation, 1 or more participants will be enrolled at a dose level in the accelerated titration phase and 3 or more participants will be enrolled at a dose level in the standard titration phase with at least 6 participants enrolled at the safe and tolerable RP2D(s). The total number of participants enrolled will depend on the frequency of DLT and when the RP2D(s) is determined. The maximum sample size is approximately 70 participants.

Since Part 2 aims to evaluate the safety and preliminary clinical activity of the study drug at the RP2D, the sample size of approximately 20 (mCRPC) is selected to provide the point estimate with a reasonable precision. Table describes the point estimate and its 90% exact confidence interval (two sided) at selected frequencies for an event type of interest (eg, objective response or adverse events of special interest).

TABLE 32

Point Estimate and the 90% Exact Confidence Interval

| Number of participants with event | Observed probability of event | 90% exact CI (2-sided) |
|---|---|---|
| 0 | 0% | (NA, 14%) |
| 2 | 10% | (2%, 28%) |
| 4 | 20% | (7%, 40%) |
| 6 | 30% | (14%, 51%) |
| 8 | 40% | (22%, 61%) |
| 10 | 50% | (30%, 70%) |
| 12 | 60% | (39%, 78%) |

Particularly, if the true probability of an event of interest is 15% or higher, the probability of observing no participants experiencing this event is less than 5%.

9.3. Populations for Analyses

The analysis populations for this study are defined as follows:

All Treated Analysis Set: This set consists of participants who received at least 1 dose of the study drug. This analysis set will be considered as primary and will be used in all safety and efficacy summaries.

DLT Evaluable Analysis Set: This set is a subset of the 'All Treated Analysis' set. Participants who receive at least 75% of the planned doses of the study drug during the DLT observation period as defined in Section 4.1.3 will be included in this analysis.

Biomarker Analysis Set: This set consists of all participants who received at least 1 dose of the study drug and have at least 1 pre- or post-treatment biomarker measurement.

Pharmacokinetic Analysis Set: This set consists of all participants who receive at least 1 dose of the study drug and have at least 1 evaluable concentration measurement of the study drug.

9.4. Statistical Analyses 9.4.1. Efficacy Analyses

Endpoint Definitions

Overall response rate (ORR) is defined as the proportion of participants who have a PR or better according to the disease-specific response criteria. Response to treatment will be evaluated by investigator.

Duration of response (DOR) will be calculated from the date of initial documentation of a response (PR or better) to the date of first documented evidence of progressive disease, as defined in the disease-specific response criteria, or death due to any cause, whichever occurs first. For participants with a response (CR or PR) to treatment with disease that has not progressed and who are alive, data will be censored at the last disease evaluation before the start of any subsequent anticancer therapy.

Time to response (TTR) defined as the time from the date of first dose of the study drug to the date of first documented response.

Analysis Methods

Overall response rate will be tabulated together with its two-sided 90% exact confidence interval. In addition, the number and percentage of participants in each response category will be tabulated. For time to response, descriptive statistics will be used to summarize the results, including mean, median, standard deviation, and range for participants with a response. For DOR, the Kaplan-Meier method will be used for descriptive summaries.

9.4.2. Safety Analyses

All safety analyses will be performed on data from the 'all treated analysis set'. The baseline value for safety assessment is defined as the value collected at the time closest to, but prior to, the start of the first study drug administration. The safety parameters to be evaluated are the incidence, severity, and type of adverse events, clinically significant changes in the participant's physical examination findings, vital signs measurements, clinical laboratory and other clinical test results (e.g., ECG). Exposure to the study drug and reasons for discontinuation of study drug will be tabulated. Adverse events will be summarized by system organ class, preferred term, worst grade experienced by the participant, and by dose level.

Adverse Events

The verbatim terms used in the eCRF by investigators to identify adverse events will be coded using the Medical Dictionary for Regulatory Activities (MedDRA). Study drug-emergent adverse events are adverse events with onset during the study drug phase or that are a consequence of a pre-existing condition that has worsened since baseline. All reported adverse events will be included in the analysis. For each adverse event, the percentage of participants who experience at least 1 occurrence of the given event will be summarized by dose level/dose cohort.

Summaries, listings, datasets, or participant narratives may be provided, as appropriate, for those participants who die, who discontinue the study drug due to an adverse event, or who experience a severe or a serious adverse event. Listings of DLTs will use the DLT evaluable analysis set. DLTs will be listed and the incidence summarized by primary system organ class, preferred term, worst grade and type of adverse event, and dose levels.

Clinical Laboratory Tests

Laboratory data will be summarized by type of laboratory test. Reference ranges will be used in the summary of laboratory data. Descriptive statistics will be calculated for each laboratory analyte at baseline and for observed values and changes from baseline at each scheduled time point. Worst toxicity grade during treatment will be presented according to NCI CTCAE Version 5.0. Change from baseline to the worst toxicity grade experienced by the participant during the study will be provided as shift tables. A listing of participants with any laboratory results outside the reference ranges will be provided.

Electrocardiogram (ECG)

The effects of the study drug on QTc will be evaluated by means of descriptive statistics and frequency tabulations. Pharmacokinetic/pharmacodynamic models will be explored to understand and characterize the exposure-response relationship.

Vital Signs

Descriptive statistics of temperature, pulse/heart rate, and blood pressure (systolic and diastolic) values and changes from baseline will be summarized at each scheduled time point. The percentage of participants with values beyond clinically important limits will be summarized.

9.4.3. Other Analyses

Pharmacokinetic Analyses

The pharmacokinetic analysis will be performed on data from the 'pharmacokinetic analysis set'. All serum concentrations below the lowest quantifiable concentration or missing data will be labeled as such in the concentration database. Concentrations below the lower quantifiable concentration will be treated as zero in the summary statistics. Participants will be excluded from pharmacokinetic parameter analysis if their data do not allow for adequate assessment of parameters. All participants and samples excluded from the analysis will be clearly documented in the CSR.

Data will be listed for all participants with available serum concentrations per dose level. Participants will be excluded from the pharmacokinetic analysis if their data do not allow for accurate assessment of the pharmacokinetic (e.g., incomplete administration of the study drug; missing information of dosing and sampling times; concentration data not sufficient for pharmacokinetic parameter calculation).

Descriptive statistics will be used to summarize the study drug serum concentrations at each sampling timepoint by dose cohort for pharmacokinetic parameters of the study drug. Mean serum study drug concentration time profiles will be plotted, and individual serum concentration time profiles may also be plotted.

If appropriate data are available, population pharmacokinetic analysis of serum concentration-time data of the study drug may be performed using nonlinear mixed-effects modeling. Details will be given in a separate population pharmacokinetic analysis plan and the results of the population pharmacokinetic analysis will be presented in a separate report.

Biomarkers Analyses

Biomarker analyses will be stratified by clinical covariates or molecular subgroups using the appropriate statistical methods (eg, parametric or non-parametric, univariate or multivariate, analysis of variance, or survival analysis, depending on the endpoint). Correlation of baseline expression levels or changes in expression levels with response to time-to-event endpoints will identify responsive (or resistant) subgroups in addition to genes and pathways attenuated following treatment with the study drug.

Any pharmacodynamic measures will be listed, tabulated, and where appropriate, plotted. Participants may be grouped by cohort, dose schedule, or clinical response. As this is an open-label study with no control arm, statistical analyses will be done to aid in the understanding of the results.

Results of biomarker analyses may be presented in a separate report. Planned analyses are based on the availability of clinically valid assays and may be deferred if emerging study data show no likelihood of providing useful scientific information.

Receptor Occupancy Analysis

Descriptive statistics will be used to summarize the study drug CD3 RO results. The relationship between serum concentration of the study drug and RO, and between RO and downstream pharmacodynamic effects will be explored. Results of any such analyses may be presented in a separate report.

Immunogenicity Analyses

The incidence of anti-study drug antibodies will be summarized for all participants who receive at least 1 dose of the study drug and have appropriate samples for detection of antibodies to the study drug (i.e., participants with at least 1 sample obtained after their first dose of the study drug. A listing of participants who are positive for antibodies to the study drug will be provided. The maximum titers of antibodies to the study drug will be summarized for participants who are positive for antibodies to the study drug. Other immunogenicity analyses may be performed to further characterize the immune responses that are generated.

Pharmacodynamic Analyses

Pharmacodynamic samples received by the contract vendor or sponsor after the cutoff date will not be analyzed, and therefore, excluded from the pharmacodynamic analysis. Associations between baseline levels and changes from baseline in select markers and clinical response will be explored. Results of this analysis will be presented in a separate report.

Pharmacokinetic/Pharmacodynamic Analyses

Pharmacokinetic/pharmacodynamic models will be explored to understand and characterize the exposure-response relationship for key efficacy, safety, and pharmacodynamics/biomarker endpoints. The details will be provided in a separate analysis plan and the results of the analyses may be summarized in a separate report.

What is claimed is:

1. A method of treating prostate cancer in a patient, the method comprising administering to the patient a therapeutically effective amount an anti-PSMAxCD3 antibody fragment, wherein the anti-PSMAxCD3 antibody comprises a first binding domain that specifically binds PSMA and a second binding domain that specifically binds CD3, wherein the first binding domain comprises a heavy chain (HC) of SEQ ID NO:7 and a light chain (LC) of SEQ ID NO:8 and the second binding domain comprises a heavy chain (HC) of SEQ ID NO:17 and a light chain (LC) of SEQ ID NO:18.

2. The method of claim 1, wherein the patient has metastatic castration-resistant prostate cancer (mCRPC).

3. The method of claim 2, wherein the anti PSMAxCD3 antibody is administered to the patient intravenously (IV) at a dose of about 0.1 µg/kg at week 1.

4. The method of claim 3, wherein the anti PSMAxCD3 antibody is administered to the patient intravenously (IV) once a week starting at a dose of about 0.1 µg/kg.

5. The method of claim 4, wherein the anti PSMAxCD3 antibody is administered to the patient intravenously (IV) once a week starting at a dose of about 0.1 µg/kg, followed by a dose escalation regiment consisting of about 0.3 µg/kg at week 2, about 1 µg/kg at week 3, about 3 µg/kg at week 4, about 10 µg/kg at week 5, about 20 µg/kg at week 6, about 40 µg/kg at week 7, about 80 µg/kg at week 8, and about 120 µg/kg at week 9.

6. The method of claim 3, wherein the anti PSMAxCD3 antibody is administered to the patient intravenously (IV) two times per week starting at a dose of about 0.1 µg/kg.

7. A pharmaceutical composition comprising an antigen binding protein of SEQ ID NOs: 7, 8, 17 and 18 for use in the treatment of a prostate cancer in a patient, wherein the composition is at a dose of about 0.1 µg/kg at week 1, 0.3 µg/kg at week 2, 1 µg/kg at week 3, 3 µg/kg at week 4, 10 µg/kg at week 5, 20 µg/kg at week 6, 40 µg/kg at week 7, 80 µg/kg at week 8, and 120 µg/kg at week 9.

8. The composition of claim 7, wherein the patient has metastatic castration-resistant prostate cancer (mCRPC).

* * * * *